[12] United States Patent
Ono et al.

(10) Patent No.: US 6,797,726 B1
(45) Date of Patent: Sep. 28, 2004

(54) N-ALKOXYALKYL-N,N-DIALKYLAMINE DERIVATIVES OR SALTS THEREOF, AND REMEDIES FOR NERVE DEGENERATION DISEASES CONTAINING THE SAME

(75) Inventors: Satoshi Ono, Toyama (JP); Akihito Saitoh, Toyama (JP); Noboru Iwakami, Takaoka (JP); Masaya Nakagawa, Toyama (JP); Sumie Yamaguchi, Toyama (JP)

(73) Assignee: Toyama Chemical Co., Ltd., Tokyo (JP)

(*) Notice: Subject to any disclaimer, the term of this patent is extended or adjusted under 35 U.S.C. 154(b) by 0 days.

(21) Appl. No.: 09/926,739
(22) PCT Filed: Jun. 9, 2000
(86) PCT No.: PCT/JP00/03748
§ 371 (c)(1),
(2), (4) Date: Dec. 11, 2001
(87) PCT Pub. No.: WO00/76957
PCT Pub. Date: Dec. 21, 2000

(30) Foreign Application Priority Data

Jun. 11, 1999 (JP) ............................................. 11-165879

(51) Int. Cl.[7] .......................... A61K 31/38; A61P 43/00; C07D 333/56
(52) U.S. Cl. .......................... 514/443; 549/58; 548/179; 548/207
(58) Field of Search .............................. 514/443; 549/58

(56) References Cited

U.S. PATENT DOCUMENTS

| | | |
|---|---|---|
| 5,280,032 A | 1/1994 | Ono et al. |
| 5,472,984 A | 12/1995 | Ono et al. |
| 5,612,381 A | 3/1997 | Ono et al. |
| 5,658,904 A | 8/1997 | Ono et al. |
| 5,719,150 A | 2/1998 | Ono et al. |
| 5,807,887 A | 9/1998 | Ono et al. |
| 5,872,117 A | 2/1999 | Ono et al. |
| 5,922,721 A | 7/1999 | Ono et al. |
| 5,932,620 A | 8/1999 | Ono et al. |
| 5,968,935 A | 10/1999 | Ono et al. |
| 6,034,119 A | 3/2000 | Ono et al. |
| 6,103,754 A | 8/2000 | Ono et al. |

FOREIGN PATENT DOCUMENTS

| | | |
|---|---|---|
| JP | 4-95070 | 3/1992 |
| WO | 99/31056 | 6/1999 |

OTHER PUBLICATIONS

Hardy, et al, 1998, Science, vol. 282, 1075–1078.*

* cited by examiner

Primary Examiner—Deborah C. Lambkin
Assistant Examiner—Andrea D. Small
(74) Attorney, Agent, or Firm—Oblon, Spivak, McClelland, Maier & Neustadt, P.C.

(57) ABSTRACT

An N-alkoxyalkyl-N,N-dialkylamine derivative represented by the following general formula [1]:

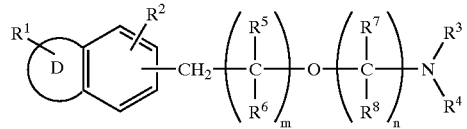

wherein the ring D represents a 5- or 6-membered heterocyclic ring or hydrocarbon ring; $R^3$ and $R^4$, which are the same or different, represent an unsubstituted or substituted alkyl, cycloalkyl or aralkyl group; and $R^1$, $R^2$, $R^5$, $R^6$, $R^7$, $R^8$, m and n are as defined in the specification, or a salt thereof has an anti-hypoxic activity, a nerve-protecting activity and a nerve regeneration promoting activity and is useful for the treatment of neurodegenerative diseases.

24 Claims, No Drawings

N-ALKOXYALKYL-N,N-DIALKYLAMINE DERIVATIVES OR SALTS THEREOF, AND REMEDIES FOR NERVE DEGENERATION DISEASES CONTAINING THE SAME

TECHNICAL FIELD

The present invention relates to novel N-alkoxyalkyl-N,N-dialkylamine derivatives or salts thereof.

BACKGROUND OF THE INVENTION

Dementia is classified into cerebrovascular dementia and neurodegenerative dementia, and a variety of agents such as ameliorants of cerebral circulation, ameliorants of cerebral function, etc. are used for treating these diseases.

The 1,2-ethanediol derivatives or salts thereof described in JP-A-3-232830 and JP-A-4-95070 are useful as the ameliorants of cerebral function, among which especially preferable is (R)-1-(benzo[b]thiophen-5-yl)-2-[2-(N,N-diethylamino)ethoxy]ethanol hydrochloride (hereinafter referred to as T-588).

Among the neurodegenerative dementia, the most popular is Alzheimer's disease (hereinafter referred to as AD), which is characterized by appearance of senile plaque of which the main component is an amyloid β protein (hereinafter referred to as Aβ) derived from a β amyloid precursor protein [Biochemical and Biophysical Research Communications, Vol. 120, Page 885 (1984)].

Aβ is considered to deposit on the nerve cells or blood vessels and to cause a symptom of dementia, etc. [Annual Review of Cell Biology, Vol. 10, Page 373 (1994)].

Further, it has also been reported that Aβ itself causes the apoptosis of cultured nerve cells (shrinkage of cell volume, a cell death, via the expression of gene, characterized by fragmentation of DNA) [Brain Research, Vol. 661, Page 147 (1994); Molecular Neurobiology, Vol. 10, Page 19 (1995)].

On the other hand, a rise in the quantity of 4-hydroxy-2-nonenal (hereinafter referred to as HNE) in the brain of AD patients has been reported [American Journal of Pathology, Vol. 150, Page 437 (1997)], and it has also been reported that HNE takes part in the cell death of cultured nerve cells caused by Aβ through intermediation of peroxidation of lipids [The Journal of Neuroscience, Vol. 17, Page 1046 (1997)].

It has also been reported that a cell death is caused if HNE is applied to upon cultured nerve cells, and that this cell death is apoptosis [The Journal of Neuroscience, Vol. 17, Page 5089 (1997)].

Further, a possibility that HNE is produced by an oxidation stress in various neurodegenerative diseases and the HNE exerts damage to nerve cells in the brain and spinal cord. For example, a rise in the quantity of HNE has been reported in the brain of patients of the Parkinson's disease [Proceedings of the National Academy of Sciences of the United States of America, Vol. 93, Page 2696 (1996)], and in the spinal cord of patients of the amyotrophic lateral sclerosis [Annals of Neurology, Vol. 44, Page 696 (1998)].

For these reasons, agents for controlling the neurocytotoxicity caused by Aβ and HNE are being studied for treating the neurodegenerative diseases such as Alzheimer's disease, Parkinson's disease, amyotrophic lateral sclerosis, etc.

Now, it is well known that neurotrophic factors such as a nerve growth factor (NGF) affecting the growth and regeneration of nerves exist in living organisms.

The neurotrophic factors are reported to interact not only to the central nervous diseases such as Alzheimer's disease but also to the peripheral nervous diseases such as diabetic neuropathy, drug-induced neuropathy, etc., and attempts are being made to use the neurotrophic factors for treatment of these diseases [Nou to Shinkei, Vol. 43, No. 12, Page 1101 (1991)].

Further, it has been reported that the impairment in the neuronal conduction in model animals with crushed sciatic nerve can be ameliorated by the regeneration of nerves promoted by NGF [Microsurgery, Vol. 16, Page 547 (1995)]. However, since neurotrophic factor is a protein of high molecular weight, there are many unsolved technical problems to apply it to nervous diseases.

Thus, it is demanded to develop a low molecular weight compound which is the same in function as the neurotrophic factor.

T-588 which is useful as a cerebral function ameliorant exhibits a protective action on the nerve cell death caused by Aβ [Society for Neuroscience, Abstracts, Vol. 24, No. 1, Page 228 (1998)], and further has an activity of reinforcing the function of NGF (WO96/12717), and is useful as an agent for treating the diseases of the central and peripheral nervous systems. However, a low molecular compound having yet stronger nerve cell-protecting and nerve regeneration-promoting activities with an intense anti-hypoxic activity is awaited.

DISCLOSURE OF THE INVENTION

The present inventors have conducted extensive studies with the aim of solving the problem mentioned above. As a result, it has been found that N-alkoxyalkyl-N,N-dialkylamine derivatives represented by the following general formula [1]:

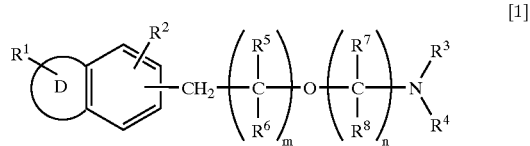

[1]

wherein $R^1$ and $R^2$ are the same or different and represent at least one group selected from the group consisting of a hydrogen atom, a halogen atom, an unsubstituted or substituted alkyl, aryl, aralkyl, alkoxy, aryloxy, alkylthio, arylthio, alkenyl, alkenyloxy, amino, alkylsulfonyl, arylsulfonyl, carbamoyl or heterocyclic group, an unprotected or protected amino, hydroxyl or carboxyl group, a nitro group and an oxo group; $R^3$ and $R^4$ are the same or different and represent an unsubstituted or substituted alkyl, cycloalkyl or aralkyl group; each of $mR^5$'s, $mR^6$'s, $nR^7$'s and $nR^8$'s are the same or different and represent a hydrogen atom or an alkyl group; the ring D represents a 5- or 6-membered heterocyclic or hydrocarbon ring; m represents an integer of 1–5; and n represents an integer of 1–6, or its salt have an anti-hypoxic activity, a nerve-protecting activity and a nerve regeneration promoting activity and are useful as an agent for treating neurodegenerative diseases. Based on this finding, the present invention has been accomplished.

Hereunder, the present invention will be explained in detail.

As used in this specification, the terms have the following meanings, unless otherwise indicated. The term "halogen atom" means a fluorine atom, a chlorine atom, a bromine atom or an iodine atom; "alkyl group" means a straight or branched chain $C_{1-12}$ alkyl group such as methyl, ethyl, propyl, isopropyl, butyl, isobutyl, tert-butyl, pentyl, hexyl, heptyl, octyl and the like; "lower alkyl group" means a straight or branched chain $C_{1-6}$ alkyl group such as methyl, ethyl, propyl, isopropyl, butyl, isobutyl, tert-butyl, pentyl, hexyl and the like; "cycloalkyl group" means a cyclopropyl, cyclobutyl, cyclopentyl or cyclohexyl group; "aryl group" means a phenyl, naphthyl, indanyl or indenyl group; "aralkyl group" means an ar-$C_{1-6}$-alkyl group such as benzyl, diphenylmethyl, trityl, or phenethyl group; "alkoxy group" means a straight or branched chain $C_{1-12}$ alkyloxy group such as methoxy, ethoxy, propoxy, isopropoxy, butoxy, isobutoxy, tert-butoxy, pentyloxy, hexyloxy, heptyloxy, octyloxy and the like; "lower alkoxy group" means a straight or branched chain $C_{1-6}$ alkyloxy group such as methoxy, ethoxy, propoxy, isopropoxy, butoxy, isobutoxy, tert-butoxy, pentyloxy, hexyloxy and the like; "aryloxy group" means a phenyloxy, naphthyloxy, indanyloxy or indenyloxy group; "alkylthio group" means a $C_{1-12}$ alkylthio group such as methylthio, ethylthio, propylthio, isopropylthio, butylthio, isobutylthio, tert-butylthio, pentylthio, hexylthio, heptylthio, octylthio and the like; "lower alkylthio group" means a $C_{1-6}$ alkylthio group such as methylthio, ethylthio, propylthio, isopropylthio, butylthio, isobutylthio, tert-butylthio, pentylthio, hexylthio and the like; "arylthio group" means a phenylthio, naphthylthio, indanylthio or indenylthio group and the like; "alkenyl group" means a $C_{2-12}$ alkenyl group such as vinyl, propenyl, butenyl, pentenyl, hexenyl, heptenyl, octenyl and the like; "lower alkenyl group" means a $C_{2-6}$ alkenyl group such as vinyl, propenyl, butenyl, pentenyl, hexenyl and the like; "alkenyloxy group" means a $C_{2-12}$ alkenyloxy group such as vinyloxy, propenyloxy, butenyloxy, pentenyloxy, hexenyloxy, heptenyloxy, octenyloxy and the like; "lower alkenyloxy group" means a $C_{2-6}$ alkenyloxy group such as vinyloxy, propenyloxy, butenyloxy, pentenyloxy, hexenyloxy and the like; "alkynyl group" means a $C_{2-6}$ alkynyl group such as ethynyl, 2-propynyl, 2-butynyl and the like; "acyl group" means formyl, alkylcarbonyl or aroyl group; "alkylcarbonyl group" means a $C_{2-6}$ alkylcarbonyl group such as acetyl, propionyl and the like; "aroyl group" means an arylcarbonyl group such as benzoyl, naphthylcarbonyl and the like; "acyloxy group" means an acyloxy group such as acetyloxy, pivaloyloxy, phenylacetyloxy, 2-amino-3-methylbutanoyloxy, ethoxycarbonyloxy, benzoyloxy, 3-pyridylcarbonyloxy and the like; "alkylamino group" means a mono- or di-$C_{1-6}$-alkylamino group such as methylamino, ethylamino, n-propylamino, isopropylamino, n-butylamino, dimethylamino, diethylamino, diisopropylamino, di-n-butylamino and the like; "alkylsulfonyl group" means a $C_{1-12}$ alkylsulfonyl group such as methylsulfonyl, ethylsulfonyl, n-propylsulfonyl, isopropylsulfonyl, n-butylsulfonyl, isobutylsulfonyl, sec-butylsulfonyl, tert-butylsulfonyl, pentylsulfonyl, hexylsulfonyl, heptylsulfonyl, octylsulfonyl and the like; "lower alkylsulfonyl group" means a $C_{1-6}$ alkylsulfonyl group such as methylsulfonyl, ethylsulfonyl, n-propylsulfonyl, isopropylsulfonyl, n-butylsulfonyl, isobutylsulfonyl, sec-butylsulfonyl, tert-butylsulfonyl, pentylsulfonyl and the like; "arylsulfonyl group" means phenylsulfonyl group, p-toluenesulfonyl group, naphthylsulfonyl group or the like; "alkylsulfonyloxy group" means a $C_{1-12}$ alkylsulfonyloxy group such as methylsulfonyloxy, ethylsulfonyloxy, n-propylsulfonyloxy, isopropylsulfonyloxy, n-butylsulfonyloxy, isobutylsulfonyloxy, sec-butylsulfonyloxy, tert-butylsulfonyloxy, pentylsulfonyloxy, hexylsulfonyloxy, heptylsulfonyloxy, heptylsulfonyloxy, octylsulfonyloxy and the like; "lower alkylsulfonyloxy group" means a $C_{1-6}$ alkylsulfonyloxy group such as methylsulfonyloxy, ethylsulfonyloxy, n-propylsulfonyloxy, isopropylsulfonyloxy, n-butylsulfonyloxy, isobutylsulfonyloxy, sec-butylsulfonyloxy, tert-butylsulfonyloxy, pentylsulfonyloxy and the like; "arylsulfonyloxy group" means phenylsulfonyloxy, p-toluenesulfonyloxy, naphthylsulfonyloxy or the like; and "heterocyclic group" means a 5- or 6-membered, fused ring type or crosslinked ring heterocyclic group containing at least one hetero atom selected from the group consisting of nitrogen, oxygen and sulfur atoms which ring may contain one or more oxygen atoms or sulfur atoms as hetero atoms constituting the ring, such as pyrrolidinyl, piperidinyl, piperazinyl, homopiperazinyl, homopiperidinyl, morpholinyl, thiomorpholinyl, tetrahydroquinolinyl, tetrahydroisoquinolinyl, quinuclidinyl, imidazolinyl, pyrrolyl, imidazolyl, pyrazolyl, pyridyl, pyrimidyl, quinolyl, quinolizinyl, thiazolyl, tetrazolyl, thiadiazolyl, pyrrolinyl, pyrazolinyl, pyrazolidinyl, purinyl, furyl, thienyl, benzothienyl, pyranyl, isobenzofuranyl, oxazolyl, isoxazolyl, benzofuranyl, indolyl, benzimidazolyl, benzoxazolyl, benzisoxazolyl, benzothiazolyl, quinoxalyl, dihydroquinoxalyl, 2,3-dihydrobenzothienyl, 2,3-dihydrobenzopyrrolyl, 2,3-4H-1-thianaphthyl, 2,3-dihydrobenzofuranyl, benzo[b]dioxanyl, imidazo[2,3-a]pyridyl, benzo[b]piperazinyl, chromenyl, isothiazolyl, isoxazolyl, oxadiazolyl, pyridazinyl, isoindolyl, isoquinolyl, 1,3-benzodioxonyl, 1,4-benzodioxanyl and the like.

The 5- or 6-membered heterocyclic ring represented by D includes heterocyclic rings containing at least one hetero atom selected from the group consisting of oxygen atom, nitrogen atom and sulfur atom as the hetero atom constituting the ring, of which examples include 5- or 6-membered aromatic heterocyclic rings such as triazine, pyridazine, pyrimidine, pyrazine, pyridine, furan, thiophene, pyrrole, oxazole, thiazole, imidazole, isoxazole, isothiazole, pyrazole, pyran and furazan rings and the like and 5- or 6-membered aliphatic heterocyclic rings such as tetrahydro-2H-pyran, tetrahydro-2H-thiopyran, piperidine, dioxane, oxathiane, morpholine, thiomorpholine, dithiane, piperazine, pyrrolidine, tetrahydrothiophene, tetrahydrofuran, pyrazolidine, imidazolidine, tetrahydroisothiazole, 1,3-dioxalane, 1,3-thiazolane, tetrahydroisoxazole, 1,3-oxazolane, dithiolane, oxathiolane and dioxalane rings and the like.

The 5- or 6-membered hydrocarbon ring represented by D includes 5- or 6-membered unsaturated hydrocarbon rings such as benzene, cyclohexene and cyclopentene rings and the like and saturated hydrocarbon rings such as cyclohexane and cyclopentane rings.

The substituent on the alkyl, cycloalkyl and aralkyl groups represented by $R^3$ and $R^4$ and the alkyl, aryl, aralkyl, alkoxy, aryloxy, alkylthio, arylthio, alkenyl, alkenyloxy, amino, alkylsulfonyl, arylsulfonyl, carbamoyl and heterocyclic groups represented by $R^1$ and $R^2$ includes at least one group selected from the group consisting of halogen atom, nitro group, lower alkyl group, cycloalkyl group, aryl group, aralkyl group, lower alkoxy group, aryloxy group, lower alkylthio group, lower alkenyl group, alkynyl group, alkylsulfonyl group, arylsulfonyl group, acyl group, acyloxy group, alkylamino group, carbamoyl group, unprotected or protected amino group, unprotected or protected hydroxyl group, unprotected or protected carboxyl group, heterocyclic group and the like.

The protecting group for carboxyl group includes all the groups usually usable for protection of carboxyl group, of which the examples include lower alkyl groups such as methyl, ethyl, propyl, isopropyl, 1,1-dimethylpropyl, butyl, tert-butyl and the like; aryl groups such as phenyl, naphthyl and the like; ar-(lower alkyl) groups such as benzyl, diphenylmethyl, trityl, p-nitrobenzyl, p-methoxybenzyl, bis (p-methoxyphenyl)methyl and the like; acyl-(lower alkyl) groups such as acetylmethyl, benzoylmethyl, p-nitrobenzoylmethyl, p-bromobenzoylmethyl, p-methanesulfonylbenzoylmethyl and the like; oxygen-containing heterocyclic groups such as 2-tetrahydropyranyl, 2-tetrahydrofuranyl and the like; halogeno-(lower alkyl) groups such as 2,2,2-trichloroethyl and the like; lower alkylsilyl-lower alkyl groups such as 2-(trimethylsilyl)ethyl and the like; acyloxy-(lower alkyl) groups such as acetoxymethyl, propionyloxymethyl, pivaloyloxymethyl and the like; nitrogen-containing heterocycle-lower alkyl groups such as phthalimidomethyl, succinimidomethyl and the like; cycloalkyl groups such as cyclohexyl and the like; lower alkoxy-lower alkyl groups such as methoxymethyl, methoxyethoxymethyl, 2-(trimethylsilyl)ethoxymethyl and the like; ar-(lower alkoxy)-(lower alkyl) groups such as benzyloxymethyl and the like; lower alkylthio-lower alkyl groups such as methylthiomethyl, 2-methylthioethyl and the like; arylthio-lower alkyl groups such as phenylthiomethyl and the like; lower alkenyl groups such as 1,1-dimethyl-2-propenyl, 3-methyl-3-butenyl, allyl and the like; and substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, tert-butylmethoxyphenylsilyl and the like.

The protecting groups for hydroxyl group include all the groups usually usable for protection of hydroxyl group, of which the examples include acyl groups such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)-ethoxy-carbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, ethoxyacetyl, phenoxyacetyl, pivaloyl, benzoyl and the like; lower alkyl groups such as methyl, tert-butyl, 2,2,2-trichloroethyl, 2-trimethylsilylethyl and the like; lower alkenyl groups such as allyl and the like; ar-(lower alkyl) groups such as benzyl, p-methoxybenzyl, 3,4-dimethoxybenzyl, diphenylmethyl, trityl and the like; oxygen-containing and sulfur-containing heterocyclic groups such as tetrahydrofuryl, tetrahydropyranyl, tetrahydrothiopyranyl and the like; lower alkoxy- and lower alkylthio-lower alkyl groups such as methoxymethyl, methylthiomethyl, benzyloxyethyl, 2-methoxyethoxymethyl, 2,2,2-trichloroethoxymethyl, 2-(trimethylsilyl)-ethoxymethyl, 1-ethoxyethyl, 1-methyl-1-methoxyethyl and the like; lower alkyl- and aryl-sulfonyl groups such as methanesulfonyl, p-toluenesulfonyl and the like; and substituted silyl groups such as trimethylsilyl, triethylsilyl, triisopropylsilyl, diethylisopropylsilyl, tert-butyldimethylsilyl, tert-butyldiphenylsilyl, diphenylmethylsilyl, tert-butylmethoxyphenylsilyl and the like.

The protecting groups for amino group include all the groups usually usable for protection of amino group, of which the examples include acyl groups such as trichloroethoxycarbonyl, tribromoethoxy-carbonyl, benzyloxycarbonyl, p-nitrobenzyloxycarbonyl, o-bromobenzyloxycarbonyl, (mono-, di-, tri-)chloroacetyl, trifluoroacetyl, phenylacetyl, formyl, acetyl, benzoyl, tert-amyloxycarbonyl, tert-butoxycarbonyl, p-methoxybenzyloxycarbonyl, 3,4-dimethoxybenzyloxycarbonyl, 4-(phenylazo) benzyloxycarbonyl, 2-furfuryloxycarbonyl, diphenylmethoxycarbonyl, 1,1-dimethylpropoxycarbonyl, isopropoxycarbonyl, phthaloyl, succinyl, alanyl, leucyl, 1-adamantyloxycarbonyl, 8-quinolyloxycarbonyl and the like; ar-(lower alkyl) groups such as benzyl, diphenylmethyl, trityl and the like; arylthio groups such as 2-nitrophenylthio, 2,4-dinitrophenylthio and the like; alkyl- or aryl-sulfonyl groups such as methanesulfonyl, p-toluenesulfonyl and the like; di-(lower alkylamino)-lower alkylidene groups such as N,N-dimethylamino-methylene and the like; ar-(lower alkylidene) groups such as benzylidene, 2-hydroxybenzylidene, 2-hydroxy-5-chlorobenzylidene and the like; nitrogen-containing heterocyclic alkylidene groups such as 3-hydroxy-4-pyridylmethylene and the like; cycloalkylidene groups such as cyclohexylidene, 2-ethoxycarbonylcyclohexylidene, 2-ethoxycarbonylcyclopentylidene, 2-acetylcyclohexylidene, 3,3-dimethyl-5-oxycyclohexylidene and the like; diaryl- or di-ar-(lower alkylphosphoryl) groups such as diphenylphosphoryl, dibenzylphosphoryl and the like; oxygen-containing heterocyclic alkyl groups such as 5-methyl-2-oxo-2H-1,3-dioxol-4-yl-methyl and the like; and substituted silyl groups such as trimethylsilyl and the like.

The salts of the compound of general formula [1] include usually known salts formed at the site of a basic group such as amino group and those formed at the site of an acidic group such as hydroxyl group, carboxyl group or the like. Examples of the salt formed at the site of a basic group include salts of mineral acids such as hydrochloric acid, hydrobromic acid, sulfuric acid and the like, salts of organic carboxylic acids such as formic acid, acetic acid, citric acid, oxalic acid, fumaric acid, maleic acid, malic acid, tartaric acid, aspartic acid, trichloroacetic acid, trifluoroacetic acid and the like, and salts of sulfonic acids such as methane-sulfonic acid, benzenesulfonic acid, p-toluenesulfonic acid, mesitylenesulfonic acid, naphthalenesulfonic acid and the like. Examples of the salt formed at the site of an acidic group include salts of alkali metals such as sodium, potassium and the like; salts of alkaline earth metals such as calcium, magnesium and the like; ammonium salts; and salts of nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, N,N'-dibenzylethylenediamine and the like. Among the salts mentioned above, preferred are pharmacologically acceptable ones.

Next, typical examples of the compound of the present invention are listed in the following Tables 1 to 7.

In the tables, Me means methyl group, Et means ethyl group, and Ph means phenyl group.

TABLE 1

$$R-CH_2-(CH_2)_m-O-(CH_2)_n-N\begin{smallmatrix}R^3\\R^4\end{smallmatrix}$$

| No. | R | m | n | $R^3$ | $R^4$ |
|---|---|---|---|---|---|
| 1 | 1-Naphthyl | 1 | 2 | methyl | methyl |
| 2 | 2-Naphthyl | 1 | 2 | methyl | methyl |
| 3 | 2-Naphthyl | 1 | 2 | ethyl | ethyl |
| 4 | 6-Quinolyl | 1 | 2 | ethyl | ethyl |
| 5 | Benzo[b]furan-5-yl | 1 | 2 | methyl | methyl |
| 6 | Benzo[b]furan-5-yl | 1 | 2 | ethyl | ethyl |
| 7 | Benzo[b]furan-5-yl | 1 | 2 | methyl | benzyl |
| 8 | 1,3-Benzodioxol-5-yl | 1 | 2 | methyl | methyl |
| 9 | 1,3-Benzodioxol-5-yl | 1 | 2 | ethyl | ethyl |
| 10 | 2,3-Dihydro-1H-5-indenyl | 1 | 2 | ethyl | ethyl |
| 11 | 1,4-Benzodioxan-6-yl | 1 | 2 | methyl | methyl |
| 12 | 2-Methyl-1,3-benzothiazol-5-yl | 1 | 2 | ethyl | ethyl |
| 13 | Benzo[b]thiophen-4-yl | 1 | 2 | ethyl | ethyl |
| 14 | Benzo[b]thiophen-5-yl | 1 | 2 | methyl | methyl |
| 15 | Benzo[b]thiophen-5-yl | 1 | 2 | methyl | ethyl |
| 16 | Benzo[b]thiophen-5-yl | 1 | 2 | methyl | 2-hydroxyethyl |
| 17 | Benzo[b]thiophen-5-yl | 1 | 2 | methyl | propyl |
| 18 | Benzo[b]thiophen-5-yl | 1 | 2 | methyl | isopropyl |
| 19 | Benzo[b]thiophen-5-yl | 1 | 2 | methyl | cyclopropyl |
| 20 | Benzo[b]thiophen-5-yl | 1 | 2 | methyl | allyl |
| 21 | Benzo[b]thiophen-5-yl | 1 | 2 | methyl | propargyl |
| 22 | Benzo[b]thiophen-5-yl | 1 | 2 | methyl | butyl |
| 23 | Benzo[b]thiophen-5-yl | 1 | 2 | methyl | benzyl |
| 24 | Benzo[b]thiophen-5-yl | 1 | 2 | ethyl | ethyl |
| 25 | Benzo[b]thiophen-5-yl | 1 | 2 | ethyl | allyl |
| 26 | Benzo[b]thiophen-5-yl | 1 | 2 | ethyl | propargyl |
| 27 | Benzo[b]thiophen-5-yl | 1 | 2 | ethyl | benzyl |
| 28 | Benzo[b]thiophen-5-yl | 1 | 2 | 2-hydroxyethyl | 2-hydroxyethyl |
| 29 | Benzo[b]thiophen-5-yl | 1 | 2 | propyl | propyl |

TABLE 2

$$R-CH_2-(CH_2)_m-O-(CH_2)_n-N\begin{smallmatrix}R^3\\R^4\end{smallmatrix}$$

| No. | R | m | n | $R^3$ | $R^4$ |
|---|---|---|---|---|---|
| 30 | Benzo[b]thiophen-5-yl | 1 | 2 | isopropyl | isopropyl |
| 31 | Benzo[b]thiophen-5-yl | 1 | 2 | cyclopropyl | benzyl |
| 32 | Benzo[b]thiophen-5-yl | 1 | 2 | allyl | benzyl |
| 33 | Benzo[b]thiophen-5-yl | 1 | 2 | propargyl | benzyl |
| 34 | Benzo[b]thiophen-5-yl | 2 | 2 | ethyl | ethyl |
| 35 | Benzo[b]thiophen-5-yl | 4 | 2 | methyl | methyl |
| 36 | Benzo[b]thiophen-5-yl | 1 | 3 | ethyl | ethyl |
| 37 | Benzo[b]thiophen-5-yl | 1 | 5 | ethyl | ethyl |
| 38 | Benzo[b]thiophen-5-yl | 2 | 3 | ethyl | ethyl |
| 39 | Benzo[b]thiophen-6-yl | 1 | 2 | methyl | methyl |
| 40 | Benzo[b]thiophen-7-yl | 1 | 2 | ethyl | ethyl |
| 41 | 2-Methylbenzo[b]thiophen-5-yl | 1 | 2 | ethyl | ethyl |
| 42 | 3-Methylbenzo[b]thiophen-5-yl | 1 | 2 | methyl | benzyl |
| 43 | 6-Methylbenzo[b]thiophen-5-yl | 1 | 2 | ethyl | ethyl |
| 44 | 2-Phenylbenzo[b]thiophen-5-yl | 1 | 2 | methyl | methyl |
| 45 | 2-Phenylbenzo[b]thiophen-5-yl | 1 | 2 | ethyl | ethyl |
| 46 | 2-Fluorobenzo[b]thiophen-5-yl | 1 | 2 | ethyl | ethyl |
| 47 | 3-Fluorobenzo[b]thiophen-5-yl | 1 | 2 | ethyl | ethyl |
| 48 | 4-Fluorobenzo[b]thiophen-5-yl | 1 | 2 | ethyl | ethyl |
| 49 | 6-Fluorobenzo[b]thiophen-5-yl | 1 | 2 | ethyl | ethyl |
| 50 | 7-Fluorobenzo[b]thiophen-5-yl | 1 | 2 | ethyl | ethyl |
| 51 | 2-Chlorobenzo[b]thiophen-5-yl | 1 | 2 | ethyl | ethyl |
| 52 | 4-Chlorobenzo[b]thiophen-5-yl | 1 | 2 | ethyl | ethyl |
| 53 | 3-Bromobenzo[b]thiophen-5-yl | 1 | 2 | ethyl | ethyl |
| 54 | 6-Methoxybenzo[b]thiophen-5-yl | 1 | 2 | methyl | methyl |
| 55 | 6-Dimethylaminobenzo[b]thiophen-5-yl | 2 | 2 | ethyl | ethyl |
| 56 | 2-Carboxybenzo[b]thiophen-5-yl | 1 | 2 | ethyl | ethyl |
| 57 | 2-(Aminocarbonyl)benzo[b]thiophen-5-yl | 1 | 2 | ethyl | ethyl |

TABLE 3

$$R-CH_2-(CH_2)_m-O-(CH_2)_n-N\begin{smallmatrix}R^3\\R^4\end{smallmatrix}$$

| No. | R | m | n | $R^3$ | $R^4$ |
|---|---|---|---|---|---|
| 58 | 1-Naphthyl | 1 | 2 | ethyl | ethyl |
| 59 | 1-Naphthyl | 1 | 2 | methyl | 2-hydroxyethyl |
| 60 | 2-Naphtyl | 1 | 2 | methyl | 2-hydroxyethyl |
| 61 | 2-(6-Methoxy-naphthyl) | 1 | 2 | methyl | methyl |
| 62 | 2-(6-Methoxy-naphthyl) | 1 | 2 | ethyl | ethyl |
| 63 | 2-(6-Methoxy-naphthyl) | 1 | 2 | methyl | 2-hydroxyethyl |
| 64 | 2-Methyl-1,3-benzothiozol-5-yl | 1 | 2 | methyl | 2-hydroxyethyl |
| 65 | Benzo[b]thiophen-4-yl | 1 | 2 | methyl | methyl |
| 66 | Benzo[b]thiophen-4-yl | 1 | 2 | methyl | 2-hydroxyethyl |
| 67 | Benzo[b]thiophen-5-yl | 1 | 2 | ethyl | 2-hydroxyethyl |
| 68 | Benzo[b]thiophen-5-yl | 1 | 2 | benzyl | 2-hydroxyethyl |
| 69 | Benzo[b]thiophen-5-yl | 1 | 2 | methyl | 2-hydroxypropyl |
| 70 | Benzo[b]thiophen-5-yl | 1 | 2 | methyl | 2-dimethylaminoethyl |
| 71 | Benzo[b]thiophen-5-yl | 1 | 2 | methyl | 3-hydroxypropyl |
| 72 | Benzo[b]thiophen-5-yl | 1 | 2 | methyl | 2-(1-hydroxypropyl) |
| 73 | Benzo[b]thiophen-5-yl | 1 | 2 | methyl | 4-methoxyhenzyl |
| 74 | Benzo[b]thiophen-5-yl | 1 | 2 | methyl | 4-fluorobenzyl |
| 75 | Benzo[b]thiophen-5-yl | 1 | 2 | methyl | 4-nitrobenzyl |
| 76 | Benzo[b]thiophen-5-yl | 1 | 2 | methyl | 2-methoxyethyl |
| 77 | Benzo[b]thiophen-5-yl | 1 | 2 | ethyl | cyclopropyl |
| 78 | Benzo[b]thiophen-6-yl | 1 | 2 | ethyl | ethyl |
| 79 | Benzo[b]thiophen-6-yl | 1 | 2 | methyl | 2-hydroxyethyl |
| 80 | Benzo[b]thiophen-6-yl | 1 | 2 | cyclopropyl | benzyl |
| 81 | Benzo[b]thiophen-7-yl | 1 | 2 | methyl | methyl |
| 82 | Benzo[b]thiophen-7-yl | 1 | 2 | methyl | 2-hydroxyethyl |
| 83 | Benzo[b]thiophen-4-yl | 2 | 2 | methyl | 2-hydroxyethyl |
| 84 | Benzo[b]thiophen-5-yl | 2 | 2 | methyl | 2-hydroxyethyl |

TABLE 4

$$R-CH_2-(CH_2)_m-O-(CH_2)_n-N\begin{smallmatrix}R^3\\R^4\end{smallmatrix}$$

| No. | R | m | n | $R^3$ | $R^4$ |
|---|---|---|---|---|---|
| 85 | Benzo[b]thiophen-6-yl | 2 | 2 | methyl | 2-hydroxyethyl |
| 86 | Benzo[b]thiophen-5-yl | 2 | 3 | methyl | 2-hydroxyethyl |
| 87 | Benzo[b]thiophen-5-yl | 1 | 3 | methyl | 2-hydroxyethyl |

TABLE 4-continued $$R-CH_2-(CH_2)_m-O-(CH_2)_n-N\begin{smallmatrix}R^3\\R^4\end{smallmatrix}$$

| No. | R | m | n | R³ | R⁴ |
|---|---|---|---|---|---|
| 88 | Benzo[b]thiophen-5-yl | 1 | 5 | methyl | 2-hydroxyethyl |
| 89 | 3-Dimethylaminobenzo[b]thiophen-5-yl | 1 | 2 | ethyl | ethyl |
| 90 | 2-Methylbenzo[b]thiophen-5-yl | 1 | 2 | methyl | 2-hydroxyethyl |
| 91 | 4-Chlorobenzo[b]thiophen-5-yl | 1 | 2 | methyl | methyl |
| 92 | 6-Chlorobenzo[b]thiophen-5-yl | 1 | 2 | methyl | methyl |
| 93 | 2-Fluorobenzo[b]thiophen-5-yl | 1 | 2 | methyl | 2-hydroxyethyl |
| 94 | 2-Fluorobenzo[b]thiophen-5-yl | 1 | 3 | methyl | 2-hydroxyethyl |
| 95 | 2-Fluorobenzo[b]thiophen-5-yl | 1 | 2 | methyl | 3-hydroxypropyl |
| 96 | 4-Fluorobenzo[b]thiophen-5-yl | 1 | 2 | methyl | methyl |
| 97 | 4-Fluorobenzo[b]thiophen-5-yl | 1 | 2 | methyl | 2-hydroxyethyl |
| 98 | 4-Fluorobenzo[b]thiophen-7-yl | 1 | 2 | methyl | methyl |
| 99 | 4-Fluorobenzo[b]thiophen-7-yl | 1 | 2 | methyl | 2-hydroxyethyl |
| 100 | 6-Fluorobenzo[b]thiophen-5-yl | 1 | 2 | methyl | benzyl |
| 101 | 6-Fluorobenzo[b]thiophen-5-yl | 1 | 2 | methyl | methyl |
| 102 | 6-Fluorobenzo[b]thiophen-5-yl | 1 | 2 | methyl | 2-hydroxyethyl |
| 103 | 6-Fluorobenzo[b]thiophen-7-yl | 1 | 2 | ethyl | ethyl |
| 104 | 6-Fluorobenzo[b]thiophen-7-yl | 1 | 2 | methyl | 2-hydroxyethyl |
| 105 | 5,7-Difluorobenzo[b]thiophen-6-yl | 1 | 2 | ethyl | ethyl |
| 106 | 5,7-Difluorobenzo[b]thiophen-6-yl | 1 | 2 | methyl | 2-hydroxyethyl |
| 107 | 6-Hydroxybenzo[b]thiophen-5-yl | 1 | 2 | ethyl | ethyl |
| 108 | 6-Hydroxybenzo[b]thiophen-5-yl | 1 | 2 | methyl | 2-hydroxyethyl |
| 109 | 6-Methoxybenzo[b]thiophen-5-yl | 1 | 2 | ethyl | ethyl |

TABLE 5

$$R-CH_2-(CH_2)_m-O-(CH_2)_n-N\begin{smallmatrix}R^3\\R^4\end{smallmatrix}$$

| No. | R | m | n | R³ | R⁴ |
|---|---|---|---|---|---|
| 110 | 6-Methoxybenzo[b]thiophen-5-yl | 1 | 2 | methyl | 2-hydroxyethyl |
| 111 | 6-Fluor-7-(methylthio)benzo[b]thiophen-5-yl | 1 | 2 | methyl | 2-hydroxyethyl |
| 112 | 6-Fluor-7-(methylthio)benzo[b]thiophen-5-yl | 1 | 2 | methyl | 2-hydroxyethyl |
| 113 | 6-Fluor-7-(methylthio)benzo[b]thiophen-5-yl | 1 | 2 | methyl | 2-hydroxyethyl |
| 114 | 2-(1-Hydroxy-1-methyl)ethyl-benzo[b]thiophen-5-yl | 1 | 2 | methyl | 2-hydroxyethyl |
| 115 | 2-(3-Pyridyl)benzo[b]thiophen-5-yl | 1 | 2 | ethyl | ethyl |
| 116 | Benzo[b]furan-5-yl | 1 | 2 | methyl | 2-hydroxyethyl |
| 117 | 5-Methoxybenzo[b]furan-6-yl | 1 | 2 | ethyl | ethyl |
| 118 | 5-Methoxybenzo[b]furan-6-yl | 1 | 2 | methyl | 2-hydroxyethyl |
| 119 | 1,4-Benzodioxan-6-yl | 1 | 2 | ethyl | ethyl |
| 120 | 2H-2,2-Dimethylchromen-6-yl | 1 | 2 | ethyl | ethyl |
| 121 | 4H-4-Chromenon-6-yl | 1 | 2 | methyl | methyl |
| 122 | 4H-4-Chromenon-6-yl | 1 | 2 | ethyl | ethyl |
| 123 | 4H-4-Chromenon-6-yl | 1 | 2 | methyl | 2-hydroxyethyl |
| 124 | 2H-2-Chromenon-6-yl | 1 | 2 | methyl | 2-hydroxyethyl |
| 125 | 1H-Benzo[b]imidazol-6-yl | 1 | 2 | methyl | 2-hydroxyethyl |
| 126 | 6-Quinoxalinyl | 1 | 2 | methyl | 2-hydroxyethyl |
| 127 | 1,2,3,4-Tetrahydro-6-quinoxalinyl | 1 | 2 | ethyl | ethyl |

TABLE 6

R—CH₂—A—O—B—C

| No. | R | A | B | C |
|---|---|---|---|---|
| 128 | 1-Naphtyl | —CH₂— | —CH₂C(Me)₂— | —NMe₂ |
| 129 | 2-Naphthyl | —CH₂— | —CH(Me)CH₂— | —NEt₂ |
| 130 | Benzo[b]thiophen-4-yl | —CH₂CH(Me)— | —CH₂CH₂— | —NMe₂ |
| 131 | Benzo[b]thiophen-5-yl | —CH(Me)— | —CH₂CH₂— | —NEt₂ |
| 132 | Benzo[b]thiophen-5-yl | —CH(Me)— | —CH₂CH₂— | —N(Me)CH₂CH₂OH |
| 133 | Benzo[b]thiophen-5-yl | —CH₂— | —CH₂CH(Me)— | —NEt₂ |
| 134 | Benzo[b]thiophen-5-yl | —CH₂— | —CH₂CH(Me)— | —N(Me)CH₂CH₂OH |
| 135 | Benzo[b]thiophen-5-yl | —CH(Me)— | —CH₂CH(Me)— | —NEt₂ |
| 136 | Benzo[b]thiophen-6-yl | —C(Me)₂— | —CH₂CH₂— | —NMe₂ |
| 137 | Benzo[b]thiophen-6-yl | —C(Me)₂— | —CH₂C(Me)₂— | —N(Me)CH₂CH₂OH |
| 138 | Benzo[b]thiophen-7-yl | —CH(Me)CH₂— | —CH₂CH₂— | —N(Me)CH₂CH₂OH |
| 139 | Benzo[b]furan-4-yl | —CH₂CH₂— | —C(Me)₂CH₂— | —N(Me)CH₂CH₂OH |
| 140 | Benzo[b]furan-5-yl | —CH₂— | —CH(Me)CH(Me)— | —NMe₂ |
| 141 | Benzo[b]furan-6-yl | —CH₂— | —CH₂CH(Me)CH₂— | —NEt₂ |
| 142 | Benzo[b]furan-7-yl | —CH₂CH(Me)— | —CH₂CH₂CH₂— | —N(Me)CH₂CH₂OH |

TABLE 7

R—CH$_2$—(CH$_2$)$_m$—O—(CH$_2$)$_n$—N(R$^3$)(CH$_2$)$_r$—O—R'

| No. | R | m | n | r | R$^3$ | R' |
|---|---|---|---|---|---|---|
| 143 | Benzo[b]-thiophen-5-yl | 1 | 2 | 2 | methyl | —COCH$_3$ |
| 144 | Benzo[b]-thiophen-5-yl | 1 | 2 | 2 | methyl | —COC(Me)$_3$ |
| 145 | Benzo[b]-thiophen-5-yl | 1 | 2 | 2 | methyl | —COOEt |
| 146 | Benzo[b]-thiophen-5-yl | 1 | 2 | 2 | methyl | —COPh |
| 147 | Benzo[b]-thiophen-6-yl | 1 | 2 | 2 | methyl | —COCH$_2$Ph |
| 148 | Benzo[b]-thiophen-7-yl | 1 | 2 | 2 | methyl | —COCH(NH$_2$)CH(Me)$_2$ |

TABLE 7-continued

R—CH$_2$—(CH$_2$)$_m$—O—(CH$_2$)$_n$—N(R$^3$)(CH$_2$)$_r$—O—R'

| No. | R | m | n | r | R$^3$ | R' |
|---|---|---|---|---|---|---|
| 149 | Benzo[b]-thiophen-8-yl | 1 | 2 | 2 | methyl | —CO(3-pyridyl) |
| 150 | Benzo[b]-thiophen-5-yl | 1 | 3 | 2 | methyl | —COCH$_3$ |
| 151 | Benzo[b]-thiophen-5-yl | 1 | 2 | 3 | methyl | —COC(Me)$_3$ |
| 152 | Benzo[b]-thiophen-5-yl | 1 | 3 | 2 | methyl | —COOEt |
| 153 | Benzo[b]-thiophen-5-yl | 2 | 2 | 2 | ethyl | —COCH$_3$ |

Next, the process for producing the N-alkoxyalkyl-N,N-dialkylamine derivatives of general formula [1] or salts thereof will be described below.

The N-alkoxyalkyl-N,N-dialkylamine derivatives of the general formula [1] or salts thereof can be produced according to the processes known per se or appropriate combination of such processes, such as the processes shown below.

Production Process 1

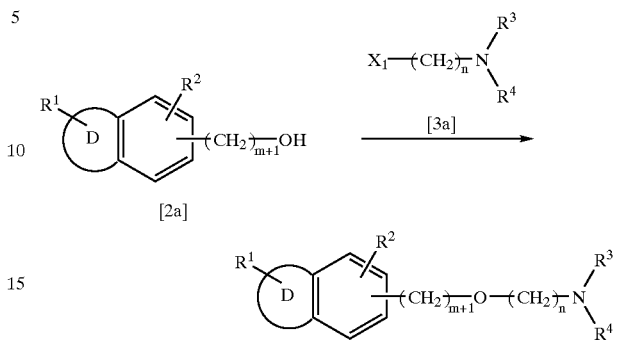

Production Process 2

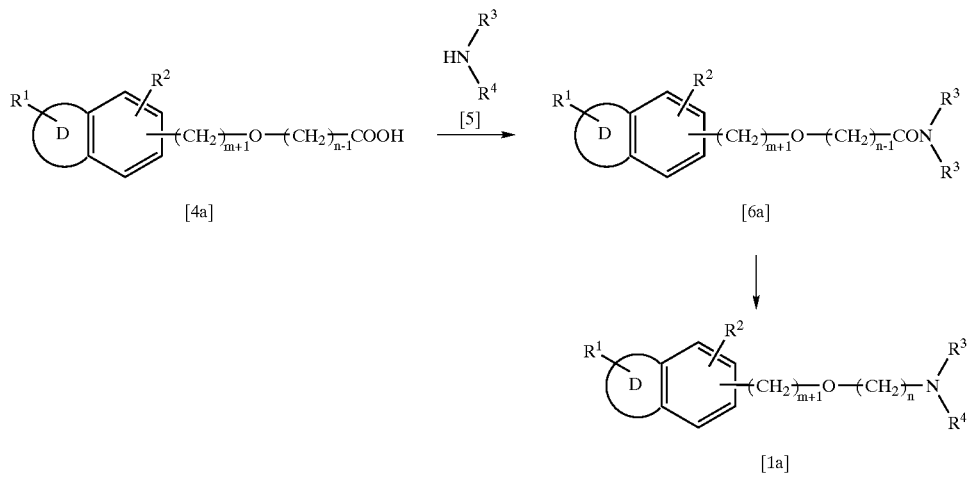

Production Process 3

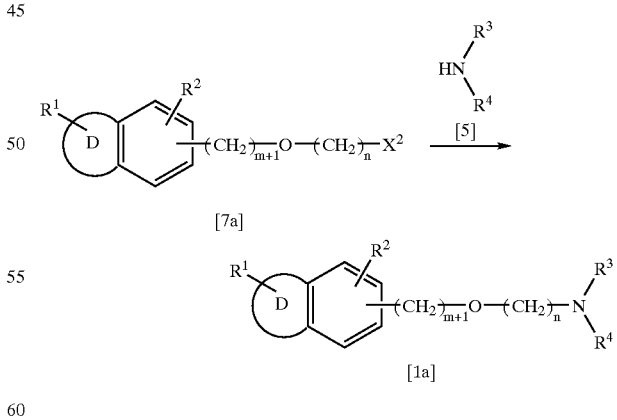

wherein R$^1$, R$^2$, R$^3$, R$^4$, m and n are as defined above and X$^1$ and X$^2$ independently represent a removing group.

As said removing group, for example, halogen atom, lower alkylsulfonyloxy group, arylsulfonyloxy group and the like can be referred to.

Next, the steps constituting the processes will be explained.

Production Process 1

A compound of general formula [2a] is reacted with a compound of general formula [3a] in the presence of a base to form a compound of general formula [1a].

This reaction is carried out according to a method well known per se, such as the method described in Tetrahedron, Letters, Vol. 38, Pages 3251–3254 (1975) or Shin Jikken Kagaku Koza, Vol. 14, [I], edited by Chemical Society of Japan, Pages 567–611 (1977, published by Maruzen) or any method analogous thereto.

As the base, for example, sodium hydride, sodium hydroxide, potassium hydroxide, potassium tert-butoxide and the like can be used.

The solvents which can be used in this reaction include, for example, halogenated hydrocarbons such as methylene chloride, chloroform and the like; ethers such as tetrahydrofuran, dioxane and the like; aromatic hydrocarbons such as benzene, toluene, xylene and the like; sulfoxides such as dimethyl sulfoxide and the like; amides such as N,N-dimethylformamide and the like; tertiary alcohols such as tert-butanol and the like; water; etc. These solvents can be used in the form of a mixture, if desired.

This reaction can be carried out in the presence or absence of a catalyst.

As the catalyst, the generally known quaternary ammonium phase transfer catalysts are used, among which preferred are tetra-n-butylammonium hydrogen sulfate, tetra-n-butylammonium bromide, and the like.

The compound of general formula [3a] and the base are both used at least in an equimolar amount to the compound of general formula [2a], and preferably in an amount of 1–20 mol per mol of the compound [2a]. The catalyst is used in an amount of 0.01–0.30 mol per mol of the compound [2a].

This reaction is usually carried out at a temperature of −50° C. to +200° C. and preferably 0° C. to +150° C., for a period of 10 minutes to 20 hours.

Production Process 2

(1) A compound of general formula [4a] or a reactive derivative thereof is reacted with a compound of general formula [5], whereby a compound of general formula [6a] can be produced.

This reaction is carried out according to a method known per se, such as the method described in Jikken Kagaku Koza, Vol. 22, edited by Chemical Society Japan, Pages 137–173 (1922, Maruzen) or any method analogous thereto.

As the reactive derivative of the compound of general formula [4a], acid halides, acid anhydrides, activated amides, activated esters, and the like can be referred to, for example.

In a case where the compound [4a] is used in the form of a free acid, the reaction is preferably carried out in the presence of a condensing agent.

The condensing agents which can be used include, for example, N,N-dialkylcarbodiimides such as N,N-dicyclohexylcarbodiimide and the like; halogenating agents such as thionyl chloride and the like; halogenated alkyl esters such as ethyl chloroformate and the like; activating amidating agents such as carbonyl-diimidazole and the like; and azide-forming agents such as diphenylphosphoryl azide and the like, etc.

The condensing agent is used at least in an amount equimolar to the compound of general formula [4a], and preferably in an amount of 1–5 mol per mol of compound [4a].

The solvents which can be used in this reaction include, for example, water; halogenated hydrocarbons such as methylene chloride, chloroform and the like; ethers such as tetrahydrofuran, dioxane and the like; aromatic hydrocarbons such as benzene, toluene, xylene and the like; sulfoxides such as dimethyl sulfoxide and the like; amides such as N,N-dimethylformamide and the like; esters such as ethyl acetate and the like; ketones such as acetone, methyl ethyl ketone and the like; nitrites such as acetonitrile and the like; hetero-aromatic compounds such as pyridine and the like; etc. These solvents can be used in the form of a mixture, if desired.

This reaction can be carried out in the presence of a base.

The bases which can be used include, for example, organic and inorganic bases such as triethylamine, diisopropylethylamine, 1,8-diazabicyclo[5.4.0]undec-7-ene, pyridine, potassium tert-butoxide, sodium carbonate, potassium carbonate, sodium hydride and the like.

The base is used in an amount of at lest equimolar amount to the compound of general formula [4a], and preferably 1–10 mol per mol of compound [4a].

The compound of general formula [5] is used in an amount of at least equimolar amount to the compound of formula [4a], and preferably 1–20 mol per mol of compound [4a].

This reaction is usually carried out at a temperature of −50° C. to +200° C. and preferably −30° C. to +100° C., for a period of 10 minutes to 20 hours.

(2) The compound of general formula [6a] is subjected to a conventional reduction reaction, whereby the compound of general formula [1a] can be obtained.

This reduction is carried out according to a method known per se, such as the method described in Shin Jikken Kagaku Koza, Vol. 15 [II], edited by Chemical Society of Japan, Pages 29–244 (1977, Maruzen), or any analogous method.

The solvents which can be used in this reaction include halogenated hydrocarbons such as methylene chloride, chloroform and the like; ethers such as tetrahydrofuran, dioxane and the like; aromatic hydrocarbons such as benzene, toluene, xylene and the like; alcohols such as methanol, ethanol, isopropanol and the like; etc. These solvents can be used in the form of a mixture, if desired.

As the reducing agent, for example, aluminum hydrides such as lithium aluminum hydride and the like; and borohydride such as diborane and sodium borohydride and the like can be used.

In a case where sodium borohydride is used as the reducing agent, the reaction is preferably carried out in the presence of a Lewis acid such as boron trifluoride diethyl etherate and the like.

The reducing agent is used in an amount of at least 0.5 mol and preferably in an amount of 1–10 mol, per mol of the compound [6a].

The Lewis acid is used at least in an equimolar amount to the reducing agent, and preferably in an amount of 1–20 mol per mol of the reducing agent.

This reaction is carried out at a temperature of usually −50° C. to +200° C. and preferably 0° C. to +110° C., for a period of 10 minutes to 20 hours.

Production Process 3

A compound of general formula [7a] is reacted with a compound of general formula [5] in the presence or absence of a base, whereby a compound of general formula [1a] can be obtained.

The solvents which can be used in this reaction include, for example, water; halogenated hydrocarbons such as methylene chloride, chloroform and the like; aromatic hydrocarbons such as benzene, toluene, xylene and the like; ethers such as tetrahydrofuran, dioxane and the like; alcohols such as methanol, ethanol and the like; nitriles such as acetonitrile and the like; amides such as N,N-dimethylformamide and the like; sulfoxides such as dimethyl sulfoxide and the like; etc. These solvents can be used in the form of a mixture, if desired.

As the base which can be used as occasion demands, for example, organic and inorganic bases such as triethylamine, diisopropylethylamine, 1,8-diazabicyclo[5.4.0]undec-7-ene, pyridine, potassium tert-butoxide, sodium carbonate, potassium carbonate, sodium hydride and the like can be referred to.

The base is used at least in an equimolar amount to the compound of general formula [7a], and preferably in an amount of 1–20 mol per mol of the compound [7a].

If desired, this reaction can be carried out in the presence of a catalyst. The catalysts usable are, for example, potassium iodide, sodium iodide, and the like.

The catalyst is used in an amount of 0.01–10 mol and preferably 0.1–1 mol, per mol of the compound [7a].

The compound of general formula [5] at least in an equimolar amount to compound [7a], and preferably in an amount of 1–20 mol per mol of compound [7a].

This reaction is carried out at a temperature of usually 0° C. to +200° C. and preferably +20° C. to +150° C., for a period of 10 minutes to 20 hours.

It is also possible, if desired, to use the reagents and bases used in the above-mentioned Production Processes 1–3 as a solvent according to the nature thereof.

Production Process 4

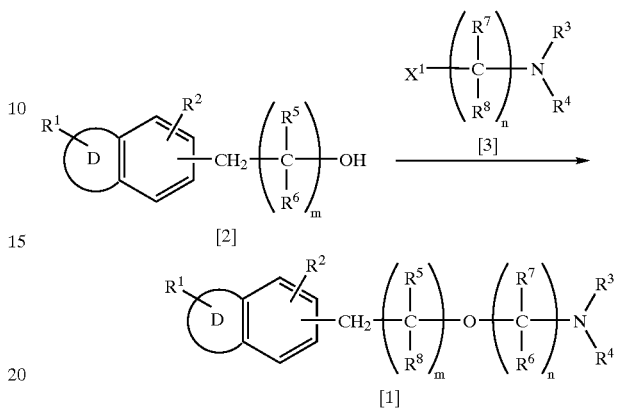

Production Process 5

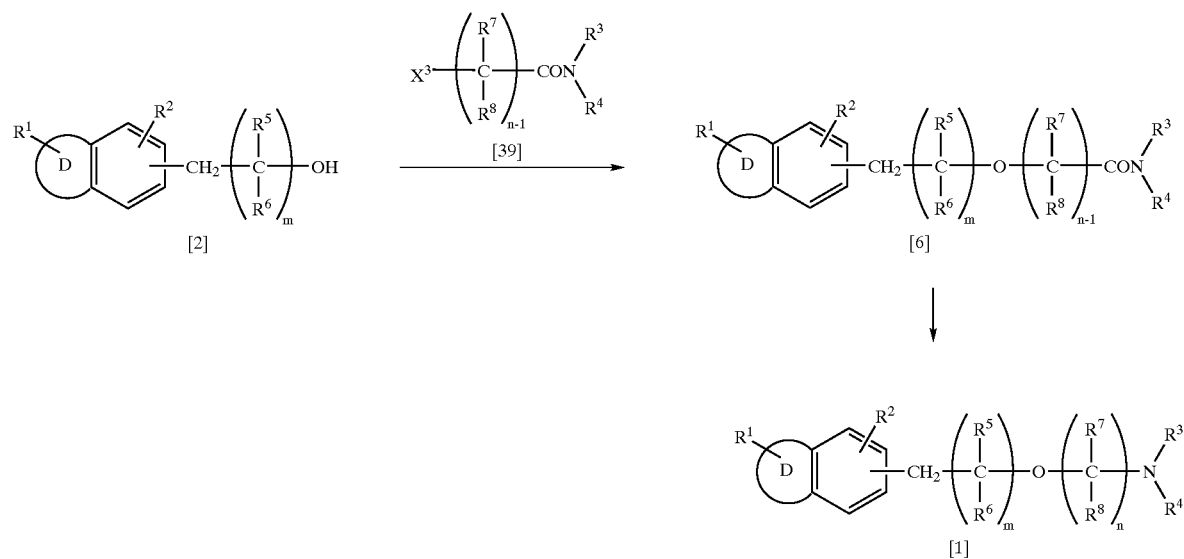

Production Process 6

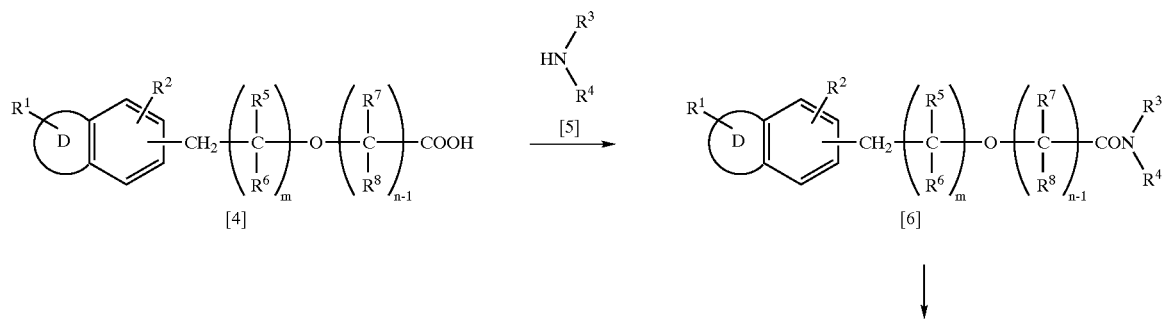

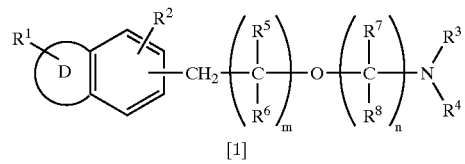

Production Process 7

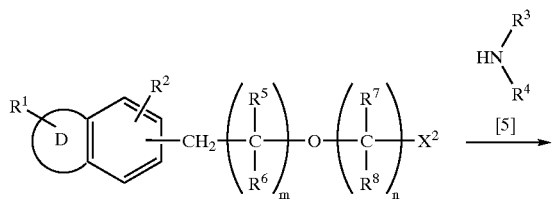

Production Process 8

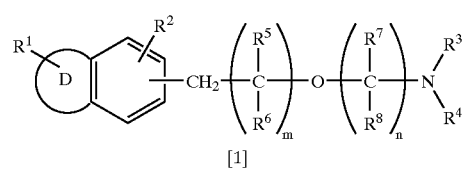

Production Process 9

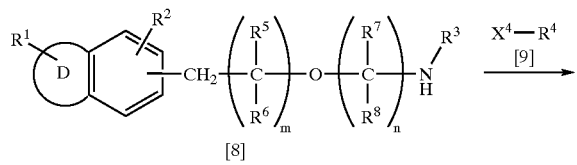

Production Process 10

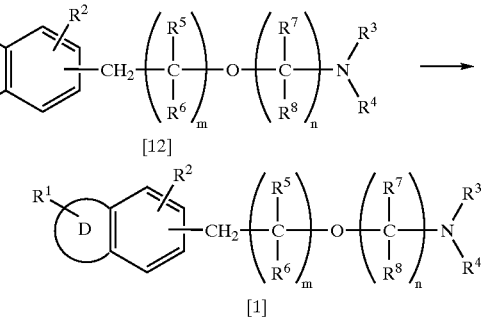

wherein $R^1$, $R^2$, $R^3$, $R^4$, $R^5$, $R^6$, $R^7$, $R^8$, m and n are as defined above; $R^9$ represents a hydrogen atom or an unsubstituted or substituted alkyl or cycloalkyl group; one of $R^{10}$ and $R^{11}$ represents a hydrogen atom or a substituent necessary for formation of a ring in the 5- or 6-membered heterocyclic ring or hydrocarbon ring; and $X^1$, $X^2$, $X^3$ and $X^4$ independently represent a removing group.

The substituent necessary for formation of a ring in the 5- or 6-membered heterocyclic or hydrocarbon ring includes, for example, halogen atom, an unsubstituted or substituted alkyl, alkenyl, alkynyl, alkoxy, alkylthio, alkenyloxy, amino, alkylsulfonyl, arylsulfonyl, carbamoyl or acyl group, an unprotected or protected amino, hydroxyl or mercapto group, carboxyl group, and nitro group. As the removing group, for example, halogen atom, lower alkylsulfonyloxy group, arylsulfonyloxy group and the like can be referred to.

Next, the steps of the processes will be explained below.

Production Process 4

A compound of general formula [2] is reacted with a compound of general formula [3] in the presence of a base, whereby the compound of general formula [1] can be produced.

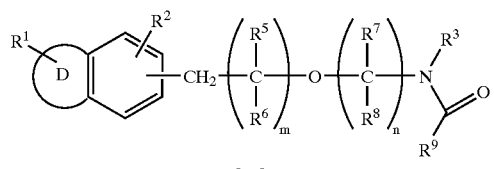

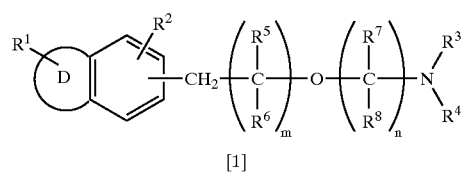

This reaction is carried out according to a method known per se, such as the same method as Production Process 1.

Production Process 5

(1) A compound of general formula [2] is reacted with a compound of general formula [39] in the presence of a base, whereby the compound of general formula [6] can be produced.

This reaction is carried out according to a method known per se, such as the method described in Shin Jikken Kagaku Koza, Vol. 14, [I], edited by Chemical Society of Japan, Pages 567–611 (1977, Maruzen), or any analogous method.

As the base, for example, organic or inorganic bases such as triethylamine, diisopropylethylamine, 1,8-diazabicyclo [5.4.0 undec-7-ene, pyridine, sodium hydroxide, potassium hydroxide, potassium carbonate, sodium hydroxide, metallic sodium, lithium diisopropylamide, n-butyllithium, potassium tert-butoxide and the like can be referred to.

The solvents which can be used in this reaction include, for example, water; halogenated hydrocarbons such as methylene chloride, chloroform and the like; ethers such as tetrahydrofuran, dioxane and the like; aromatic hydrocarbons such as benzene, toluene, xylene and the like; sulfoxides such as dimethyl sulfoxide and the like; amides such as N,N-dimethylformamide and the like; esters such as ethyl acetate and the like; ketones such as acetone, methyl ethyl ketone and the like; nitriles such as acetonitrile and the like; tertiary alcohols such as tert-butanol and the like; hetero-aromatic compounds such as pyridine and the like; etc. These solvents can be used in the form of a mixture, if desired.

Each of the compound of general formula [39] and the base is used at least in an equimolar amount to the compound of general formula [2], and preferably in an amount of 1–20 mol per mol of compound [2].

This reaction is carried out usually at −50° C. to +200° C. and preferably at 0° C. to +150° C., for a period of 10 minutes to 20 hours.

(2) A compound of general formula [6] is subjected to conventional reduction reaction, whereby the compound of general formula [1] can be obtained.

This reaction can be carried out according to a method known per se, such as the same method as Production Process 2 (2).

Production Process 6

(1) A compound of general formula [4] or a reactive derivative thereof is reacted with a compound of general formula [5], whereby a compound of general formula [6] can be obtained.

This reaction is carried out according to a method known per se, such as the same method as Production Process 2 (1).

(2) A compound of general formula [6] is subjected to conventional reduction reaction, whereby a compound of general formula [1] can be obtained.

This reaction is carried out according to a method known per se, such as the same method as Production Process 2 (2).

Production Process 7

A compound of general formula [7] is reacted with a compound of general formula [5] in the presence or absence of a base, whereby a compound of general formula [1] can be obtained.

This reaction is carried out according to a method well known in itself, such as the same method as Production Process 3.

Production Process 8

A compound of general formula [8] is reacted with a compound of general formula [9] in the presence or absence of a base, whereby a compound of general formula [1] can be obtained.

This reaction is carried out according to a method known per se, such as the same method as Production Process 3.

Production Process 9

(1) A compound of general formula [8] is reacted with a compound of general formula [10] or a reactive derivative thereof, whereby the compound of general formula [11] can be obtained.

This reaction is carried out according to a method known per se, such as the same method as Production Process 2 (1).

(2) A compound of general formula [11] is subjected to a conventional reduction reaction, whereby the compound of general formula [1] can be obtained.

This reaction is carried out according to a method known per se, such as the same method as Production process 2 (2).

Production Process 10

A compound of general formula [12] is subjected to a conventional ring-closing reaction, whereby the compound of general formula [1] can be obtained.

This reaction is carried out according to a method known per se, such as the method described in "The Chemistry of Heterocyclic Compounds", Pages 16–80 (1988, Kodansha), Shin Jikken Kagaku Koza, Vol. 14, [II], edited by Chemical Society of Japan, Pages 788–796 (1977, Maruzen), and Shin Jikken Kagaku Koza, Vol. 14, [IV], edited by Chemical Society of Japan, Pages 1879–2406 (1977, Maruzen), or any analogous method.

Hereunder, the process is explained with reference to several specific examples.

(1) In cases where $R^{10}$ is an amino group and $R^{11}$ is an amino, hydroxyl or mercapto group, a compound of general formula [12] is reacted with a carboxylic acid or a compound equivalent to carboxylic acid, whereby a benzoazole derivative represented by general formula [1] can be obtained.

The solvents which can be used in this reaction include, for example, water; ethers such as tetrahydrofuran, dioxane and the like; aromatic hydrocarbons such as benzene, toluene, xylene and the like; sulfoxides such as dimethyl sulfoxide and the like; alcohols such as methanol, ethanol, isopropanol and the like; hetero-aromatic compounds such as pyridine and the like; etc. These solvents can be used in the form of a mixture, if desired.

As the carboxylic acid, formic acid, acetic acid, propionic acid, hydroxyacetic acid, phenylacetic acid and the like can be referred to.

The compound equivalent to carboxylic acid includes acid anhydrides such as acetic anhydride and the like; acid chlorides such as acetyl chloride, ethyl chloroacetate and the like; ortho esters such as ethyl orthoformate and the like; amidines such as acetoamidine and the like; and nitrites such as acetonitrile and the like.

The carboxylic acid or the compound equivalent to carboxylic acid are used at least in an equimolar amount to the compound of general formula [12], and preferably in an amount of 1–20 mol per mol of compound [12].

This reaction is usually carried out at a temperature of −50° C. to +200° C. and preferably at 0° C. to +200° C., for a period of 10 minutes to 20 hours.

(2) In case where both $R^{10}$ and $R^{11}$ are an amino group, compound [12] is reacted with an α-carbonylcarbonyl derivative, whereby a quinoxalne derivative represented by general formula [1] can be obtained.

The solvents which can be used in this reaction include, for example, water; ethers such as tetrahydrofuran, dioxane and the like; aromatic hydrocarbons such as benzene, toluene, xylene and the like; sulfoxides such as dimethyl sulfoxide and the like; alcohols such as methanol, ethanol, isopropanol and the like; hetero-aromatic compounds such as pyridine and the like; etc. These solvents can be used in the form of a mixture, if desired.

As the α-carbonylcarbonyl derivative, glyoxal, ethyl glyoxalate, pyruvic aldehyde, 1-phenyl-1,2-propanedione and the like can be referred to.

The α-carbonylcarbonyl derivative is used at least in an equimolar amount to the compound of general formula [12], and preferably in an amount of 1–20 mol per mol of compound [12].

This reaction is usually carried out at −50° C. to +200° C. and preferably at 0° C. to +200° C., for a period of 10 minutes to 20 hours.

(3) In case where $R^{10}$ is an alkylcarbonyl group and $R^{11}$ is a hydroxyl or mercapto group, a compound of general formula [12] is reacted with an ester or a reactive carboxylic acid derivative in the presence of a base, whereby a chromone or thiochromone derivative represented by general formula [1] can be obtained.

The solvents which can be used in this reaction include, for example, ethers such as tetrahydrofuran, dioxane and the like; aromatic hydrocarbons such as benzene, toluene, xylene and the like; amides such as N,N-dimethylformamide and the like; sulfoxides such as dimethyl sulfoxide and the like; alcohols such as methanol, ethanol, isopropanol and the like; and hetero-aromatic compounds such as pyridine and the like; etc. These solvents can be used in the form of a mixture, if desired.

As the ester, ethyl formate, methyl formate, ethyl acetate, ethyl benzoate and the like can be referred to.

As the reactive carboxylic acid derivative, acid anhydrides such as acetic anhydride and the like, acid chlorides such as acetyl chloride and the like, ortho esters such as ethyl orthoformate and the like, acetals such as N,N-dimethylformamide dimethyl acetals and the like, etc. can be referred to.

Each of the ester, the reactive carboxylic acid derivative and the base is used at least in an equimolar amount to the compound of general formula [12], and preferably in an amount of 1–20 mol per mol of compound [12].

This reaction is usually carried out at a temperature of −50° C. to +200° C. and preferably at 0° C. to +130° C., for a period of 10 minutes to 20 hours.

(4) In case where $R^{10}$ is an alkyl group of which the β and γ positions are substituted with carboxyl group, a compound of general formula [12] is subjected to a ring-forming reaction in the presence of an acid, whereby a 5- or 6-membered hydrocarbon ring derivative represented by general formula [1] can be obtained.

The solvents which can be used in this reaction include, for example, aromatic hydrocarbons such as benzene, toluene, xylene and the like; halogenated hydrocarbons such as methylene chloride, chloroform and the like; etc. These solvents can be used in the form of a mixture, if desired.

The acids which can be used include mineral acids such as phosphoric acid, polyphosphoric acid, sulfuric acid, hydrofluoric acid and the like; Lewis acids such as phosphorus pentachloride, aluminum chloride, zinc chloride, tin chloride and the like; etc.

The acid is used at least in an equimolar amount to the compound of general formula [12], and preferably in an amount of 1–20 mol per mol of compound [12].

This reaction is usually carried out at a temperature of −50° C. to +200° C. and preferably at 0° C. to +130° C., for a period of 10 minutes to 20 hours.

If desired, it is also possible to use the reagents used in the above-mentioned production processes 1–10 as a solvent, according to the nature thereof.

In the above-mentioned Production Processes 1–10, it is also possible to use the compounds of general formulas [2], [2a], [3], [3a], [4], [4a], [5], [6], [6a], [7], [7a], [8], [9], [10], [11], [12] and [39] in the form of a salt, if desired. As said salt, the same salts as mentioned in the paragraph of salts of compound [1] can be used.

In case where the compounds of general formulas [2], [2a], [3], [3a], [4], [4a], [5], [6], [6a], [7], [7a], [8], [9], [10], [11], [12] and [39] have an isomer such as optical isomer, geometrical isomer, tautomer and the like, all these isomers are usable in the present invention. Further, all the hydrated products and solvated products and all the crystal forms can also be used in the present invention.

In cases where the compounds of general formulas [1], [1a], [2], [2a], [3], [3a], [4], [4a], [5], [6], [6a], [7], [7a], [8], [9], [10], [11], [12] and [39] have a hydroxyl group, an amino group or a carboxyl group, those hydroxyl, amino and carboxyl groups can be protected previously with a conventional protecting group. Such a protecting group can be eliminated after the reaction according to a method known per se, as occasion demands.

Further, it is possible to convert an N-alkoxyalkyl-N,N-dialkylamine derivative of general formula [1] and [1a] into the other N-alkoxyalkyl-N,N-dialkylamine derivative represented by general formula [1] or a salt thereof, by an appropriate combination of well known treatments such as oxidation, reduction, alkylation, halogenation, sulfonylation, substitution, dehydration, hydrolysis, etc.

The N-alkoxyalkyl-N,N-dialkylamine derivative of general formula [1] or a salt thereof thus obtained can be isolated and purified by conventional methods such as extraction, crystallization, distillation, column chromatography, etc.

Next, the processes for producing the compounds of general formula [2a], [4a], [7a], [2], [4], [7], [8] and [12] which are starting materials for production of the compounds of the present invention will be explained.

The compound of general formula [2a] can be produced according to methods known per se or an appropriate combination thereof. For example, compound [2a] can be produced by the following Production Process A.

Production Process A

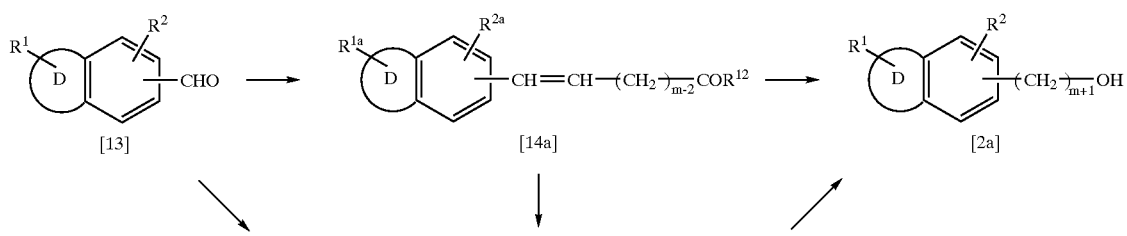

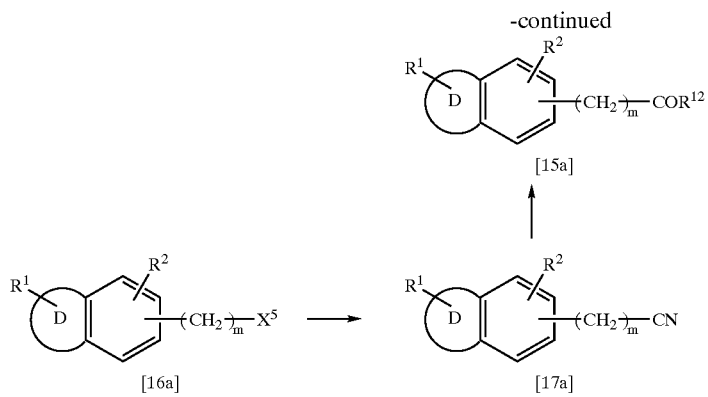

wherein $R^1$, $R^2$ and m are as defined above; $R^{1a}$ represents the same group as $R^1$ except alkenyl group; $R^{2a}$ represents the same group as $R^2$ except alkenyl group; $R^{12}$ represents hydrogen atom, hydroxyl group or lower alkoxy group; and $X^5$ represents a removing group.

As the removing group, for example, halogen atom, lower alkylsulfonyloxy group, arylsulfonyloxy group and the like can be referred to.

(A-1) A compound of general formula [13] is subjected to a conventional carbon chain-extending reaction, whereby a compound of general formula [14a] can be obtained.

This reaction can be carried out according to the method described in, for example, Jikken Kagaku Koza, Vol. 22, edited by Chemical Society of Japan, Pages 54–68 (1992, Maruzen) or any analogous method. As specific examples of the carbon chain-extending reaction, Wittig reaction, Wittig-Horner reaction and the like can be referred to.

(A-2) A compound of general formula [14a] is subjected to a conventional reduction reaction, whereby a compound of general formula [2a] can be obtained.

This reduction can be carried out according to the method described in, for example, Shin Jikken Kagaku Koza, Vol. 15, [II], edited by Chemical Society of Japan, Pages 29–244 (1977, Maruzen) or any analogous method.

(A-3) A compound of general formula [14a] is subjected to a conventional catalytic hydrogenation, whereby a compound of general formula [15a] can be obtained.

This hydrogenation can be carried out according to a method known per se, such as the method described in Shin Jikken Kagaku Koza, Vol. 15, [II], edited by Chemical Society of Japan, Pages 333–448 (1977, Maruzen), or any analogous method.

(A-4) As an alternative process for producing a compound of general formula [15a], a process of subjecting a compound of general formula [13] to a conventional carbon chain-extending reaction can also be referred to.

This reaction can be carried out according to a method known per se, such as the method described in Jikken Kagaku Koza, Vol. 21, edited by Chemical Society of Japan, Pages 124–133 (1992, Maruzen), or any analogous method.

As a concrete example of the carbon chain-lengthening reaction, Wittig reaction and the like can be referred to.

(A-5) A compound of general formula [16a] is subjected to a conventional cyanidation reaction, whereby a compound of general formula [17a] can be obtained.

This reaction can be carried out according to a method known per se, such as the method described in Shin Jikken Kagaku Koza, Vol. 14, [III], edited by Chemical Society of Japan, Pages 1428–1484 (1977, Maruzen), or any analogous method.

(A-6) A compound of general formula [17a] is subjected to a conventional hydrolysis, a conventional ester-forming alcoholysis or a conventional reduction reaction using a metal hydride such as diisobutyl aluminum hydride or the like, whereby a compound of general formula [15a] can be obtained.

These reactions can be carried out according to methods known per se, such as those described in Jikken Kagaku Koza, Vol. 22, edited by Chemical Society of Japan, Pages 1–83 (1992, Maruzen) and Jikken Kagaku Koza, Vol. 21, edited by Chemical Society of Japan, Pages 72–97 (1992, Maruzen), or any analogous methods.

(A-7) A compound of general formula [15a] is subjected to a conventional reduction reaction, whereby a compound of general formula [2a] can be obtained.

This reduction can be carried out according to a method known per se, such as the method described in Shin Jikken Kagaku Koza, Vol. 15, [II], edited by Chemical Society of Japan, Pages 29–244 (1977, Maruzen) or any analogous method.

Further, a compound of general formula [2a] having a longer carbon chain can be produced by using a compound of general formula [15a] in which $R^{12}$ is a hydrogen atom as a starting material, and repeating the reactions of (A-1), (A-3) and (A-4).

The compounds of general formulas [4a] and [7a] can be produced according to methods known per se or an appropriate combination of such methods, such as the Production Process B shown below:

Production Process B

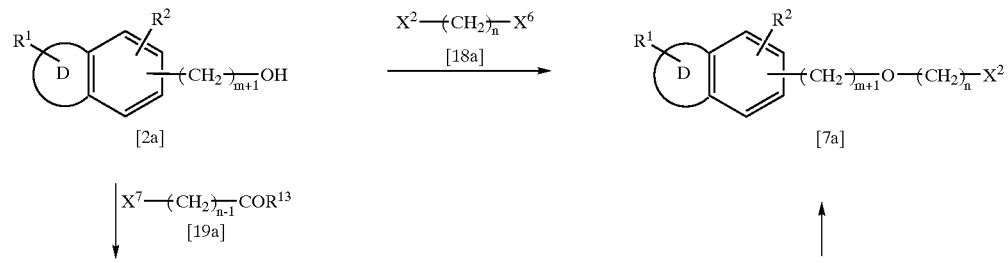

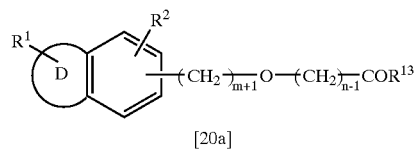

[20a]

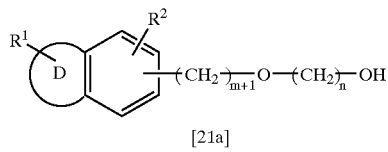

[21a]

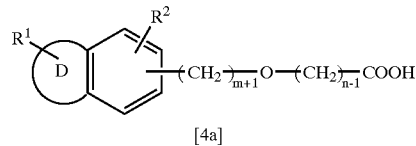

[4a]

wherein $R^1$, $R^2$, $X^2$, m and n are as defined above; $R^{13}$ represents a lower alkoxy, dialkylamino or cyclic amino group; and $X^6$ and $X^7$ independently represent a halogen atom.

The term "cyclic amino group" means a 5-, 6- or 7-membered ring cyclic amino group which contains one nitrogen atom as a hetero-atom constituting the ring and may additionally contain one or more oxygen atom or sulfur atom, such as pyrrolidinyl, piperidinyl, morpholyl, thiomorpholyl and the like.

(B-1) A compound of general formula [2a] is reacted with a compound of general formula [18a], whereby a compound of general formula [7a] can be obtained.

This reaction can be carried out according to a method known per se, such as the same process as in Production Process 1.

(B-2) A compound of general formula [2a] is reacted with a compound of general formula [19a] in the presence of a base, whereby a compound of general formula [20a] can be obtained.

This reaction can be carried out according to a method known per se, such as the method described in Shin Jikken Kagaku Koza, Vol. 14, [I], edited by Chemical Society of Japan, Pages 567–611 (1977, Maruzen), or any analogous method.

The base includes, for example, organic and inorganic bases such as triethylamine, diisopropylethylamine, 1,8-diazabicyclo[5.4.0]undec-7-ene, pyridine, sodium hydroxide, potassium hydroxide, potassium carbonate, sodium hydride, metallic sodium, lithium diisopropylamide, n-butyllithium, potassium tert-butoxide and the like.

The solvents which can be used in this reaction include, for example, water; halogenated hydrocarbons such as methylene chloride, chloroform and the like; ethers such as tetrahydrofuran, dioxane and the like; aromatic hydrocarbons such as benzene, toluene, xylene and the like; sulfoxides such as dimethyl sulfoxide and the like; amides such as N,N-dimethylformamide and the like; esters such as ethyl acetate and the like; ketones such as acetone, methyl ethyl ketone and the like; nitrites such as acetonitrile and the like; tertiary alcohols such as tert-butanol and the like; heteroaromatic compounds such as pyridine and the like; etc. These solvents can be used in the form of a mixture, if desired.

The compound of general formula [19a] and the base are used each in an equimolar amount to the compound of general formula [2a], and preferably in an amount of 1–20 mol per mol of compound [2a].

This reaction is usually carried out at a temperature of −50° C. to +200° C. and preferably at 0° C. to +150° C., for a period of 10 minutes to 20 hours.

(B-3) A compound of general formula [20a] is subjected to conventional hydrolysis of ester or amide, whereby a compound of general formula [4a] can be obtained.

This reaction can be carried out according to a method known per se, such as the method described in "Protective Groups in Organic Syntheses" (Theodra W. Green, 1981, John Wiley & Sons, Inc.) or any analogous method.

(B-4) A compound of general formula [4a] or a compound of general formula [20a] is subjected to conventional reduction reaction, whereby a compound of general formula [21a] can be obtained.

This reduction is carried out according to a method known per se, such as the method described in Shin Jikken Kagaku Koza, Vol. 15, Pages 26–244 (1977, Maruzen) or any analogous method.

(B-5) A compound of general formula [21a] is treated with a halogenating agent or a sulfonylating agent in the presence or absence of a base, whereby a compound of general formula [7a] can be obtained.

The solvents which can be used in this reaction include, for example, halogenated hydrocarbons such as methylene chloride, chloroform and the like; ethers such as tetrahydrofuran, dioxane and the like; aromatic hydrocarbons such as benzene, toluene, xylene and the like; sulfoxides such as dimethyl sulfoxide and the like; amides such as N,N-dimethylformamide and the like; esters such as ethyl acetate and the like; nitriles such as acetonitrile and the like; etc. These solvents can be used in the form of a mixture, if desired.

The bases which may be used as occasion demands, for example, organic and inorganic bases such as triethylamine, diisopropylethylamine, 1,8-diazabicyclo[5.4.0]undec-7-ene, pyridine, potassium tert-butoxide, sodium carbonate, potassium carbonate, sodium hydride and the like.

As the halogenating agent, for example, phosphorus oxychloride, phosphorus oxybromide, phosphorus trichloride, phosphorus pentachloride, thionyl chloride and the like can be referred to.

As the sulfonylating agent, for example, methanesulfonyl chloride, p-toluenesulfonyl chloride and the like can be referred to.

The halogenating agent and sulfonylating agent are both used at least in an equimolar amount to the compound of general formula [21a], and preferably in an amount of 1–2 mol per mol of compound [21a].

This reaction is carried out usually at a temperature of −50° C. to +200° C. and preferably at 0° C. to +50° C., for a period of 1–10 minutes to 30 hours.

In the above-mentioned Production Processes A and B, the compounds of general formulas [13], [14a], [15a], [16a], [17a], [2a], [4a], [19a], [20a] and [21a] can be used in the form of a salt, too, if desired. As the salt, the same salts as mentioned in the paragraph of the compound of general formula [1] can be referred to.

In the above-mentioned Production Processes A and B, the compounds of general formulas [13], [14a], [15a], [16a], [17a], [2a], [4a], [19a], [20a] and [21a] may have isomers such as optical isomer, geometrical isomer, tautomer, etc. In such a case, all these isomers can be used in the present invention. Further, hydrated products and solvated products thereof and all the crystal forms thereof can also be used in the invention.

Further, some of the compounds [13], [14a], [15a], [16a], [17a], [2a], [4a], [19a], [20a] and [21a] may have a hydroxyl group, an amino group or a carboxyl group. In such a case, it is possible to protect these groups with conventional protecting groups previously and to remove the protecting groups after the reaction according to a method known per se.

The compound of general formula [2] can be produced according to a method known per se or an appropriate combination of such methods. For example, it can be produced according to the following Production Process C.

Production Process C

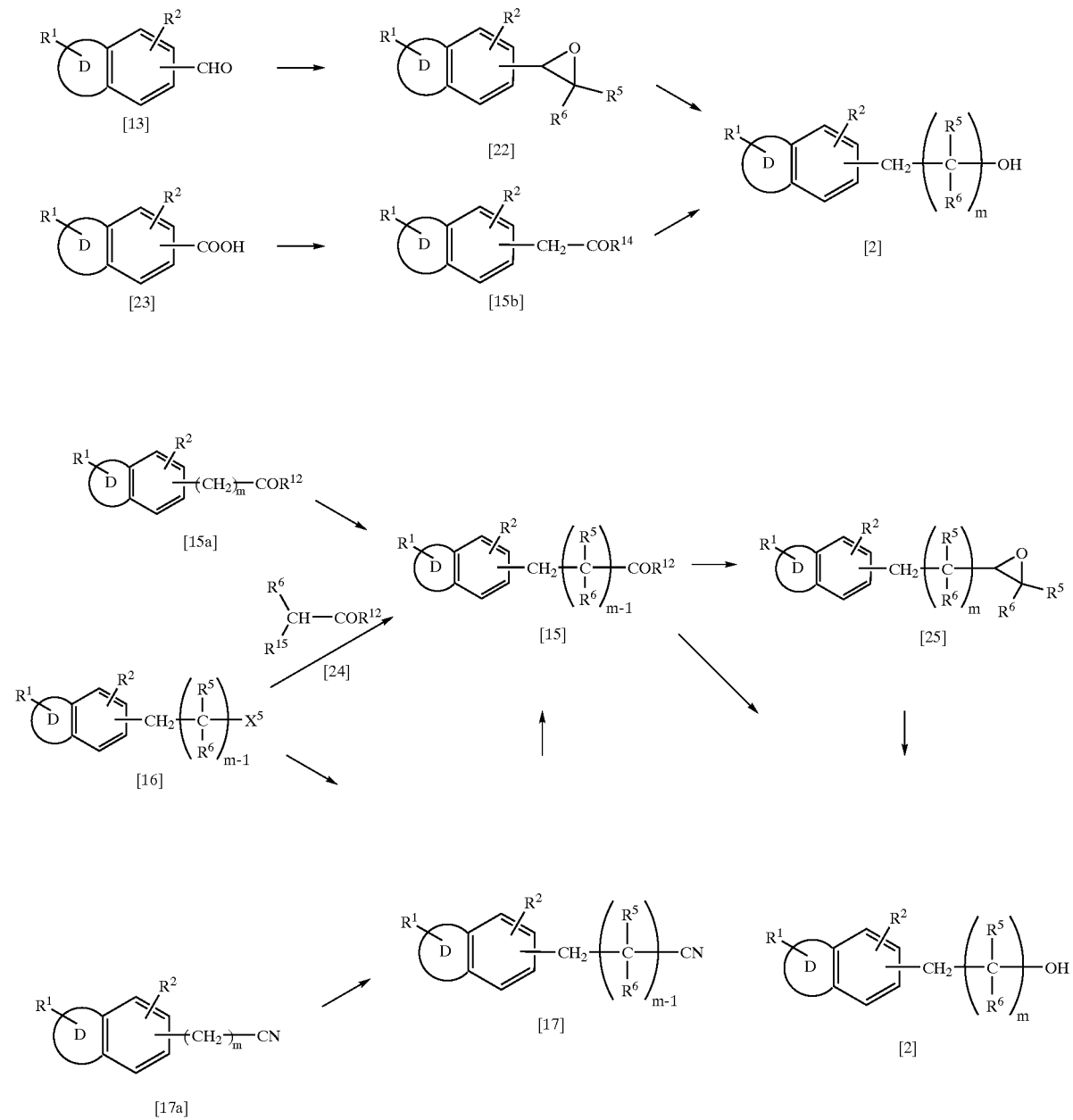

-continued

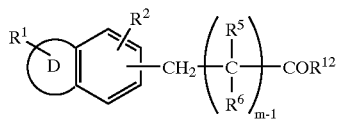
[15]

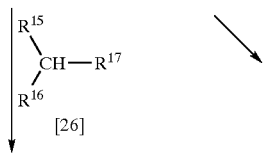
[26]

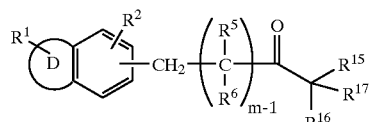 → 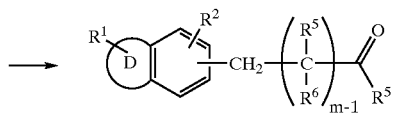 → 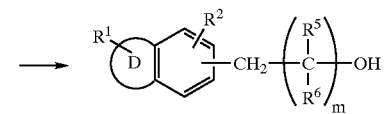
[27]                  [28]                  [2]

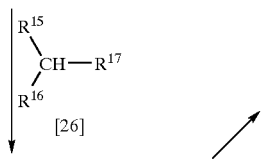
[26]

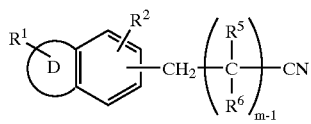
[17]

wherein $R^1$, $R^2$, $R^5$, $R^6$, $R^{12}$, m and $X^5$ are as defined above; $R^{14}$ represents a lower alkoxy group; $R^{15}$ represents a hydrogen atom, a lower alkyl group or a lower alkoxycarbonyl group; $R^{16}$ represents a cyano group or a lower alkoxycarbonyl group; and $R^{17}$ represents a hydrogen atom, a cyano group, a carboxyl group or a lower alkoxycarbonyl group.

(C-1) A compound of general formula [13] is subjected to a conventional epoxidation reaction, whereby a compound of general formula [22] can be obtained.

This epoxidation reaction can be carried out according to a method known per se, such as the method described in Shin Jikken Kagaku Koza, Vol. 14, [I], edited by Chemical Society of Japan, Pages 593–607 (1977, Maruzen), or any analogous method.

(C-2) A compound of general formula [22] is subjected to a conventional reduction reaction, whereby a compound of general formula [2] can be obtained.

This reaction can be carried out according to a method known per se, such as the method described in Shin Jikken Kagaku Koza, Vol. 15, [II], edited by Chemical Society of Japan, Pages 227–228 (1977, Maruzen), or any analogous method.

(C-3) A compound of general formula [23] is subjected to conventional carbon chain-extending reaction, whereby a compound of general formula [15a] can be obtained.

This reaction can be carried out according to a method known per se, such as the method described in Shin Jikken Kagaku Koza, Vol. 14, [II], edited by Chemical Society of Japan, Pages 1031–1032 (1977, Maruzen), or any analogous method. As a specific example of the carbon chain-extending reaction, Arndt-Eistert reaction or the like can be referred to.

(C-4) A compound of general formula [15b] is subjected to a conventional reduction reaction or addition of organo-metallic compound, whereby a compound of general formula [2] can be produced.

This reaction can be carried out according to a method known per se, such as the method described in Shin Jikken Kagaku Koza, Vol. 14, [I], edited by Chemical Society of Japan, Pages 474–477 and 512–520 (1977, Maruzen), or any analogous method.

(C-5) A compound of general formula [15a] can be converted to a compound of general formula [15] by subjecting compound [15a] to a conventional alkylation reaction.

This alkylation reaction can be carried out according to a method known per se, such as the method described in Shin Jikken Kagaku Koza, Vol. 14, [II], edited by Chemical Society of Japan, Pages 637–1062 (1977, Maruzen), or any analogous method.

(C-6) As an alternative process thereof, a process of reacting a compound [16] with a compound of general formula [24] can be referred to. By this process, a compound of general formula [15] can be obtained.

This reaction can be carried out according to a method known per se, such as the method described in Shin Jikken Kagaku Koza, Vol. 14, [II], edited by Chemical Society of Japan, Pages 637–1062 (1977, Maruzen), or any analogous method.

It is possible, in this reaction, to carry out a hydrolysis and a decarboxylation reaction after completion of the reaction by a method known per se, as occasion demands.

(C-7) A compound of general formula [16] is subjected to a conventional cyanidation reaction, whereby a compound of general formula [17] can be obtained.

This reaction can be carried out according to a method known per se, such as the same method as (A-5).

(C-8) As an alternative process thereof, a process of subjecting a compound of general formula [17a] to a conventional alkylation reaction can be referred to. By this process, the compound [17a] can be converted to a compound of general formula [17].

This alkylation reaction can be carried out according to a method known per se, such as the method described in Shin Jikken Kagaku Koza, Vol. 14, [III], edited by Chemical Society of Japan, Pages 1447–1448 (1977, Maruzen), or any analogous method.

(C-9) A compound of general formula [17] is subjected to a conventional hydrolysis, an ester-forming alcoholysis or a reduction using a metal hydride such as diisobutyl aluminum hydride or the like, whereby a compound of general formula [15] can be obtained.

This reaction can be carried out according to a method known per se, such as the same method as (A-6).

(C-10) A compound of general formula [15] wherein $R^{12}$ is a hydrogen atom is subjected to a conventional epoxidation reaction, whereby a compound of general formula [25] can be produced.

This reaction can be carried out according to a method known per se, such as the same method as (C-1).

(C-11) A compound of general formula [25] is subjected to a conventional reduction or a ring-opening reaction using an organometallic compound, whereby a compound of general formula [2] can be obtained.

This reaction can be carried out according to a method known per se, such as the method described in Shin Jikken Kagaku Koza, Vol. 15, [I], edited by Chemical Society of Japan, Pages 478–481 and 524–529 (1977, Maruzen), or any analogous method.

(C-12) A compound of general formula [15] is subjected to a conventional reduction reaction or addition of organometallic compound, whereby a compound of general formula [2] can be obtained.

This reaction can be carried out according to a method known per se, such as the same method as (C-4).

(C-13) A compound of general formula [15] wherein $R^{12}$ is a hydroxyl group or a lower alkoxy group can be converted to a compound of general formula [27] through a condensation reaction with a compound of general formula [26]. In case where $R^{12}$ is a hydroxyl group, the compound [15] is converted to a reactive derivative thereof prior to the condensation reaction.

This reaction can be carried out according to a method known per se, such as the method described in Shin Jikken Kagaku Koza, Vol. 15, [II], edited by Chemical Society of Japan, Pages 767–775 (1977, Maruzen), or any analogous method.

(C-14) A compound of general formula [17] is subjected to a condensation reaction with a compound of general formula [26], whereby a compound of general formula [27] can be obtained.

This reaction can be carried out according to a method known per se, such as the method described in Shin Jikken Kagaku Koza, Vol. 15, [II], edited by Chemical Society of Japan, Pages 808–811 (1977, Maruzen), or any analogous method.

(C-15) A compound of general formula [27] is subjected to a conventional hydrolysis followed by a decarboxylation reaction, whereby a compound of general formula [28] can be obtained.

This reaction is carried out according to a method known per se, such as the method described in Shin Jikken Kagaku Koza, Vol. 15, [II], edited by Chemical Society of Japan, Pages 808–811 (1977, Maruzen), or any analogous method.

(C-16) As an alternative process thereof, a process of subjecting a compound of general formula [15] wherein $R^{12}$ is a hydroxyl group or a lower alkoxy group to a conventional reduction reaction or an addition of organometallic compound can be referred to. By this process, a compound of general formula [28] can be obtained.

This reaction is carried out according to a method known per se, such as the method described in Shin Jikken Kagaku Koza, Vol. 15, [II], edited by Chemical Society of Japan, Pages 656–662 and 775–792 (1977, Maruzen), or any analogous method.

(C-17) A compound of general formula [17] is subjected to a conventional reduction reaction or an addition of organometallic compound, whereby a compound of general formula [28] can be obtained.

This reaction is carried out according to a method known per se, such as the method described in Shin Jikken Kagaku Koza, Vol. 15, [II], edited by Chemical Society of Japan, Pages 652–656 and 808–810 (1977, Maruzen), or any analogous method.

(C-18) A compound of general formula [28] is subjected to a conventional reduction reaction or an addition of organometallic compound, whereby a compound of general formula [2] can be obtained.

This reaction is carried out according to a method known per se, such as the same method as (C-4).

The compounds of general formulas [4] and [7] can be produced according to methods known per se or an appropriate combination thereof. For examples, these compounds can be produced by Production Process D mentioned below.

Production Process D

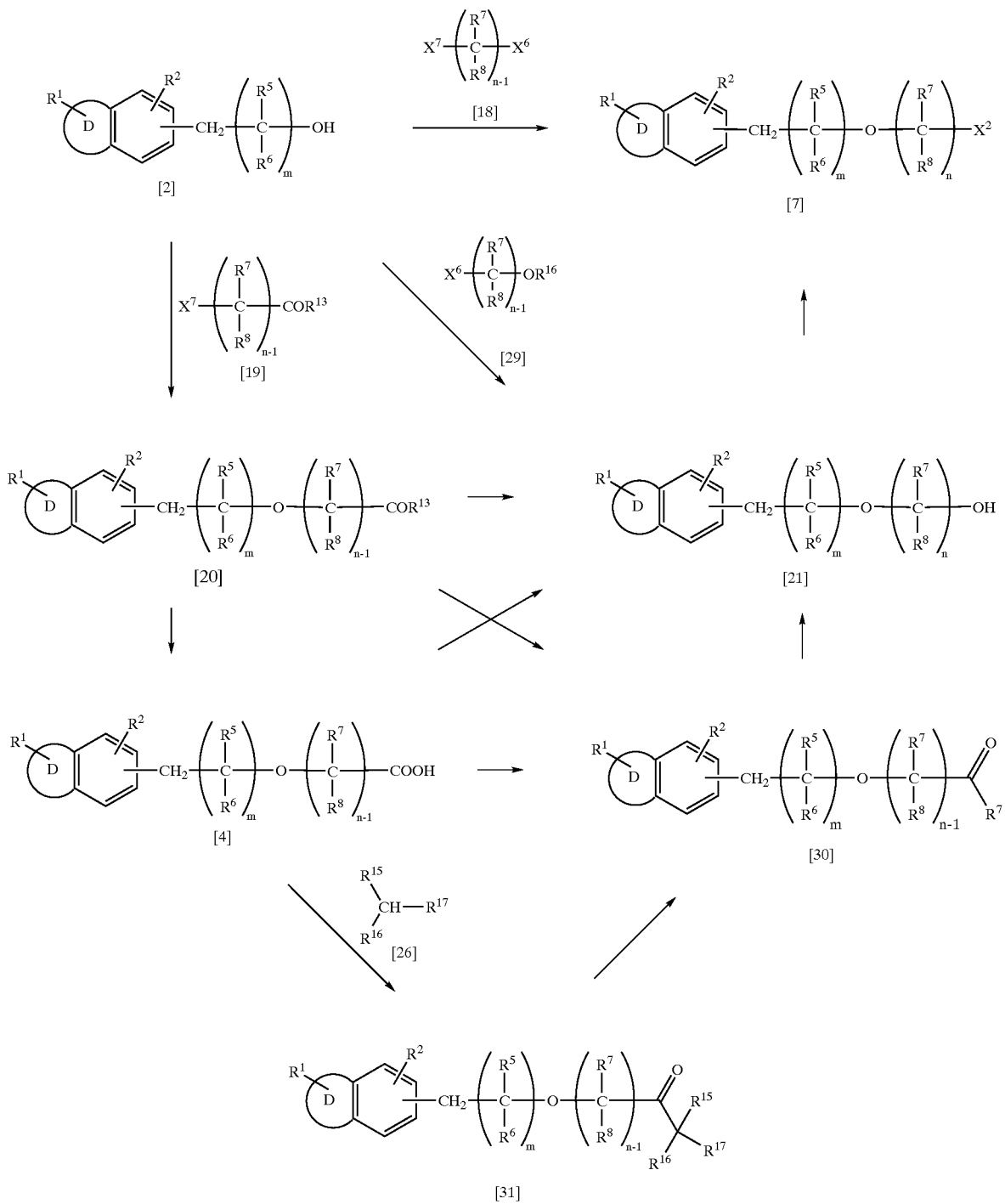

wherein $R^1$, $R^2$, $R^5$, $R^6$, $R^7$, $R^8$, $R^{13}$, $R^{15}$, $R^{16}$, $R^{17}$, $X^2$, $X^6$, $X^7$, m and n are as defined above; $R^{18}$ represents a protecting group for hydroxyl group which is unreactive under an alkaline condition; and $X^8$ represents a halogen atom.

Examples of the protecting group which is not unreactive under basic condition include lower alkyl groups such as tert-butyl and the like; lower alkenyl groups such as allyl and the like; aryl-lower alkyl groups such as benzyl, p-methoxybenzyl, 3,4-dimethoxybenzyl, diphenylmethyl, trityl and the like; oxygen-containing and sulfur-containing heterocyclic groups such as tetrahydrofuryl, tetrahydropyranyl, tetrahydrothiopyranyl and the like; lower alkoxy-lower alkyl groups such as methoxymethyl, 2-(trimethylsilyl))ethoxymethyl, 2-methoxy-1-methoxyethyl and the like; substituted silyl groups such as tert-butyldimethylsilyl, diphenylmethylsilyl and the like.

(D-1) A compound of general formula [2] is reacted with a compound of general formula [18], whereby a compound of general formula [7] can be obtained.

This reaction is carried out according to a method known per se, such as the same method as Production Process 1.

(D-2) A compound of general formula [2] is reacted with a compound of general formula [29] and the protecting group is removed, whereby a compound of general formula [21] can be obtained.

This reaction is achieved by carrying out the reaction according to a method known per se, such as the method as in Production Process 1, and then removing the protecting group.

(D-3) A compound of general formula [2] is reacted with a compound of general formula [19] in the presence of a base, whereby a compound of general formula [20] can be obtained.

This reaction can be carried out according to a method known per se, such as the same method as Production Process 5 (1).

(D-4) A compound of general formula [20] is subjected to a conventional hydrolysis of ether or amide, whereby a compound of general formula [4] can be obtained.

This reaction can be carried out according to a method known per se, such as the same method as (B-3).

(D-5) A compound of general formula [4] or general formula [20] is subjected to a conventional reduction reaction or addition of organometallic compound, whereby a compound of general formula [21] or a compound of general formula [30] can be obtained.

This reduction reaction or addition of organometallic compound can be carried out according to methods known per se, such as the same method as (C-12) or (C-16).

(D-6) A compound of general formula [4] is converted to a reactive derivative and then subjected to a condensation reaction with a compound of general formula [26], whereby a compound of general formula [31] can be obtained.

This reaction can be carried out according to a method known per se, such as the same method as (C-13)

(D-7) A compound of general formula [31] is subjected to a conventional hydrolysis and then to a decarboxylation reaction, whereby a compound of general formula [30] can be obtained.

This reaction can be carried out according to a method known per se, such as the same method as (C-15).

(D-8) A compound of general formula [30] is subjected to a conventional reduction reaction or an addition of organometallic compound, whereby a compound of general formula [21] can be obtained.

This reaction can be carried out according to a method known per se, such as the same method as (C-4).

(D-9) A compound of general formula [21] is treated with a halogenating agent or a sulfonylating agent in the presence or absence of a base, whereby a compound of general formula [7] can be obtained.

This reaction can be carried out according to a well known method, such as the same method as (B-5).

The compound of general formula [8] can be produced according to methods well known in themselves or an appropriate combination thereof, such as the Production Process E shown below.

Production Process E

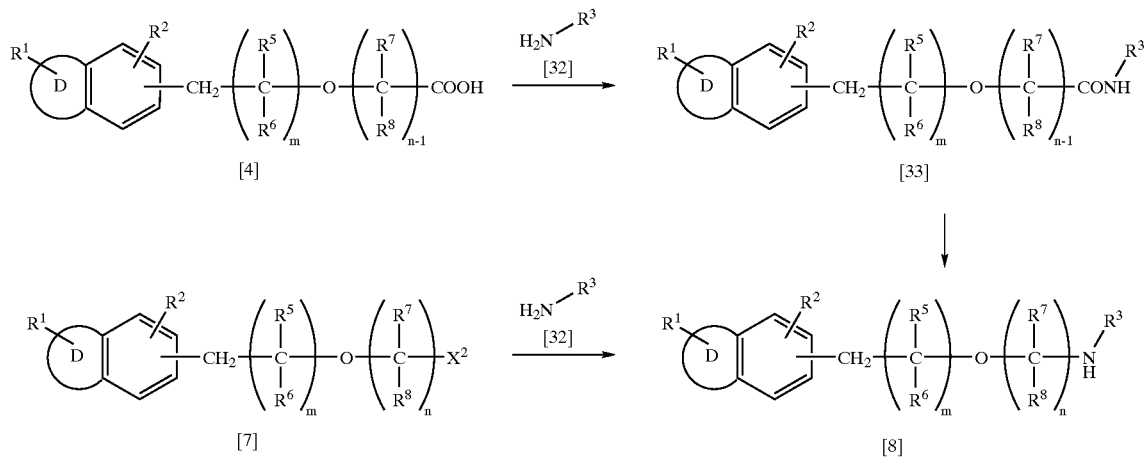

wherein $R^1$, $R^2$, $R^3$, $R^5$, $R^6$, $R^7$, $R^8$, $X^2$, m and n are as defined above.

(E-1) A compound of general formula [4] or reactive derivative thereof is reacted with a compound of general formula [32], whereby a compound of general formula [33] can be obtained.

This reaction can be carried out according to a method known per se, such as the same method as Production Process 2 (1).

(E-2) A compound of general formula [33] is subjected to a conventional reduction reaction, whereby a compound of general formula [8] can be obtained.

This reaction can be carried out according to a method known per se, such as the same method as Production Process 2 (2).

(E-3) A compound of general formula [7] is reacted with a compound of general formula [32] in the presence or absence of a base, whereby a compound of general formula [8] can be obtained.

This reaction can be carried out according to a method known per se, such as the same method as Production Process 3.

The compound of general formula [12] can be produced according to methods known per se, or an appropriate combination thereof, such as the production Process F shown below.

Production Process F

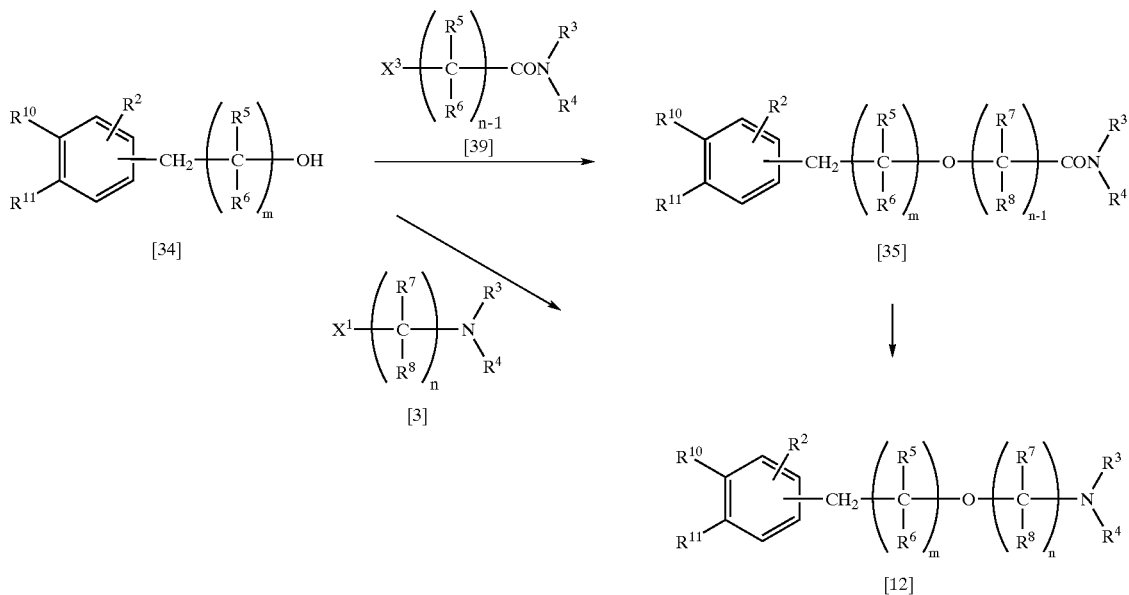

wherein $R^2$, $R^3$, $R^4$, $R^5$, $R^6$, $R^7$, $R^8$, $R^{10}$, $R^{11}$, $X^1$, $X^3$, m and n are as defined above.

(F-1) A compound of general formula [34] is reacted with a compound of general formula [39] in the presence of a base, whereby a compound of general formula [35] can be produced.

This reaction can be carried out according to a method known per se, such as the same method as Production Process 5.

(F-2) A compound of general formula [35] is subjected to a conventional reduction reaction, whereby a compound of general formula [12] can be obtained.

This reaction can be carried out according to a method known per se, such as the same method as Production Process 2 (2).

(F-3) A compound of general formula [34] is reacted with a compound of general formula [3] in the presence of a base, whereby a compound of general formula [12] can be obtained.

This reaction is carried out according to a method known per se, such as the same method as Production Process 1.

Alternatively, it is also possible to produce a compound of general formula [12] by a method other than the above, namely by using a compound of general formula [34] as a starting material and referring to the processes for producing the compound of general formula [1] and starting material thereof.

Next, the compounds of general formulas [13] and [23] which are starting materials for production of the starting intermediate compounds can be produced according to methods known per se or an appropriate combination thereof, such as the processes mentioned below.

Production Process G

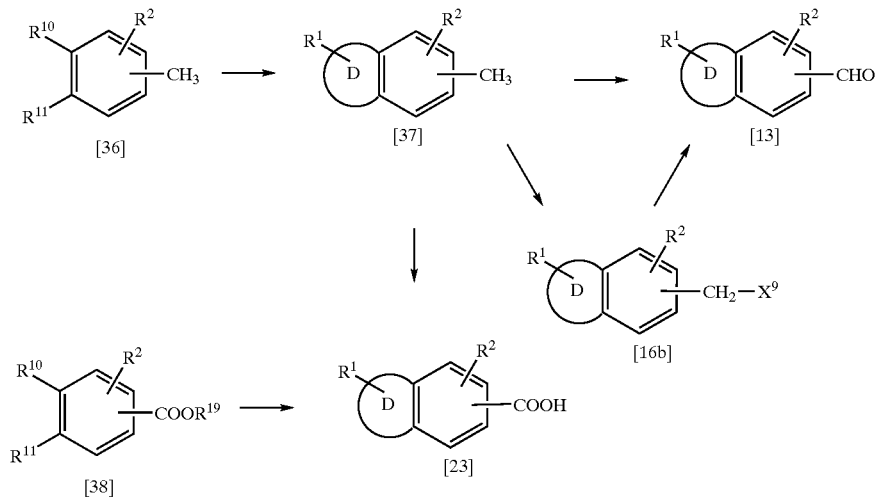

wherein $R^1$, $R^2$, $R^{10}$, $R^{11}$ and D are as defined above; $R^{19}$ represents a hydrogen atom or a protecting group for carboxyl group; and $X^9$ represents a halogen atom.

(G-1) A compound of general formula [36] is subjected to a conventional ring-closing reaction, whereby a compound of general formula [37] can be obtained.

This reaction can be carried out according to a method known per se, such as the method described in "Chemistry of Heterocyclic Compounds", Pages 16–80 (1988, Kodansha) and Shin Jikken Kagaku Koza, Vol. 14, [IV], edited by Chemical Society of Japan, Pages 1879–2406 (1977, Maruzen), or any analogous method.

(G-2) A compound of general formula [37] is subjected to a conventional oxidation reaction, whereby a compound of general formula [13] or [37] can be obtained.

This reaction can be carried out according to a method known per se, such as the method described in Shin Jikken Kagaku Koza, Vol. 14, [II], edited by Chemical Society of Japan, Pages 636–643 and 922–926 (1977, Maruzen), or any analogous method.

(G-3) As an alternative process, a process of subjecting a compound of general formula [37] to a conventional halogenation reaction to form a compound of general formula [16b] and then subjecting the compound [16b] to an oxidation reaction to form a compound of general formula [13] can be referred to.

This reaction can be carried out according to a method known per se, such as the method described in Shin Jikken Kagaku Koza, Vol. 14, [I], edited by Chemical Society of Japan, Pages 331–344 (1977, Maruzen) and Shin Jikken Kagaku Koza, Vol. 14, [II], edited by Chemical Society of Japan, Pages 636–643 (1977, Maruzen), or any analogous method.

(G-4) A compound of general formula [38] is subjected to a conventional ring-closing reaction, whereby a compound of general formula [23] can be produced.

This reaction can be carried out according to a method known per se, such as the method described in "Chemistry of Heterocyclic Compounds", Pages 16–80 (1988, Kodansha) and Shin Jikken Kagaku Koza, Vol. 14, [IV], edited by Chemical Society of Japan, Pages 1879–2406 (1977, Maruzen), or any analogous method.

The ring-closing method of Production Process G can be applied to the production of the compounds of general formulas [2], [2a], [15], [15a], [15b], [20], [20a], [21] and [21a].

In the above-mentioned Production Processes C, D, E, F and G, the compounds of general formulas [2], [3], [4], [7], [8], [12], [13], [15], [15a], [15b], [16], [16b], [17], [17a], [18], [19], [20], [21], [22], [23], [24], [25], [26], [27], [28], [29], [30], [31], [32], [33], [34], [35], [36], [37], [38] and [39] can be used in the form of a salt, too, if desired. As said salt, the same salts as mentioned in the paragraph of the compounds of general formula [1] can be referred to.

In cases where the compounds of general formulas [2], [3], [4], [7], [8], [12], [13], [15], [15a], [15b], [16], [16b], [17], [17a], [18], [19], [20], [21], [22], [23], [24], [25], [26], [27], [28], [29], [30], [31], [32], [33], [34], [35], [36], [37], [38] and [39] have an isomer such as optical isomer, geometrical isomer, tautomer or the like, all these isomers can be used in the present invention. Further, hydrated products and solvated products and all the crystal form thereof are also usable.

Some of the compounds of the general formulas [2], [3], [4], [7], [8], [12], [13], [15], [15a], [15b], [16], [16b], [17], [17a], [18], [19], [20], [21], [22], [23], [24], [25], [26], [27], [28], [29], [30], [31], [32], [33], [34], [35], [36], [37], [38] and [39] may have a hydroxyl group, an amino group or a carboxyl group. In such cases, it is possible to protect these hydroxyl, amino or carboxyl group previously and to remove these protecting groups after the reaction according to a method known per se, as occasion demands.

The compound of the present invention can be made into a pharmaceutical preparation such as oral agent (tablet, capsule, powder, granule, fine granule, pill, suspension, emulsion, solution, syrup and the like), injection, suppository, external preparation (ointment, plaster, etc.), aerosol, etc. by compounding the compound of the invention with various pharmaceutical additives such as excipient, binder, disintegrator, disintegration controller, solidification-adhesion preventor, lubricant, absorption-adsorption carrier, solvent, filler, isotonizing agent, dissolution aid, emulsifier, suspending agent, thickener, coating agent, absorption promoter, gelation-coagulation promoter, light stabilizer, preservative, moisture-proofing agent, emulsion-suspension-dispersion stabilizer, color protecting agent, de-oxygenating antioxidant, flavoring agent, colorant, forming agent, antifoaming agent, soothing agent, antistatic agent, buffering pH regulator and the like.

The agents mentioned above can be made into preparations by the conventional methods. The oral solid preparations such as tablet, powder, granule, etc. can be produced in the conventional manner by the use of pharmaceutical additives for solid preparations, of which the examples include an excipient such as lactose, sucrose, sodium chloride, glucose, starch, calcium carbonate, kaolinite, crystalline cellulose, anhydrous calcium secondary phosphate, partially pregelatinized starch, corn starch, alginic acid and the like; a binder such as single syrup, glucose solution, starch solution, gelatin solution, polyvinyl alcohol, polyvinyl ether, polyvinylpyrrolidone, carboxymethyl cellulose, shellac, methyl cellulose, ethyl cellulose, sodium alginate, gum arabic, hydroxypropylmethyl cellulose, hydroxypropyl cellulose, water, ethanol and the like; a disintegrator such as dry starch, alginic acid, agar powder, starch, crosslinked polyvinylpyrrolidone, crosslinked sodium carboxymethyl cellulose, calcium carboxymethyl cellulose, sodium starch glycolate and the like; a disintegration-controller such as stearyl alcohol, stearic acid, cacao butter, hydrogenated oils and the like; a solidification-adhesion preventor such as aluminum silicate, calcium hydrogen phosphate, magnesium oxide, talc, silicic acid anhydride and the like; a lubricant such as Carnauba wax, light silicic acid, aluminum silicate, magnesium silicate, hardened oils, hardened vegetable oil derivatives, sesame oil, whitened bees wax, titanium oxide, dried aluminum oxide gel, stearic acid, calcium stearate, magnesium stearate, talc, calcium hydrogen phosphate, sodium lauryl sulfate, polyethylene glycol and the like; an absorption promoter such as quaternary ammonium salts, sodium lauryl sulfate, urea, enzyme and the like; an absorption-adsorption carrier such as starch, lactose, kaolinite, bentonite, silicic acid anhydride, hydrated silicon dioxide, magnesium metasilicate-aluminate, colloidal silicic acid and the like; etc.

Further, the tablets can be made into tablets coated with usual skins as occasion demands, of which the examples include sugar-coated tablet, gelatin-coated tablet, tablet with intragastrically soluble coating, tablet with intraintestinally soluble coating, tablet with water soluble film coating, etc.

Capsules can be produced by mixing the main ingredient with the above-mentioned pharmaceutical additives and filling the mixture into a hard gelatin capsule, soft capsule, or the like.

Further, it is also possible to form the compound of the present invention into an aqueous or oily suspension, solution, syrup or elixir by mixing it with the above-mentioned various liquid preparation-forming additives and treating the mixture in a conventional manner.

Suppositories can be produced by adding an appropriate absorption promoter to polyethylene glycol, cacao butter, lanolin, higher alcohol, higher alcohol ester, gelatin, semi-synthetic glyceride, Witepsol or the like and forming the mixture into a preparation.

Injections can be produced in the conventional manner by the use of pharmaceutical additives for forming liquid preparations, of which the examples include a diluent such as water, ethyl alcohol, Macrogol, propylene glycol, citric acid, acetic acid, phosphoric acid, lactic acid, sodium lactate, sulfuric acid, sodium hydroxide and the like; a pH regulator and a buffering agent such as sodium citrate, sodium acetate, sodium phosphate and the like; a stabilizer such as sodium pyrophosphate, ethylenediaminetetraacetic acid, thiogly-colic acid, thiolactic acid and the like; an isotonizing agent such as sodium chloride, glucose, mannitol, glycerin and the like; a dissolution aid such as sodium carboxymethyl cellulose, propylene glycol, sodium benzoate, benzyl benzoate, urethane, ethanolamine, glycerin and the like; a pain stopping agent such as calcium gluconate, chlorobutanol, glucose, benzyl alcohol and the like; a local anesthetic; etc.

Ointments in the forms of paste, cream and gel can be produced by mixing the compound of the present invention with pharmaceutical additives including a base such as white Vaseline, polyethylene, paraffin, glycerin, cellulose derivative, polyethylene glycol, silicone, bentonite and the like; a preservative such as methyl p-oxybenzoate, ethyl p-oxybenzoate, propyl p-oxybenzoate and the like; a stabilizer; a wetting agent; etc. and forming the mixture into a preparation in the conventional manner.

For producing a plaster, a conventional support can be coated with the above-mentioned ointment, cream, gel, paste or the like in the usual manner. As the support, woven or unwoven fabrics made of cotton, staple fiber or chemical fiber, films of plasticized polyvinyl chloride, polyethylene, polyurethane or the like, or foamed sheets can be used.

Although the method for administering the above-mentioned pharmaceutical preparations is not particularly limited and is properly determined depending on the pharmaceutical form, the age, sex and other conditions of patient, and symptom of the patient.

Dosage of the active ingredient of the pharmaceutical preparation of the present invention should be properly decided in accordance with the method of use, the age and sex of patient, pathosis of patient, and other conditions. Usually, the active ingredient may be administered to an adult in dose of 0.1 to 500 mg per day in one portion or several portions.

Next, the pharmacological activities of the typical compounds of the present invention will be described.

[Anti-hypoxic Activity]

A test compound (100 mg/kg) dissolved in distilled water is orally administered to ddY male mice of 5–6 weeks age (6–10 heads per group). Thirty minutes after the administration, each mouse was introduced into a glass vessel, and a gas mixture consisting of 4% of oxygen and 96% of nitrogen was passed through the glass vessel at a rate of 5 L/minute. The period of the time from the beginning of sending the gas to the death of the animal was measured.

To the control group, only distilled water was orally given. Anti-hypoxic activity of test compound was calculated according to the following equation:

(Survival time of mouse in administered group)÷(Survival time of mouse in control group)×100(%)

As the result, the hypoxic activities were as follows:
the compound of Example 10: 170%,
the compound of Example 13: 160%,
the compound of Example 16: 158%,
the compound of Example 20: 155%,
the compound of Example 31: 248%,
the compound of Example 49: 173%,
the compound of Example 53: 200%,
the compound of Example 68: 202%,
the compound of Example 70: 213%,
the compound of Example 76: 194%,
the compound of Example 101: 187%,
the compound of Example 102: 210%,
the compound of Example 144: 250%,
the compound of Example 158: 179%.

[Nerve-regeneration Promoting Activity]

The test was carried out according to the description of Experimental Neurology, Vol. 140, Page 198 (1996).

SD rats (male, 6 weeks age, body weight 160–200 g) were anesthetized with Pentobarbital. The left sciatic nerve was exposed from the upper femoral muscular texture and peeled off from the surrounding texture, while taking care so as to give no injury to the muscular fiber.

By means of a needle holder with a flattened and smoothed contact surface, the sciatic nerve was pressed and crushed for a period of 90 seconds in a zone extending over about 10 mm from the branched part and having a width of 1.5 mm at the central portion. The crushed zone was marked with a thread at the end of neurilemma, and the operated portion was sutured. One hour after the crushing, a test compound dissolved in physiological salt solution was administered intra-abdominally at a dosage of 10 mg/kg. Thereafter, the same administration as above was repeated twice per day far 5 days.

Six days after the operation, the operated portion was again opened under an anesthesia using Pentobarbital to expose the sciatic nerve, and a forceps was made to contact to the nerve from a position about 25 mm distant from the crushed part. The forceps was slowly moved toward the crushed part until a reflex reaction appeared. The distance between the portion exhibiting reflex and the crushed portion was measured, and regarded as a regeneration distance. To the control group, only a saline was given.

The sciatic nerve regeneration rate of the test compound was calculated according to the following equation:

(Regeneration distance in administration group)÷(Regeneration distance in control group)×100(%)

As a result, the regeneration rates of sciatic nerve were as follows:
the compound of Example 10: 117%,
the compound of Example 16: 115%,
the compound of Example 27: 126%.

[An Activity of Inhibiting the Aβ-induced Nerve Cell Death]

The effect of inhibiting the death of cultured nerve cell induced by Aβ was examined by a modification of the method described in Brain Research, Vol. 639, Page 240 (1994).

Cerebral cortex excised from the brain of an embryo of Wistar rat (embryonal age 17–19 days) was cut into small pieces and then treated with trypsin to dissociate the nerve cells. The cells were spread onto a 48-well tissue-culture plate at a rate of 1×10⁵ cells per well, and cultured under a condition of 5% carbon dioxide, 37° C., in a Dulbecco modified Eagle medium to which B27 additives (product of GIBCO BRL) and 3.6 mg/mL glucose were added.

When the cultured had been continued for 12–13 days, a solution of potassium chloride was added so as to give a final concentration of 25 mmol/L, immediately after which a test agent was added. Twenty four hours after addition of the test agent, Aβ (25–35 peptide residues) dissolved in distilled water was added so as to give a final concentration of 20 μmol/L. Twenty four hours after addition of Aβ, the medium was changed to a medium prepared by adding test compound to Dulbecco modified Eagle medium to which B27 and 3.6 mg/mL glucose were added.

The inhibitory activity of test agent on the cultured nerve cell death was expressed by using the activity of inhibiting the decrease of MTT reducing ability as an index. That is, 48 hours after changing the medium, MTT assay developed by Mossmann [Journal of Immunological Methods, Vol. 65, Page 55 (1983)] was carried out, and the inhibition rate (%) of the agent on the decrease of MTT assay value induced by Aβ was calculated.

Inhibition rate=[(Aβ+MTT assay value of agent–added group)–(MTT assay value of Aβ–added group)]÷[MTT assay value of no addition group–MTT assay value of Aβ–added group]×100

As a result, at a concentration of 0.1 μM, the inhibition rates were as follows:

the compound of Example 68: 28%, the compound of Example 119: 39%, the compound of Example 137: 37%.

[Activity of Inhibiting the HNE-induced Nerve Cell Death]

The protecting effect against the death of cultured nerve cells induced by HNE was examined by a modification of the method described in the Journal of Neuroscience, Vol. 17, Page 5089 (1997).

Cerebral cortex excised from the brain of an embryo of Wistar rat (embryonal age 17–19 days) was cut into small pieces and then treated with trypsin to dissociate the nerve cells. The cells were spread onto a 48-well tissue-culture plate at a rate of 5×10⁵ cells per well, and cultured under a condition of 5% carbon dioxide, 37° C., in a Dulbecco modified Eagle medium to which 10% fetal calf serum and 3.6 mg/mL glucose were added.

In order to inhibit the proliferation of glia cells, cytosine arabinoside was added so as to give a final concentration of 10 μmol/L, from the day one after starting the culture. When the culture had been continued for 2 days, the medium was changed to a Dulbecco modified Eagle medium to which 10% fetal calf serum and 3.6 mg/mL glucose were added. When the culture had been continued for 7–8 days, a test agent was added, after which HNE was immediately added so as to give a final concentration of 25 μmol/L.

The inhibitory activity of an agent on the cultured nerve cell death was decreased by using the inhibitory activity on the depression of MTT reducing ability as an index. That is, 24 hours after addition of a test agent, MTT assay [Journal of Immunological Methods, Vol. 65, Page 55 (1983)] developed by Mossmann was carried out, based on which inhibitory rate (%) of the agent on the decrease of MTT assay induced by HNE was calculated.

Inhibitory rate=[MTT assay value of (HNE+agent)–added group)–(MTT assay value of HNE–added group)]÷(MTT assay value of no addition group–MTT assay value of HNE–added group)]×100

As a result, at a concentration of 0.1 μM, the inhibitory rates were as follows:

the compound of Example 10: 58%, the compound of Example 20: 69%, the compound of Example 68: 57%, the compound of Example 76: 49%, the compound of Example 105: 31%.

BEST EMBODIMENTS FOR CARRYING OUT THE INVENTION

Next, the present invention is explained by referring to Examples and Referential Examples. The invention is by no means limited by these examples.

In the eluent solutions, all the mixing ratios are expressed by "ratio by volume". The carried in the column chromatography was B.W. Silica gel BW-127ZH (product of Fuji Silysia Chemicals Co.). The carrier used in the reversed phase column chromatography was Chromatolex-ODS, DM1020T (product of Fuji Silysia Chemicals Co.).

EXAMPLE 1

In a mixture of 10 mL of 50% (W/V) aqueous solution of sodium hydroxide and 2 mL of toluene is suspended 2.00 g of 2-benzo[b]thiophen-5-yl-1-ethanol. To the suspension are added 2.51 g of N-(2-chloroethyl)-N,N-diethylamine hydrochloride and 0.38 g of tetra-n-butylammonium hydrogen sulfate, and the resulting mixture is heated under reflux for one hour. Water and toluene are added to the reaction mixture, and the organic layer is separated. The organic layer is washed successively with water and saturated aqueous solution of sodium chloride and dried over anhydrous magnesium sulfate, the solvent is distilled off under reduced pressure, and the residue is purified by column chromatography (eluent:chloroform:methanol=10:1) to obtain 3.10 g of N-[2-(2-benzo[b]thiophen-5-ylethoxy)ethyl]-N,N-diethylamine as an oily product.

NMR(CDCl₃)δ: 1.01(6H, t, J=7 Hz), 2.55(4H, q, J=7 Hz), 2.65(2H, t, J=6 Hz), 3.00(2H, t, J=7 Hz), 3.55(2H, t, J=6 Hz), 3.70(2H, t, J=6 Hz), 7.21(1H, dd, J=1, 8 Hz), 7.23(1H, d, J=5 Hz), 7.42(1H, d, J=5 Hz), 7.66(1H, d, J=1 Hz), 7.79(1H, d, J=8 Hz).

EXAMPLES 2–9

The procedure of Example 1 is repeated to obtain the following compounds.

No.2: N-[2-(2-Benzo[b]thiophen-5-ylethoxy)ethyl]-N,N-dimethylamine

IR(neat)cm⁻¹: 2940, 2862, 1458, 1116, 1052, 701.

NMR(CDCl₃)δ: 2.25(6H, s), 2.50(2H, t, J=6 Hz), 3.01 (2H, t, J=7 Hz), 3.55(2H, t, J=6 Hz), 3.70(2H, t, J=7 Hz), 7.21(1H, dd, J=1, 8 Hz), 7.26(1H, d, J=5 Hz), 7.40(1H, d, J=5 Hz), 7.65(1H, d, J=1 Hz), 7.78(1H, d, J=8 Hz).

No.3: N,N-Dimethyl-N-{2-[2-(2-naphthyl)ethoxy]-ethyl}-amine

IR(neat)cm⁻¹: 2941, 2862, 1458, 1116, 817, 746.

NMR(CDCl₃)δ: 2.25(6H, s), 2.50(2H, t, J=6 Hz), 3.07 (2H, t, J=7 Hz), 3.57(2H, t, J=6 Hz), 3.75(2H, t, J=7 Hz), 7.2–7.6(3H, m), 7.6–8.0(4H, m).

No.4: N-[2-(2-Benzo[b]thiophen-5-ylethoxy)ethyl]-N,N-diisopropylamine

IR(neat)cm$^{-1}$: 2965, 1362, 1111, 700.

NMR(CDCl$_3$)δ: 0.99(12H, d, J=7 Hz), 2.59(2H, t, J=7 Hz), 2.98(2H, sept, J=7 Hz), 2.99(2H, t, J=7 Hz), 3.42(2H, t, J=7 Hz), 3.70(2H, t, J=7 Hz), 7.20(1H, dd, J=1, 8 Hz), 7.27(1H, d, J=5 Hz), 7.42(1H, d, J=5 Hz), 7.67(1H, d, J=1 Hz), 7.79(1H, d, J=8 Hz).

No.5: N,N-Diethyl-N-{2-[2-(2-methylbenzo[b]-thiophen-5-yl)ethoxy]ethyl}-amine

IR(neat)cm$^{-1}$: 2968, 2865, 1114.

NMR(CDCl$_3$)δ: 1.01(6H, t, J=7 Hz), 2.55(4H, q, J=7 Hz), 2.57(3H, s), 2.65(2H, t, J=6 Hz), 2.96(2H, t, J=7 Hz), 3.54(2H, t, J=6 Hz), 3.68(2H, t, J=7 Hz), 6.89(1H, s), 7.09(1H, d, J=8 Hz), 7.48(1H, s), 7.64(1H, d, J=8 Hz).

No.6: N,N-Diethyl-N-{2-[2-(6-quinolyl)ethoxy]-ethyl}-amine

IR(neat)cm$^{-1}$: 2968, 2868, 1501, 1114, 837.

NMR(CDCl$_3$)δ: 1.00(6H, t, J=7 Hz), 2.55(4H, q, J=7 Hz), 2.65(2H, t, J=6 Hz), 3.07(2H, t, J=7 Hz), 3.66(2H, t, J=6 Hz), 3.76(2H, t, J=7 Hz), 7.37(1H, dd, J=4, 8 Hz), 7.61(1H, dd, J=1, 8 Hz), 7.65(1H, d, J=1 Hz), 8.03(1H, d, J=8 Hz), 8.09(1H, dd, J=1, 8 Hz), 8.87(1H, dd, J=1, 4 Hz).

No.7: N,N-Diethyl-N-{2-[2-(2-naphthyl)ethoxy]-ethyl}-amine

IR(neat)cm$^{-1}$: 2966, 1109, 815, 739.

NMR(CDCl$_3$)δ: 1.01(6H, t, J=7 Hz), 2.55(4H, q, J=7 Hz), 2.65(2H, t, J=6 Hz), 3.05(2H, t, J=7 Hz), 3.56(2H, t, J=6 Hz), 3.74(2H, t, J=7 Hz), 7.2–7.6(3H, m), 7.6–8.0(4H, m).

No.8: N-[2-(2-Benzo[b]furan-5-ylethoxy)ethyl]-N,N-dimethylamine

IR(neat)cm$^{-1}$: 2941, 2862, 2770, 1468, 1112.

NMR(CDCl$_3$)δ: 2.26(6H, s), 2.50(2H, t, J=6 Hz), 2.99(2H, t, J=7 Hz), 3.56(2H, t, J=6 Hz), 3.68(2H, t, J=7 Hz), 6.71(1H, dd, J=1, 2 Hz), 7.14(1H, dd, J=2, 9 Hz), 7.42(1H, d, J=9 Hz), 7.44(1H, d, J=2 Hz), 7.59(1H, d, J=2 Hz).

No.9: N-[2-(2-Benzo[b]furan-5-ylethoxy)ethyl]-N,N-diethylamine

IR(neat)cm$^{-1}$: 2967, 2868, 1468, 1111.

NMR(CDCl$_3$)δ: 1.01(6H, t, J=7 Hz), 2.55(4H, q, J=7 Hz), 2.65(2H, t, J=6 Hz), 2.97(2H, t, J=7 Hz), 3.54(2H, t, J=6 Hz), 3.68(2H, t, J=7 Hz), 6.70(1H, dd, J=1, 2 Hz), 7.12(1H, dd, J=2, 9 Hz), 7.41(1H, d, J=9 Hz), 7.42(1H, d, J=2 Hz), 7.59(1H, d, J=2 Hz).

EXAMPLE 10

In 20 mL of ethyl acetate is dissolved 3.10 g of N-[2-(2-benzo[b]thiophen-5-ylethoxy)ethyl]-N,N-diethylamine. To the solution is added 10 mL of a solution of 1.10 g of oxalic acid in ethyl acetate, and the resulting solution is stirred at ambient temperature for 2 hours. The deposited crystal is collected by filtration, washed with ethyl acetate and dried to obtain 3.10 g of N-[2-(2-(benzo[b]thiophen-5-ylethoxy)ethyl]-N,N-diethylamine oxalate.

mp: 70–71° C.

IR(KBr)cm$^{-1}$: 3447, 1112, 720.

NMR(DMSO-d$_6$)δ: 1.08(6H, t, J=7 Hz), 2.8–3.5(8H, m), 3.72(4H, brt, J=7 Hz), 4.9(2H, brs), 7.25(1H, d, J=8 Hz), 7.39(1H, d, J=5 Hz), 7.73(1H, d, J=5 Hz), 7.76(1H, s), 7.92(1H, d, J=8 Hz).

EXAMPLES 11–15

The procedure of Example 10 is repeated to obtain the following compounds.

No.11: N,N-Diethyl-N-{2-[2-(2-naphthyl)ethoxy]-ethyl}amine oxalate mp: 67–72° C.

IR(KBr)cm$^{-1}$: 3425, 1636, 1404, 1113.

NMR(DMSO-d$_6$)δ: 1.07(6H, t, J=7 Hz), 2.8–3.3(8H, m), 3.6–3.9(4H, m), 7.3–7.6(3H, m), 7.7–8.0(4H, m), 8.1(2H, brs).

No.12: N-[2-(2-Benzo[b]furan-5-ylethoxy)ethyl]-N,N-dimethylamine oxalate mp: 101–103° C.

IR(KBr)cm$^{-1}$: 3418, 1470, 1112, 721.

NMR(DMSO-d$_6$)δ: 2.68(6H, s), 2.92(2H, t, J=7 Hz), 3.17(2H, t, J=5 Hz), 3.6–3.8(4H, m), 6.89(1H, d, J=1 Hz), 7.19(1H, dd, J=2, 8 Hz), 7.4–7.6(2H, m), 7.94(1H, d, J=2 Hz), 9.1(2H, brs).

No.13: N-[2-(2-Benzo[b]furan-5-ylethoxy)ethyl]-N,N-diethylamine oxalate mp: 78–82° C.

IR(KBr)cm$^{-1}$: 3448, 1111, 720.

NMR(DMSO-d$_6$)δ: 1.10(6H, t, J=7 Hz), 2.8–3.3(8H, m), 3.6–3.9(4H, m), 6.6(2H, brs), 6.89(1H, d, J=1 Hz), 7.19(1H, dd, J=1, 9 Hz), 7.51(1H, d, J=9 Hz), 7.51(1H, J=2 Hz), 7.94(1H, d, J=2 Hz).

No.14: N,N-Diethyl-N-{2-[2-(2-methylbenzo[b]-thiophen-5-yl)ethoxy]ethyl}-amine oxalate mp: 96–98° C.

IR(KBr)cm$^{-1}$: 3448, 1224, 1113, 720.

NMR(DMSO-d$_6$)δ: 1.08(6H, t, J=7 Hz), 2.54(3H, s), 2.8–3.3(8H, m), 3.6–3.8(4H, m), 7.0–8.0(6H, m).

No.15 N,N-Diethyl-N-{2-[2-(6-quinolyl)ethoxy]-ethyl}amine oxalate mp: 90–92° C.

IR(KBr)cm$^{-1}$: 3422, 2664, 1114, 721.

NMR(DMSO-d$_6$)δ: 1.07(6H, t, J=7 Hz), 2.9–3.3(8H, m), 3.6–3.9(4H, m), 7.55(1H, dd, J=4, 8 Hz), 7.68(1H, dd, J=1, 8 Hz), 7.81(1H, d, J=1 Hz), 7.96(1H, d, J=8 Hz), 8.38(1H, dd, J=1, 8 Hz), 8.4(2H, brs), 8.85(1H, dd, J=1, 4 Hz).

EXAMPLE 16

In 12.8 mL of ethyl acetate is dissolved 2.55 g of N-[2-(2-benzo[b]thiophen-5-ylethoxy)ethyl]-N,N-dimethylamine. To the solution is added 5.8 mL of a solution of 2.3 mol of dry hydrogen chloride in ethyl acetate. The resulting mixture is stirred at ambient temperature for one hour. The deposited crystal is collected by filtration, washed with ethyl acetate and dried to obtain 1.80 g of N-[2-(2-benzo[b]thiophen-5-ylethoxy)ethyl]-N,N-dimethylamine hydrochloride.

mp: 116–117° C.

IR(KBr)cm$^{-1}$: 2956, 2690, 1475, 1115, 704.

NMR(DMSO-d$_6$)δ: 2.69(6H, s), 2.96(2H, t, J=7 Hz), 3.21(2H, t, J=6 Hz), 3.71(2H, t, J=7 Hz), 3.78(2H, t, J=6 Hz), 7.28(1H, d, J=8 Hz), 7.40(1H, d, J=5 Hz), 7.73(1H, d, J=5 Hz), 7.76(1H, s), 7.90(1H, d, J=8 Hz), 10.8(1H, brs).

EXAMPLES 17–18

The procedure of Example 16 is repeated to obtain the following compounds.

No.17: N,N-Dimethyl-N-{2-[2-(2-naphthyl)ethoxy]-ethyl}-amine hydrochloride mp: 105–107° C.

IR(KBr)cm$^{-1}$: 2686, 1464, 1112.

NMR(DMSO-d$_6$)δ: 2.69(6H, s), 3.02(2H, t, J=7 Hz), 3.22(2H, t, J=5 Hz), 3.76(2H, t, J=7 Hz), 3.78(2H, t, J=5 Hz), 7.3–7.6(3H, m), 7.7–8.0(4H, m), 10.4(1H, brs).

No.18: N-[2-(2-Benzo[b]thiophen-5-ylethoxy)ethyl]-N,N-diisopropylamine hydrochloride mp: 78–79° C.

IR(KBr)cm$^{-1}$: 3504, 2943, 1118.

NMR(DMSO-d$_6$)δ: 1.21(6H, d, J=7 Hz), 1.25(6H, d, J=7 Hz), 2.96(2H, t, J=7 Hz), 3.1–3.9(8H, m), 7.26(1H, d, J=8 Hz), 7.39(1H, d, J=5 Hz), 7.73(1H, d, J=5 Hz), 7.76(1H, s), 7.91(1H, d, J=8 Hz), 9.6(1H, brs).

EXAMPLE 19

In 10 mL of N,N-dimethylformamide is dissolved 1.89 g of 2-(2-benzo[b]thiophen-5-ylethoxy)ethyl methanesulfonate. To the solution are added 0.99 g of N-benzyl-N-methylamine and 1.74 g of potassium carbonate, and the resulting mixture is stirred at 80° C. for 3 hours. Then, the reaction mixture is introduced into a mixture of ethyl acetate and water, and the organic layer is separated. The organic layer is washed successively with water and saturated aqueous solution of sodium chloride, and dried over anhydrous magnesium sulfate. The solvent is distilled off under reduced pressure, and the residue is purified by column chromatography (eluent:chloroform:methanol=10:1) to obtain 2.03 g of N-[2-(2-benzo]b]thiophen-5-ylethoxy)ethyl]-N-benzyl[N-methylamine as an oily product.

IR(neat)cm$^{-1}$: 2941, 2862, 1678, 1113, 700.

NMR(CDCl$_3$)δ: 2.24(3H, s), 2.61(2H, t, J=6 Hz), 3.00 (2H, t, J=7 Hz), 3.53(2H, s), 3.66(2H, t, J=6 Hz), 3.69(2H, t, J=7 Hz), 7.1–7.5(8H, m), 7.65(1H, s), 7.77(1H, d, J=8 Hz).

EXAMPLE 20

In 20 mL of ethyl acetate is dissolved 2.03 g of N-[2-(2-benzo[b]thiophen-5-ylethoxy)ethyl]-N-benzyl-N-methylamine. After adding 10 mL of a solution of 0.65 g of oxalic acid in ethyl acetate to the solution the resulting mixture is stirred at ambient temperature for 2 hours. The deposited crystal is collected by filtration, washed with ethyl acetate and dried to obtain 1.98 g of N-[2-(2-benzo[b]thiophen-5-ylethoxy)ethyl]-N-benzyl-N-methylamine oxalate.

mp: 136–137° C.

IR(KBr)cm$^{-1}$: 3446, 1404, 1118.

NMR(DMSO-d$_6$)δ: 2.49(3H, s), 2.8–3.1(4H, m), 3.6–3.8 (4H, m), 4.02(2H, s), 5.0(2H, brs), 7.2–8.0(10H, m).

EXAMPLE 21

In 3 mL of N,N-dimethylformamide is dissolved 1.00 g of 2-[2-(1,3-benzodioxol-5-yl)ethoxy]ethyl methanesulfonate. To the solution is added 2.54 g of diethylamine. The resulting mixture is stirred at 100° C. for 2 hours in an ampoule. After cooling, the reaction mixture is introduced into a mixture of water and ethyl acetate, pH is adjusted to 1.0 with 2 mol/L hydrochloric acid, and the aqueous layer is separated. Ethyl acetate is added to the aqueous layer, pH is adjusted to 9.5 with sodium carbonate, and the organic layer is separated. The organic layer is washed successively with water and saturated aqueous solution of sodium chloride and dried over anhydrous magnesium sulfate, the solvent is distilled off under reduced pressure, and the residue is purified by column chromatography (eluent:chloroform:methanol=20:1 to 10:1) to obtain 0.75 g of N-{2-[2-(1,3-benzodioxol-5-yl)ethoxy]ethyl}-N,N-diethylamine as an oily product.

IR(neat)cm$^{-1}$: 2968, 1490, 1247, 1112, 1042.

NMR(CDCl$_3$)δ: 1.02(6H, t, J=7 Hz), 2.52(4H, q, J=7 Hz), 2.64(2H, t, J=6 Hz), 2.76(2H, t, J=7 Hz), 3.52(2H, t, J=6 Hz), 3.60(2H, t, J=7 Hz), 5.91(2H, s), 6.70(3H, brs).

EXAMPLES 22–24

The procedure of Example 21 is repeated to obtain the following compounds.

No.22: N-{2-[2-(1,3-benzodioxol-5-yl)ethoxy]ethyl}-N,N-dimethylamine

IR(neat)cm$^{-1}$: 2864, 2771, 1490, 1247, 1115, 1041.

NMR(CDCl$_3$)δ: 2.26(6H, s), 2.49(2H, t, J=6 Hz), 2.81 (2H, t, J=7 Hz), 3.53(2H, t, J=6 Hz), 3.61(2H, t, J=7 Hz), 5.91(2H, s), 6.71(3H, s).

No.23: N,N-Dimethyl-N-{2-[2-(2-phenylbenzo[b]-thiophen-5-yl)ethoxy]ethyl}amine

No.24 N,N-Diethyl-N-{2-[2-(2-phenylbenzo[b]-thiophen-5-yl)ethoxy]ethyl}amine

EXAMPLE 25

In 3.8 mL of ethyl acetate is dissolved 0.75 g of N-{2-[2-(1,3-benzodioxol-5-yl)ethoxy]ethyl}-N,N-diethylamine. To the solution is added 1.6 mL of a 2.3 mol/L solution of dry hydrogen chloride in ethyl acetate. The mixture is stirred at ambient temperature for one hour and the at 5° C. for one hour. The deposited crystal is collected by filtration, washed with ethyl acetate and dried to obtain 0.67 g of N-{2-[2-(1,3-benzodioxol-5-yl)ethoxy]ethyl}-N,N-diethylamine.

mp: 83–84° C.

IR(KBr)cm$^{-1}$: 3434, 1490, 1248.

NMR(DMSO-d$_6$)δ: 1.16(6H, t, J=7 Hz), 2.74(2H, t, J=7 Hz), 3.0–3.3(6H, m), 3.5–3.8(4H, m), 5.95(2H, s)6.7–6.9 (3H, m), 10.5(1H, brs).

EXAMPLES 26–27

Example 25 is repeated to obtain the following compounds.

No.26: N,N-Dimethyl-N-{2-[2-(2-phenylbenzo[b]-thiophen-5-yl)ethoxy]ethyl}-amine hydrochloride mp: 170–172° C.

IR(KBr)cm$^{-1}$: 3406, 1118, 758.

NMR(CDCl$_3$)δ: 2.67(3H, s), 2.72(3H, s), 2.8–3.4(4H, m), 3.6–4.1(4H, m), 7.0–8.0(9H, m), 12.4(1H, brs).

No.27: N,N-Diethyl-N-{2-[2-(2-phenylbenzo[b]-thiophen-5-yl)ethoxy]ethyl}-amine hydrochloride mp: 131–138° C.

IR(KBr)cm$^{-1}$: 2651, 1450, 1114, 758.

NMR(CDCl$_3$)δ: 1.23(6H, t, J=7 Hz), 2.7–3.4(8H, m), 3.6–4.2(4H, m), 7.0–8.0(9H, m), 11.9(1H, brs).

EXAMPLE 28

In 2 mL of ethyl acetate is dissolved 0.66 g of N-{2-[2-(1,3-benzodioxol-5-yl)ethoxy]ethyl}-N,N-dimethylamine. To the solution is added 1 mL of a solution of 0.25 g of oxalic acid in ethyl acetate. The resulting mixture is stirred at ambient temperature for 2 hours. The reaction mixture is diluted with 10 mL of diisopropyl ether. The deposited crystal is collected by filtration, washed with diisopropyl ether and dried to obtain 0.76 g of N-{2-[2-(1,3-benzodioxol-5-yl)ethoxy]ethyl}-N,N-dimethylamine oxalate.

mp: 109–112° C.

IR(KBr)cm$^{-1}$: 3432, 1490, 1248.

NMR(DMSO-d$_6$)δ: 2.69(6H, s), 2.75(2H, t, J=4 Hz), 3.16(2H, t, J=6 Hz), 3.5–3.7(4H, m), 5.96(2H, s), 6.6–6.8 (3H, m), 7.4(2H, brs).

EXAMPLE 29

(1) In 10 mL of methylene chloride is dissolved 1.00 g of 2-[2-(6-fluorobenzo[b]thiophen-5-yl)ethoxy]-acetic acid. The solution is cooled to 5° C., 0.55 g of oxalyl chloride and 0.1 mL of N,N-dimethylformamide are added thereto, and the resulting mixture is stirred at ambient temperature for 2 hours. Water is added to the reaction mixture, pH is adjusted to 1.0 with 2 mol/L hydrochloric acid, and the organic layer is separated. The organic layer is washed with saturated aqueous solution of sodium chloride and dried over anhydrous magnesium sulfate, and the solvent is distilled off under reduced pressure. Thus, 1.24 g of N,N-diethyl-2-[2-(6-fluorobenzo[b]thiophen-5-yl)ethoxy]acetamide is obtained as an oily product.

NMR(CDCl$_3$)δ: 1.10(6H, t, J=7 Hz), 3.0–3.6(6H, m), 3.81(2H, t, J=7 Hz), 4.14(2H, s), 7.24(1H, d, J=5 Hz), 7.37(1H, d, J=5 Hz), 7.51(1H, d, J=10 Hz), 7.69(1H, d, J=7 Hz).

The following compound is obtained in the same manner as above.

N,N-Dimethyl-2-(2-benzo[b]thiophen-7-ylethoxy)-acetamide

NMR(CDCl$_3$)δ: 2.83(3H, s), 2.88(3H, s), 3.22(2H, t, J=7 Hz), 3.92(2H, t, J=7 Hz), 4.15(2H, s), 7.2–7.5(4H, m), 7.71(1H, dd, J=2, 7 Hz).

(2) In 20 mL of tetrahydrofuran is dissolved 1.24 g of N,N-diethyl-2-[2-(6-fluorobenzo[b]thiophen-5-yl)ethoxy]-acetamide. The solution is cooled to 5° C., and 7.86 mL of a 1 mol/L solution of borane-tetrahydrofuran complex in tetrahydrofuran is dropwise added thereto. After stirring the resulting mixture at ambient temperature for 2 hours, 4.00 mL of 2 mol/L hydrochloric acid is dropwise added, and the resulting mixture is heated under reflux for 30 minutes. After cooling, water and ethyl acetate are added to the reaction mixture, pH is adjusted to 13 with 5 mol/L aqueous solution of sodium hydroxide, and the organic layer is separated. The organic layer is washed with saturated aqueous solution of sodium chloride and dried over anhydrous magnesium sulfate, the solvent is distilled off under reduced pressure, and the residue is purified by column chromatography (eluent:chloroform:methanol=30:1 to 10:1) to obtain 0.90 g of N,N-diethyl-N-{2-[2-(6-fluorobenzo[b]thiophen-5-yl)ethoxy]ethyl}-amine as an oily product.

IR(neat)cm$^{-1}$: 2968, 2870, 1458, 1256, 1114.

NMR(CDCl$_3$)δ: 1.00(6H, t, J=7 Hz), 2.55(4H, q, J=7 Hz), 2.67(2H, t, J=6 Hz), 3.02(2H, t, J=7 Hz), 3.55(2H, t, J=6 Hz), 3.70(2H, t, J=7 Hz), 7.23(1H, d, J=5 Hz), 7.36(1H, d, J=5 Hz), 7.51(1H, d, J=10 Hz), 7.66(1H, d, J=7 Hz).

EXAMPLE 30

Example 29(2) is repeated to obtain the following compounds.

No.30 N-[2-(2-Benzo[b]thiophen-7-ylethoxy)ethyl]-N,N-dimethylamine

IR(neat)cm$^{-1}$: 2863, 1459, 1117, 794.

NMR(CDCl$_3$)δ: 2.25(6H, s), 2.56(2H, t, J=6 Hz), 3.20(2H, t, J=7 Hz), 3.57(2H, t, J=6 Hz), 3.84(2H, t, J=7 Hz), 7.0–7.6(4H, m), 7.78(1H, d, J=7 Hz).

EXAMPLE 31

In 2.5 mL of ethyl acetate is dissolved 0.90 g of N,N-diethyl-N-{2-[2-(6-fluorobenzo[b]thiophen-5-yl)ethoxy]ethyl}-amine, to which is added 2 ml of a solution of 0.27 g of oxalic acid in ethyl acetate. The resulting mixture is stirred at ambient temperature for 2 hours. The reaction mixture is diluted with 10 mL of diisopropyl ether, and the resulting crystalline precipitate is collected by filtration, washed with diisopropyl ether and dried. Thus, 0.83 g of N,N-diethyl-N-{2-[2-(6-fluorobenzo[b]thiophen-5-yl)ethoxy]ethyl}amine oxalate is obtained.

mp: 54–62° C.

IR(KBr)cm$^{-1}$: 3446, 1457, 720.

NMR(DMSO-d$_6$)δ: 1.08(6H, t, J=7 Hz), 2.8–3.3(8H, m), 3.5–3.9(4H, m), 7.39(1H, d, J=6 Hz), 7.73(1H, d, J=10 Hz), 7.78(1H, d, J=6 Hz), 7.90(1H, d, J=5 Hz), 8.2(2H, brs).

EXAMPLE 32

In 2.5 mL of ethyl acetate is dissolved 0.49 g of N-[2-(2-benzo[b]thiophen-7-ylethoxy)ethyl]-N,N-dimethylamine, to which is added 0.73 mL of 3.5 mol/L solution of dry hydrogen chloride in ethyl acetate. The resulting solution is stirred at ambient temperature for one hour. The deposited crystal is collected by filtration, washed with ethyl acetate and dried to obtain 0.44 g of N-[2-(2-benzo[b]thiophen-7-ylethoxy)ethyl]-N,N-dimethylamine hydrochloride.

mp: 130–132° C.

IR(KBr)cm$^{-1}$: 2471, 1477, 1123, 713.

NMR(DMSO-d$_6$)δ: 2.68(6H, s), 3.0–3.6(4H, m), 3.6–4.0 (4H, m), 7.2–7.6(3H, m), 7.7–7.9(2H, m), 10.4(1H, brs).

EXAMPLE 33

In 30 mL of tetrahydrofuran is dissolved 6.00 g of N-[2-(2-benzo[b]thiophen-5-ylethoxy)ethyl]-N,N-diethylamine. The solution is cooled to −60° C., and 10.6 mL of 1.57 mol/L solution of n-butyllithium in hexane is dropwise added. The resulting mixture is stirred at the same temperature as above for one hour, an excessive amount of dry carbon dioxide gas is introduced, after which the temperature is elevated to ambient temperature and the mixture is stirred for 30 minutes. Water is added to the mixture, pH is adjusted to 7 with 2 mol/L hydrochloric acid, and the solvent is distilled off under reduced pressure. The residue is purified by reversed phase column chromatography (eluent:water:methanol=7:3) and filtered together with ethyl acetate. Thus, 3.66 g of 5-{2-[2-(diethylamino)ethoxy]ethyl}-benzo[b]thiophene-2-carboxylic acid is obtained as a crystalline product.

IR(KBr)cm$^{-1}$: 3421, 1616, 1333, 1102.

NMR(CDCl$_3$)δ: 1.13(6H, t, J=7 Hz), 2.6–3.3(4H, m), 2.96(4H, q, J=7 Hz), 3.5–4.0(4H, m), 7.18(1H, d, J=7 Hz), 7.55(1H, s), 7.67(1H, d, J=7 Hz), 7.71(1H, s), 9.8(1H, brs).

EXAMPLE 34

In 20 mL of ethanol is dissolved 1.90 g of 5-{2-[2-(diethylamino)ethoxy]ethyl}-benzo[b]thiophen-2-carboxylic acid, to which is added 5.6 mL of 1.38 mol/L solution of dry hydrogen chloride in ethanol. The resulting mixture is stirred at ambient temperature for 2 hours, and diluted with 20 mL of ethyl acetate. The deposited crystal is collected by filtration, washed with ethyl acetate and dried to obtain 1.51 g of 5-{2-[2-(diethylamino)ethoxy]ethyl}-benzo[b]thiophene-2-carboxylic acid hydrochloride.

mp: 148–150° C.

IR(KBr)cm$^{-1}$: 2949, 1706, 1141, 898, 815.

NMR(DMSO-d$_6$)δ: 1.13(6H, t, J=7 Hz), 2.8–3.3(8H, m), 3.6–3.9(4H, m), 7.43(1H, d, J=8 Hz), 7.89(1H, s), 7.97(1H, d, J=8 Hz), 8.07(1H, s), 10.6(1H, brs), 13.4(1H, brs).

EXAMPLE 35

In 30 mL of tetrahydrofuran is dissolved 2.18 g of 5-{2-[2-(diethylamino)ethoxy]ethyl}benzo[b]-thiophene-2- carboxylic acid, to which is added 1.98 g of N,N'-carbonyldiimidazole. The resulting mixture is stirred at ambient temperature for one hour. Then, 50 mL of 25% aqueous ammonia is added to the mixture and the resulting mixture is stirred at ambient temperature for one hour. Ethyl acetate is added to the mixture, the organic layer is separated, washed with water and saturated aqueous solution of sodium chloride successively and dried over anhydrous magnesium sulfate, the solvent is distilled off under reduced pressure, and the residue is purified by column chromatography (eluent:chloroform:methanol to chloroform:methanol:ammonia=5:1 to 100:10:1). Thus, 2.00 g of 5-{2-[2-(diethylamino)ethoxy]ethyl}benzo[b]-thiophene-2-carboxamide is obtained as a colorless crystalline product.

mp: 82–84° C.

IR(KBr)cm$^{-1}$: 3362, 1646, 1608, 1112, 894, 810.

NMR(CDCl$_3$)δ: 1.00(6H, t, J=7 Hz), 2.56(4H, q, J=7 Hz), 2.65(2H, t, J=6 Hz), 2.99(2H, t, J=7 Hz), 3.55(2H, t, J=6 Hz), 3.70(2H, t, J=7 Hz), 6.2(2H, brs), 7.31(1H, dd, J=1, 8 Hz), 7.67(1H, d, J=1 Hz), 7.74(1H, s), 7.77(1H, d, J=8 Hz).

EXAMPLE 36

In a mixture of 1 mL of toluene and 3.5 ml of 50% (W/V) aqueous solution of sodium hydroxide is suspended 0.70 g of 2-(1-naphthyl)-1-ethanol, to which are added 1.00 g of N-(2-chloroethyl)-N,N-diethylamine hydrochloride and 0.14 g of tetra-n-butylammonium hydrogen sulfate. The mixture is heated under reflux for 2.5 hours. Water and toluene are added to the reaction mixture, and the organic layer is separated. The organic layer is washed with water and saturated aqueous solution of sodium chloride successively and dried over anhydrous magnesium sulfate, the solvent is distilled off under reduced pressure, and the residue is purified by column chromatography (eluent:chloroform:methanol=10:1). Thus, 1.06 g of N,N-diethyl-N-{2-[2-(1-naphthyl)ethoxy]ethyl}-amine is obtained as an oily product.

IR(neat)cm$^{-1}$: 2968, 2871, 1114, 797.

NMR(CDCl$_3$)δ: 1.02(6H, t, J=7 Hz), 2.56(4H, q, J=7 Hz), 2.66(2H, t, J=6 Hz), 3.45(2H, t, J=7 Hz), 3.56(2H, t, J=6 Hz), 3.79(2H, t, J=7 Hz), 7.4–7.6(4H, m), 7.7–7.9(2H, m), 8.0–8.1(1H, m).

EXAMPLES 37–48

Example 1 is repeated to obtain the following compounds.
No.37: N,N-Diethyl-N-{2-[2-(6-methoxybenzo[b]-thiophen-5-yl)ethoxy]ethyl}-amine
 IR(neat)cm$^{-1}$: 2968, 2869, 1469, 1245, 1082.
 NMR(CDCl$_3$)δ: 1.01(6H, t, J=7 Hz), 2.55(4H, q, J=7 Hz), 2.65(2H, t, J=6 Hz), 3.00(2H, t, J=7 Hz), 3.55(2H, t, J=6 Hz), 3.67(2H, t, J=7 Hz), 3.88(3H, s), 7.25(2H, d, J=7 Hz), 7.33(1H, s), 7.59(1H, s).
No.38: N-{2-[2-(4-Fluorobenzo[b]thiophen-5-yl)-ethoxy]ethyl}-N,N-dimethylamine
 IR(neat)cm$^{-1}$: 2863, 1464, 1116.
 NMR(CDCl$_3$)δ: 2.25(6H, s), 2.49(2H, t, J=6 Hz), 3.14(2H, t, J=7 Hz), 3.56(2H, t, J=6 Hz), 3.80(2H, t, J=7 Hz), 6.90(1H, d, J=8 Hz), 7.15(1H, dd, J=5, 8 HZ), 7.40(1H, d, J=5 Hz), 7.47(1H, d, J=5 Hz).
No.39: N,N-Dimethyl-N-{2-[2-(1-naphthyl)ethoxy]-ethyl}-amine
 IR(neat)cm$^{-1}$: 2942, 1116, 777.
 NMR(CDCl$_3$)δ: 2.26(6H, s), 2.51(2H, t, J=6 Hz), 3.39(2H, t, J=7 Hz), 3.58(2H, t, J=6 Hz), 3.79(2H, t, J=7 Hz), 7.3–7.5(4H, m), 7.7–7.9(2H, m), 8.0–8.2(1H, m).

No.40: N,N-Dimethyl-N-{2-[2-(6-methoxybenzo[b]-thiophen-5-yl)ethoxy]ethyl}amine
 IR(neat)cm$^{-1}$: 1467, 1114, 1045.
 NMR(CDCl$_3$)δ: 2.25(6H, s), 2.50(2H, t, J=6 Hz), 3.01(2H, t, J=7 Hz), 3.56(2H, t, J=6 Hz), 3.67(2H, t, J=7 Hz), 3.87(3H, s), 7.20(2H, s), 7.28(1H, s), 7.59(1H, s).
No.41: N,N-Dimethyl-N-{2-[2-(6-methoxy-2-naphthyl)-ethoxy]ethyl}amine
 IR(neat)cm$^{-1}$: 1608, 1265, 1118.
 NMR(CDCl$_3$)δ: 2.25(6H, s), 2.50(2H, t, J=6 Hz), 3.02(2H, t, J=7 Hz), 3.56(2H, t, J=6 Hz), 3.72(2H, t, J=7 Hz), 3.90(3H, s), 7.0–7.4(3H, m), 7.5–7.8(3H, m).
No.42: N-{2-[2-(4-Chlorobenzo[b]thiophen-5-yl)ethoxy]-ethyl}-N,N-dimethylamine
 IR(neat)cm$^{-1}$: 2939, 2862, 1116.
 NMR(CDCl$_3$)δ: 2.26(6H, s), 2.50(2H, t, J=6 Hz), 3.17(2H, t, J=7 Hz), 3.57(2H, t, J=6 Hz), 3.71(2H, t, J=7 Hz), 7.26(1H, d, J=8 Hz), 7.49(2H, s), 7.69(1H, d, J=8 Hz).
No.43: N-{2-[2-(4-Fluorobenzo[b]thiophen-7-yl)ethoxy]-ethyl}-N,N-dimethylamine
 IR(neat)cm$^{-1}$: 2864, 1445, 1117.
 NMR(CDCl$_3$)δ: 2.25(6H, s), 2.49(2H, t, J=6 Hz), 3.05(2H, t, J=7 Hz), 3.56(2H, t, J=6 Hz), 3.70(2H, t, J=7 Hz), 7.0–7.7(4H, m).
No.44: N-{2-[2-(6-Chlorobenzo[b]thiophen-5-yl)-ethoxy]-ethyl}-N,N-dimethylamine
 IR(neat)cm$^{-1}$: 2862, 1436, 1116.
 NMR(CDCl$_3$)δ: 2.25(6H, s), 2.50(2H, t, J=6 Hz), 3.14(2H, t, J=7 Hz), 3.58(2H, t, J=6 Hz), 3.64(2H, t, J=7 Hz), 7.24(1H, d, J=5 Hz), 7.40(1H, d, J=5 Hz), 7.71(1H, s), 7.86(1H, s).
No.45; N,N-Diethyl-N-{2-[2-(6-fluorobenzo[b]-thiophen-7-yl)ethoxy]ethyl}-amine
 IR(neat)cm$^{-1}$: 2967, 1470, 1236, 1114.
 NMR(CDCl$_3$)δ: 0.99(6H, t, J=7 Hz), 2.53(4H, q, J=7 Hz), 2.62(2H, t, J=6 Hz), 3.19(2H, t, J=7 Hz), 3.55(2H, t, J=6 Hz), 3.76(2H, t, J=7 Hz), 7.09(1H, t, J=9 Hz), 7.28(1H, d, J=5 Hz), 7.38(1H, d, J=5 Hz), 7.62(1H, dd, J=5, 9 Hz).
No.46: N-{2-[2-(5,7-Difluorobenzo[b]thiophen-6-yl)ethoxy]ethyl}-N,N-diethylamine
 IR(neat)cm$^{-1}$: 2968, 1404, 1115, 1092.
 NMR(CDCl$_3$)δ: 0.98(6H, t, J=7 Hz), 2.53(4H, q, J=7 Hz), 2.63(2H, t, J=6 Hz), 3.08(2H, t, J=7 Hz), 3.55(2H, t, J=6 Hz), 3.68(2H, t, J=7 Hz), 7.23(1H, d, J=2 Hz), 7.33(1H, d, J=2 Hz), 7.48(1H, d, J=5 Hz).
No.47: N,N-Diethyl-N-{2-[2-(5-methoxybenzo[b]furan-6-yl)-ethoxy]ethyl}-amine
 IR(neat)cm$^{-1}$: 2967, 1465, 1206, 1112.
 NMR(CDCl$_3$)δ: 1.02(6H, t, J=7 Hz), 2.57(4H, q, J=7 Hz), 2.66(2H, t, J=6 Hz), 2.99(2H, t, J=7 Hz), 3.56(2H, t, J=7 Hz), 3.67(2H, t, J=6 Hz), 3.86(3H, s), 6.6–6.8(1H, m), 6.99(1H, s), 7.33(1H, s), 7.5–7.7(1H, m).
No.48: N-[2-(2-Benzo[b]thiophen-5-yl-1-methylethoxy)-ethyl]-N,N-diethylamine
 IR(neat)cm$^{-1}$: 2968, 2930, 1090.
 NMR(CDCl$_3$)δ: 0.98(6H, t, J=7 Hz), 1.15(3H, d, J=6 Hz), 2.52(4H, q, J=7 Hz), 2.60(2H, t, J=6 Hz), 2.88(2H, dd, J=6, 14 Hz), 3.4–3.8(1H, m), 3.56(2H, t, J=7 Hz), 7.20(1H, d, J=8 Hz), 7.27(1H, d, J=5 Hz), 7.41(1H, d, J=5 Hz), 7.65(1H, s), 7.78(1H, d, J=8 Hz).

EXAMPLE 49

In 2.5 mL of ethyl acetate is dissolved 1.06 g of N,N-diethyl-N-{2-[2-(1-naphthyl)ethoxy]ethyl}-amine, to which is added 3.0 mL of a solution of 0.35 g of oxalic acid in ethyl acetate. The resulting mixture is stirred at ambient temperature for 2 hours. The deposited crystal is collected by filtration, washed with ethyl acetate and dried to obtain 1.01 g of N,N-diethyl-N-{2-[2-(1-naphthyl)ethoxy]ethyl}-amine oxalate.

mp: 88–92° C.

IR(KBr)cm$^{-1}$: 3418, 1403, 1113, 720.

NMR(DMSO-d$_6$)δ: 1.10(6H, t, J=7 Hz), 3.02(4H, q, J=7 Hz), 3.16(2H, t, J=5 Hz), 3.33(2H, t, J=6 Hz), 3.72(4H, t, J=6 Hz), 6.4(2H, brs), 7.4–7.6(4H, m), 7.8–8.0(2H, m), 8.0–8.2(1H, m).

EXAMPLES 50–51

Example 49 is repeated to obtain the following compounds.

No.50: N,N-Diethyl-N-{2-[2-(6-methoxybenzo[b]-thiophen-5-yl)ethoxy]ethyl}-amine oxalate mp: 80–83° C.

IR(KBr)cm$^{-1}$: 3424, 2940, 1468, 1245, 1112, 720.

NMR(DMSO-d$_6$)δ: 1.10(6H, t, J=7 Hz), 2.9–3.2(8H, m), 3.6–3.8(4H, m), 3.86(3H, s), 6.9(2H, brs), 7.29(1H, d, J=5 Hz), 7.51(1H, d, J=5 Hz), 7.58(1H, s), 7.66(1H, s).

No.51: N-{2-[2-(4-Fluorobenzo[b]thiophen-5-yl)ethoxy]ethyl}-N,N-dimethylamine oxalate mp: 118–121° C.

IR(KBr)cm$^{-1}$: 3434, 1464, 1116.

NMR(DMSO-d$_6$)δ: 2.67(6H, s), 3.09(2H, t, J=7 Hz), 3.16(2H, t, J=6 Hz), 3.74(2H, t, J=6 Hz), 3.80(2H, t, J=7 Hz), 7.1(2H, brs), 7.11(1H, d, J=7 Hz), 7.31(1H, dd, J=4, 7 Hz), 7.53(1H, d, J=6 Hz), 7.86(1H, d, J=6 Hz).

EXAMPLE 52

In 4.4 mL of ethyl acetate is dissolved 0.87 g of N,N-dimethyl-N-{2-[2-(1-naphthyl)ethoxy]ethyl}-amine, to which is added 1.3 mL of a 3.5 mol/L solution of dry hydrogen chloride in ethyl acetate. The resulting mixture is stirred at ambient temperature for one hour. The deposited crystal is collected by filtration, washed with ethyl acetate and dried to obtain 0.77 g of N,N-dimethyl-N-{2-[2-(1-naphthyl)ethoxy]ethyl}-amine hydrochloride.

mp: 183–184° C.

IR(KBr)cm$^{-1}$: 2628, 1478, 1401, 1128.

NMR(CDCl$_3$)δ: 2.59(3H, s), 2.64(3H, s), 2.9–3.3(2H, m), 3.35(2H, t, J=6 Hz), 3.7–4.0(4H, m), 7.3–8.2(7H, m), 12.5 (1H, brs).

EXAMPLES 53–61

Example 52 is repeated to obtain the following compounds.

No.53: N,N-Dimethyl-N-{2-[2-(6-methoxybenzo[b]thiophen-5-yl)ethoxy]ethyl}-amine hydrochloride mp: 128–132° C.

IR(KBr)cm$^{-1}$: 2964, 1470, 1119.

NMR(CDCl$_3$)δ: 2.71(6H, s), 2.99(2H, t, J=7 Hz), 3.1–3.3 (2H, m), 3.73(2H, t, J=7 Hz), 3.8–4.1(2H, m), 3.89(3H, s), 7.22(2H, s), 7.30(1H, s), 7.57(1H, s), 12.2(1H, brs).

No.54: N,N-Dimethyl-N-{2-[2-(6-methoxy-2-naphthyl)-ethoxy]ethyl}-amine hydrochloride mp: 125–128° C.

IR(KBr)cm$^{-1}$: 3314, 1114, 1024.

NMR(CDCl$_3$)δ: 2.64(6H, s), 3.00(2H, t, J=7 Hz), 3.0–3.2 (2H, m), 3.79(2H, t, J=7 Hz), 3.8–4.0(2H, m), 3.92(3H, s), 7.0–7.4(3H, m), 7.5–7.8(3H, m), 12.6(1H, brs).

No.55: N-{2-[2-(4-Chlorobenzo[b]thiophen-5-yl)ethoxy]-ethyl}-N,N-dimethylamine hydrochloride mp: 92–95° C.

IR(KBr)cm$^{-1}$: 3418, 1471, 1417.

NMR(CDCl$_3$)δ: 2.71(3H, s), 2.76(3H, s), 3.16(2H, t, J=6 Hz), 3.2–3.4(2H, m), 3.78(2H, t, J=6 Hz), 3.8–4.1(2H, m), 7.24(1H, d, J=8 Hz), 7.50(2H, s), 7.71(1H, d, J=8 Hz), 12.6(1H, brs).

No.56: N-{2-[2-(4-Fluorobenzo[b]thiophen-7-yl)ethoxy]-ethyl}-N,N-dimethylamine hydrochloride mp: 67–69° C.

IR(KBr)cm$^{-1}$: 1117, 910, 704.

NMR(CDCl$_3$)δ: 2.68(3H, s), 2.74(3H, s), 2.8–3.3(4H, m), 3.76(2H, t, J=6 Hz), 3.8–4.0(2H, m), 7.0–7.7(4H, m), 12.6 (1H, brs).

No.57: N-{2-[2-(6-Chlorobenzo[b]thiophen-5-yl)ethoxy]-ethyl}-N,N-dimethylamine hydrochloride mp: 105–108° C.

IR(KBr)cm$^{-1}$: 2606, 1434, 1110.

NMR(CDCl$_3$)δ: 2.71(3H, s), 2.76(3H, s), 3.0–3.4(4H, m), 3.79(2H, t, J=7 Hz), 3.8–4.0(2H, m), 7.0–7.6(2H, m), 7.72 (1H, s), 7.87(1H, s), 12.6(1H, brs).

No.58: N,N-Diethyl-N-{2-[2-(6-Fluorobenzo[b]-thiophen-7-yl)ethoxy]ethyl}-amine hydrochloride mp: 71–73.5° C.

IR(KBr)cm$^{-1}$: 3422, 2650, 1469, 1234, 1114.

NMR(CDCl$_3$)δ: 1.24(6H, t, J=7 Hz), 2.9–3.2(8H, m), 3.85(4H, t, J=6 Hz), 7.11(1H, t, J=8 Hz), 7.30(1H, d, J=5 Hz), 7.40(1H, d, J=5 Hz), 7.65(1H, dd, J=5, 8 Hz), 12.0(1H, brs).

No.59: N-{2-[2-(5,7-Difluorobenzo[b]thiophen-6-yl)-ethoxy]ethyl}-N,N-diethylamine hydrochloride mp: 98–100° C.

IR(KBr)cm$^{-1}$: 3422, 2937, 2654, 1404, 1112.

NMR(CDCl$_3$)δ: 1.29(6H, t, J=7 Hz), 2.9–3.1(8H, m), 3.74(2H, t, J=6 Hz), 3.92(2H, t, J=5 Hz), 7.28(1H, d, J=2 Hz), 7.36(1H, d, J=2 Hz), 7.51(1H, d, J=5 Hz), 12.1(1H, brs).

No.60: N,N-Diethyl-N-{2-[2-(5-methoxybenzo[b]furan-6-yl)ethoxy]ethyl}-amine hydrochloride mp: 90–92° C.

IR(KBr)cm$^{-1}$: 2939, 2659, 1470, 1108.

NMR(CDCl$_3$)δ: 1.28(6H, t, J=5 Hz), 2.8–3.3(8H, m), 3.71(2H, t, J=6 Hz), 3.8–4.0(2H, m), 3.87(3H, s), 6.6–6.8 (1H, m), 7.01(1H, s), 7.27(1H, s), 7.59(1H, dd, J=2, 7 Hz).

No.61: N-[2-(2-Benzo[b]thiophen-5-yl-1-ethylethoxy)-ethyl]-N,N-diethylamine hydrochloride mp: 84.5–87° C.

IR(KBr)cm$^{-1}$: 3419, 2972, 2648, 1104.

NMR(CDCl$_3$)δ: 1.0–1.4(6H, m), 1.23(3H, d, J=6 Hz), 2.8–2.9(2H, m), 2.87(2H, d, J=7 Hz), 3.0–3.1(4H, m), 3.6–4.1(3H, m), 7.17(1H, d, J=8 Hz), 7.28(1H, d, J=5 Hz), 7.45(1H, d, J=5 Hz), 7.62(1H, s), 7.80(1H, d, J=8 Hz), 12.0(1H, brs).

EXAMPLE 62

In 8 mL of N,N-dimethylformamide is dissolved 0.80 g of 2-(2-benzo[b]thiophen-5-ylethoxy)ethyl methanesulfonate, to which are added 0.73 mL of dipropylamine and 0.74 g of potassium carbonate. The resulting mixture is stirred at 80° C. for 3 hours. The reaction mixture is introduced into a mixture of water and ethyl acetate, and the organic layer is separated. The organic layer is washed with water and saturated aqueous solution of sodium chloride and dried over anhydrous magnesium sulfate, the solvent is distilled off under reduced pressure, and the residue is purified by column chromatography (eluent:chloroform:methanol= 10:1). Thus, 0.60 of N-[2-(2-benzo[b]thiophen-5-ylethoxy) ethyl]-N,N-dipropylamine is obtained as an oily product.

IR(neat)cm$^{-1}$: 2965, 1459, 1114, 700.

NMR(CDCl$_3$)δ: 0.85(6H, t, J=7 Hz), 1.43(4H, sext, J=7 Hz), 2.41(4H, t, J=7 Hz), 2.64(2H, t, J=6 Hz), 3.00(2H, t, J=7 Hz), 3.53(2H, t, J=6 Hz), 3.70(2H, t, J=7 Hz), 7.20(1H, d, J=8 Hz), 7.27(1H, d, J=5 Hz), 7.41(1H, d, J=5 Hz), 7.66(1H, s), 7.78(1H, d, J=8 Hz).

EXAMPLES 63–66

Example 62 is repeated to obtain the following compounds.

No.63: 2-{[2-(Benzo[b]thiophen-5-ylethoxy)ethyl]-(methyl)amino}-1-ethanol

IR(neat)cm$^{-1}$: 3422, 2863, 1113, 1044.

NMR(CDCl$_3$)δ: 2.29(3H, s), 2.55(2H, t, J=5 Hz), 2.63 (2H, t, J=6 Hz), 2.95(1H, brs), 2.99(2H, t, J=7 Hz), 3.53(2H, t, J=6 Hz), 3.55(2H, t, J=5 Hz), 3.61(2H, t, J=7 Hz), 7.20(1H, d, J=8 Hz), 7.26(1H, d, J=5 Hz), 7.40(1H, d, J=5 Hz), 7.65(1H, s), 7.78(1H, d, J=8 Hz).

No.64: 2-{[2-(2-Benzo[b]thiophen-5-ylethoxy)-1-methylethyl](methyl)amino}-1-ethanol IR(neat)cm$^{-1}$: 3423, 2943, 2863, 1109.

NMR(CDCl$_3$)δ: 0.95(3H, d, J=7 Hz), 2.26(3H, s), 2.61 (2H, t, J=5 Hz), 2.7–3.0(1H, m), 3.00(2H, t, J=7 Hz), 3.33(2H, t, J=5 Hz), 3.50(2H, t, J=5 Hz), 3.68(2H, t, J=7 Hz), 7.21(1H, d, J=8 Hz), 7.28(1H, d, J=5 Hz), 7.42(1H, d, J=5 Hz), 7.67(1H, s), 7.79(1H, d, J=8 Hz).

No.65: N-[2-(2-Benzo[b]thiophen-5-ylethoxy)ethyl]-N-methyl-N-(2-propynyl)amine

IR(neat)cm$^{-1}$: 3292, 2861, 1113, 1050, 755, 703.

NMR(CDCl$_3$)δ: 2.21(1H, t, J=2 Hz), 2.34(3H, s), 2.66 (2H, t, J=6 Hz), 3.01(2H, t, J=7 Hz), 3.39(2H, d, J=2 Hz), 3.56(2H, t, J=6 Hz), 3.71(2H, t, J=7 Hz), 7.21(1H, dd, J=1, 8 Hz), 7.29(1H, d, J=5 Hz), 7.42(1H, d, J=5 Hz), 7.66(1H, d, J=1 Hz), 7.78(1H, d, J=8 Hz).

No.66: 2-{[2-(2-Benzo[b]thiophen-5-ylethoxy)-ethyl](2-hydroxyethyl)amino}-1-ethanol IR(neat)cm$^{-1}$: 3394, 2866, 1670, 1108, 1050, 756, 703.

NMR(CDCl$_3$)δ: 2.6(2H, brs), 2.70(4H, t, J=5 Hz), 2.76 (2H, t, J=6 Hz), 3.01(2H, t, J=7 Hz), 3.51(2H, t, J=6 Hz), 3.57(4H, t, J=5 Hz), 3.73(2H, t, J=7 Hz), 7.22(1H, d, J=8 Hz), 7.29(1H, d, J=5 Hz), 7.42(1H, d, J=5 Hz), 7.67(1H, s), 7.79(1H, d, J=8 Hz).

EXAMPLE 67

In 1 mL of ethyl acetate is dissolved 0.60 g of N-[2-(2-benzo[b]thiophen-5-ylethoxy)ethyl]-N,N-dipropylamine, to which is added 2 mL of a solution of 0.18 g of oxalic acid in ethyl acetate. The resulting mixture is stirred at ambient temperature for 2 hours. The deposited crystal is collected by filtration, washed with ethyl acetate and dried to obtain 0.56 g of N-[2-(2-benzo[b]thiophen-5-ylethoxy)ethyl]-N,N-dipropylamine oxalate.

mp: 93–98° C.

IR(KBr)cm$^{-1}$: 2968, 2631, 1637, 1114, 720.

NMR(CDCl$_3$)δ: 0.84(6H, t, J=7 Hz), 1.4–1.9(4H, m), 2.95(2H, t, J=8 Hz), 2.98(4H, t, J=6 Hz), 3.2–3.4(2H, m), 3.6–4.0(4H, m), 4.4(2H, brs), 7.22(1H, d, J=8 Hz), 7.28(1H, d, J=5 Hz), 7.44(1H, d, J=5 Hz), 7.63(1H, s), 7.79(1H, d, J=8 Hz).

EXAMPLES 68–69

Example 67 is repeated to obtain the following compounds.

No.68: 2-{[2-(2-Benzo[b]thiophen-5-ylethoxy)ethyl]-(methyl)amino}-1-ethanol oxalate mp: 77–81° C.

IR(KBr)cm$^{-1}$: 3394, 2867, 1113, 720.

NMR(DMSO-d$_6$)δ: 2.88(3H, s), 2.8–3.7(6H, m), 3.4–4.0 (6H, m), 5.13(2H, brs), 7.26(1H, d, J=8 Hz), 7.39(1H, d, J=5 Hz), 7.73(1H, d, J=5 Hz), 7.76(1H, s), 7.91(1H, d, J=8 Hz).

No.69 2-{[2-(2-Benzo[b]thiophen-5-ylethoxy)-1-methylethyl](methyl)amino}-1-ethanol oxalate mp: 72–74° C.

IR(KBr)cm$^{-1}$: 3398, 1106, 720.

NMR(DMSO-d$_6$)δ: 1.16(3H, d, J=5 Hz), 2.64(3H, s), 2.8–3.3(5H, m), 3.4–3.9(6H, m), 7.26(1H, d, J=8 Hz), 7.38(1H, d, J=6 Hz), 7.72(1H, d, J=6 Hz), 7.75(1H, s), 7.90(1H, d, J=8 Hz).

EXAMPLE 70

In 2.9 mL of ethyl acetate is dissolved 0.58 g of N-[2-(2-benzo[b]thiophen-5-ylethoxy)ethyl]-N-methyl-N-(2-propynyl)amine, to which is added 0.97 mL of 3.5 mol/L solution of dry hydrogen chloride in ethyl acetate. The resulting mixture is stirred at ambient temperature for one hour and then at 5° C. for one hour. The reaction mixture is diluted with 10 mL of diisopropyl ether. The deposited crystal is collected by filtration, washed with diisopropyl ether and dried to obtain 0.35 g of N-[2-(2-benzo[b]thiophen-5-ylethoxy)ethyl]-N-methyl-N-(2-pripynyl)amine hydrochloride.

mp: 101–102° C.

IR(KBr)cm$^{-1}$: 3173, 2409, 1132, 714.

NMR(DMSO-d$_6$)δ: 2.50(1H, t, J=2 Hz), 2.73(3H, s), 2.96(2H, t, J=7 Hz), 3.2–3.5(2H, m), 3.71(2H, t, J=7 Hz), 3.7–3.9(2H, m), 4.03(2H, d, J=2 Hz), 7.28(1H, d, J=8 Hz), 7.39(1H, d, J=5 Hz), 7.72(1H, d, J=5 Hz), 7.76(1H, s), 7.91(1H, d, J=8 Hz), 11.4(1H, brs).

EXAMPLE 71

Example 70 is repeated to obtain the following compound.

No.71 2-{[2-(2-Benzo[b]thiophen-5-ylethoxy)-ethyl](2-hydroxyethyl)amino}-1-ethanol hydrochloride IR(neat)cm$^{-1}$: 3284, 2876, 1115, 705.

NMR(CDCl$_3$)δ: 1.7(2H, brs), 2.9–3.5(8H, m), 3.7–4.0 (8H, m), 4.7(1H, brs), 7.17(1H, d, J=8 Hz), 7.27(1H, d, J=5 Hz), 7.45(1H, d, J=5 Hz), 7.63(1H, s), 7.80(1H, d, J=8 Hz).

EXAMPLE 72

In 6 mL of N,N-dimethylformamide is dissolved 0.80 g of 5-[2-(3-chloropropyloxy)ethyl]benzo[b]-thiophene, to which are added 0.51 mL of 2-(methylamino)ethanol and 0.87 g of potassium carbonate. The mixture is stirred at 80° C. for 3 hours. The reaction mixture is introduced into a mixture of water and ethyl acetate. The organic layer is separated, washed with water and saturated aqueous solution of sodium chloride and dried over anhydrous magnesium sulfate, the solvent is distilled off under reduced pressure, and the residue is purified by column chromatography (eluent: chloroform:methanol=10:1). Thus, 0.59 g of 2-{[3-(2-benzo[b]thiophen-5-ylethoxy)propyl]-(methyl)amino]-1-ethanol is obtained as an oily product.

IR(neat)cm$^{-1}$: 3408, 2945, 2859, 1111.

NMR(CDCl$_3$)δ: 1.72 (2H, qn, J=7 Hz), 2.21 3H, s), 2.45(2H, t, J=7 Hz), 2.47(2H, t, J=6 Hz), 2.99(2H, t, J=7 Hz), 3.49(2H, t, J=6 Hz), 3.60(2H, t, J=7 Hz), 3.67(2H, t, J=7 Hz), 7.22(1H, d, J=8 Hz), 7.28(1H, d, J=5 Hz), 7.42(1H, d, J=5 Hz), 7.67(1H, s), 7.79(1H, d, J=8 Hz).

EXAMPLES 73–75

Example 72 is repeated to obtain the following compounds.

No.73: 2-{[5-(2-Benzo[b]thiophen-5-ylethoxy)pentyl]-(methyl)amino}-1-ethanol

IR(neat)cm$^{-1}$: 3422, 2938, 2860, 1112.

NMR(CDCl$_3$)v: 1.3–1.7(6H, m), 2.22(3H, s), 2.38(2H, t, J=6 Hz), 2.50(2H, t, J=5 Hz), 2.82(1H, s), 3.00(2H, t, J=7 Hz), 3.44(2H, t, J=6 Hz), 3.57(2H, t, J=5 Hz), 3.67(2H, t, J=7 Hz), 7.21(1H, d, J=8 Hz), 7.28(1H, d, J=5 Hz), 7.42(1H, d, J=5 Hz), 7.67(1H, s), 7.79(1H, d, J=8 Hz).

No.74: 2-(Methyl{2-[2-(6-quinoxalinyl)ethoxy]ethyl}-amino)-1-ethanol

IR(neat)cm$^{-1}$: 3405, 2866, 1113, 1027.

NMR(CDCl$_3$)δ: 2.30(3H, s), 2.57(2H, t, J=6 Hz), 2.64 (2H, t, J=6 Hz), 3.14(2H, t, J=7 Hz), 3.57(4H, t, J=6 Hz), 3.80(2H, t, J=7 Hz), 7.69(1H, d, J=9 Hz), 7.99(1H, s), 8.04(1H, d, J=9 Hz), 8.81(2H, s).

No.75: 2-[{2-[2-(1H-Benzo[d]imidazol-5-yl)ethoxy]ethyl}-(methyl)amino]-1-ethanol IR(neat)cm$^{-1}$: 3180, 1458, 1113, 1041.

NMR(CDCl$_3$)δ: 2.30(3H, s), 2.59(2H, t, J=6 Hz), 2.66 (2H, t, J=6 Hz), 2.97(2H, t, J=6 Hz), 3.3–3.8(6H, m), 7.08(1H, d, J=8 Hz), 7.51(1H, s), 7.55(1H, d, J=8 Hz), 8.00(1H, s).

EXAMPLE 76

In 2 mL of ethyl acetate is dissolved 0.59 g of 2-{[3-(2-benzo[b]thiophen-5-ylethoxy)propyl]-(methyl)amino]-1-ethanol, to which is added 2 ml of a solution of 0.18 g of oxalic acid in ethyl acetate. The resulting mixture is stirred at ambient temperature for 2 hours. The reaction mixture is diluted with 5 mL of diisopropyl ether. The deposited crystal is collected by filtration, washed with ethyl acetate and dried to obtain 0.59 g of 2-{[3-(2-benzo[b]thiophen-5-ylethoxy) propyl]-(methyl)amino}-1-ethanol oxalate.

mp: 83–85° C.

IR(KBr)cm$^{-1}$: 3368, 2866, 1109, 720.

NMR(DMSO-d$_6$)δ: 1.8–2.0(2H, m), 2.70(3H, s), 2.92 (2H, t, J=7 Hz), 3.00(2H, t, J=6 Hz), 3.05(2H, t, J=6 Hz), 3.46(2H, t, J=6 Hz), 3.6–3.8(4H, m), 5.5(2H, brs), 7.25(1H, d, J=8 Hz), 7.39(1H, d, J=5 Hz), 7.72(1H, d, J=5 Hz), 7.75(1H, s), 7.90(1H, d, J=8 Hz).

EXAMPLE 77

Example 76 is repeated to obtain the following compound.

No.77: 2-{[5-(2-Benzo[b]thiophen-5-ylethoxy)pentyl]-(methyl)amino}-1-ethanol oxalate mp: 78.5–80.5° C.

IR(KBr)cm$^{-1}$: 3422, 2937, 2861, 1116, 705.

NMR(DMSO-d$_6$)δ: 1.2–1.6(6H, m), 2.72(3H, s), 2.92 (2H, t, J=7 Hz), 2.99(2H, t, J=7 Hz), 3.08(2H, t, J=6 Hz), 3.40(2H, t, J=6 Hz), 3.62(2H, t, J=7 Hz), 3.70(2H, t, J=7 Hz), 7.24(1H, d, J=8 Hz), 7.39(1H, d, J=5 Hz), 7.72(1H, d, J=5 Hz), 7.72(1H, s), 7.90(1H, d, J=8 Hz).

EXAMPLE 78

In 3 mL of ethanol is dissolved 0.23 g of 2-(methyl{2-[2-(6-quinoxalinyl)ethoxy]ethyl}amino)-1-ethanol, to which is added 0.8 mL of 3.8 mol/L solution of dry hydrogen chloride in ethanol. The mixture is stirred at ambient temperature for one hour. By distilling off the solvent under reduced pressure, there is obtained 0.67 g of 2-(methyl{2-[2-(6-quinoxalinyl)-ethoxy]ethyl}amino)-1-ethanol trihydrochloride as an oily product.

IR(neat)cm$^{-1}$: 3384, 1522, 1113, 1042.

NMR(DMSO-d$_6$)δ: 2.6–4.2(12H, m), 2.77(3H, d, J=5 Hz), 7.85(1H, d, J=9 Hz), 8.02(1H, s), 8.07(1H, d, J=9 Hz), 8.96(2H, s), 10.5(1H, brs).

EXAMPLE 79

Example 70 is repeated to obtain the following compound.

No.79: 2-[{2-[2-(1H-Benzo[d]imidazol-5-yl)ethoxy]-ethyl}-(methyl)amino]-1-ethanol trihydrochloride IR(neat)cm$^{-1}$: 3347, 1449, 1376, 1112.

NMR(DMSO-d$_6$)δ: 2.2–4.2(12H, m), 2.75(3H, s), 7.50 (1H, d, J=9 Hz), 7.76(1H, s), 7.80(1H, d, J=9 Hz), 9.0(1H, brs), 9.62(1H, s), 10.3(1H, brs).

EXAMPLE 80

In 10 mL of N,N-dimethylformamide is dissolved 1.00 g of 2-(2-benzo[b]thiophen-5-ylethoxy)-1-methylethyl methanesulfonate, to which is added 3.3 mL of diethylamine. The mixture thus obtained is stirred in an ampoule at 100° C. for 15 hours. After cooling, the reaction mixture is introduced into a mixture of water and ethyl acetate, pH is adjusted to 2.0 with 6 mol/L hydrochloric acid, and the aqueous layer is separated. Ethyl acetate is added to the aqueous layer, pH is adjusted to 9.5 with 5 mol/AL aqueous solution of sodium hydroxide, and the organic layer is separated. The organic layer is washed with water and saturated aqueous solution of sodium chloride successively and dried over anhydrous magnesium sulfate, the solvent is distilled off under reduced pressure, and the residue is purified by column chromatography (eluent: chloroform:methanol=20:1 to 10:1). Thus, 0.63 g of N-[2-(2-benzo[b]thiophen-5-ylethoxy)-1-methylethyl]-N,N-diethylamine is obtained as an oily product.

IR(neat)cm$^{-1}$: 2967, 2867, 1111.

NMR(CDCl$_3$)δ: 1.00(3H, d, J=6 Hz), 1.01(6H, t, J=7 Hz), 2.51(4H, q, J=7 Hz), 2.8–2.9(2H, m), 2.99(2H, t, J=7 Hz), 3.34(1H, d, J=7 Hz), 3.50(1H, d, J=5 Hz), 3.69(2H, t, J=7 Hz), 7.22(1H, d, J=8 Hz), 7.28(1H, d, J=5 Hz), 7.42(1H, d, J=5 Hz), 7.68(1H, s), 7.79(1H, d, J=8 Hz).

EXAMPLE 81

In 6 mL of N,N-dimethylformamide is dissolved 0.80 g of 5-[2-(3-chloropropyloxy)ethyl]benzo[b]-thiophene, to which is added 3.2 mL of diethylamine. The mixture is stirred in an ampoule at 100° C. for 10 hours. After cooling, the reaction mixture is introduced into a mixture of water and ethyl acetate, pH is adjusted to 1.0 with 6 mol/L hydrochloric acid, and the aqueous layer is separated. Ethyl acetate is added to the aqueous layer, pH is adjusted to 10.0 with 5 mol/L aqueous solution of sodium hydroxide, and the organic layer is separated. The organic layer is washed with water and saturated aqueous solution of sodium chloride and dried over anhydrous magnesium sulfate, the solvent is distilled off under reduced pressure, and the residue is purified by column chromatography (eluent: chloroform:methanol=10:1 to 4:1). Thus, 0.48 g of N-[3-(2-benzo[b]thiophen-5-ylethoxy)propyl]-N,N-diethylamine is obtained as an oily product.

IR(neat)cm$^{-1}$: 2967, 2864, 2800, 1112.

NMR(CDCl$_3$)δ: 0.99(6H, t, J=7 Hz), 1.70(2H, qn, J=7 Hz), 2.49(4H, q, J=7 Hz), 2.99(2H, t, J=7 Hz), 3.48(2H, t, J=7 Hz), 3.67(2H, t, J=7 Hz), 7.21(1H, d, J=8 Hz), 7.28(1H, d, J=5 Hz), 7.41(1H, d, J=5 Hz), 7.66(1H, s), 7.79(1H, d, J=8 Hz).

EXAMPLE 82

Example 81 is repeated to obtain the following compound.

No.82: N-[5-(2-Benzo[b]thiophen-5-ylethoxy)pentyl]-N,N-diethylamine

IR(neat)cm$^{-1}$: 2967, 2935, 2860, 1113.

NMR(CDCl$_3$)δ: 1.01(6H, t, J=7 Hz), 1.3–1.7(6H, m), 2.43(2H, q, J=7 Hz), 2.51(2H, q, J=7 Hz), 2.99(2H, t, J=7 Hz), 3.45(2H, t, J=6 Hz), 3.67(2H, t, J=7 Hz), 7.21(1H, d, J=8 Hz), 7.27(1H, d, J=5 Hz), 7.41(1H, d, J=5 Hz), 7.66(1H, s), 7.79(1H, d, J=8 Hz).

EXAMPLE 83

In 2 mL of ethyl acetate is dissolved 0.46 g of N-[3-(2-benzo[b]thiophen-5-ylethoxy)propyl]-N,N-diethylamine, to which is added 2.5 mL of a solution of 0.15 g of oxalic acid in ethyl acetate. The resulting mixture is stirred at ambient temperature for 2 hours. The deposited crystal is collected by filtration, washed with ethyl acetate and dried to obtain 0.47 g of N-[3-(2-benzo[b]thiophen-5-ylethoxy)propyl]-N,N-diethylamine oxalate.

mp: 87.5–89° C.

IR(KBr)cm$^{-1}$: 2938, 2648, 1112, 706.

NMR(DMSO-d$_6$)δ: 1.10(6H, t, J=7 Hz), 1.7–2.0(2H, m), 2.93(2H, t, J=7 Hz), 3.01(4H, q, J=7 Hz), 3.46(2H, t, J=7 Hz), 3.65(2H, t, J=7 Hz), 4.6(2H, brs), 7.25(1H, d, J=8 Hz), 7.39(1H, d, J=5 Hz), 7.73(1H, d, J=5 Hz), 7.73(1H, s), 7.91(1H, d, J=8 Hz).

EXAMPLE 84

In 3.0 mL of ethyl acetate is dissolved 0.62 g of N-[5-(2-benzo[b]thiophen-5-ylethoxy)pentyl]-N,N-diethylamine, to which is added 1.1 mL of 3.6 mol/L solution of dry hydrogen chloride in ethyl acetate. The mixture is stirred at ambient temperature for one hour. The reaction mixture is diluted with 5 mL of diisopropyl ether and stirred at ambient temperature for one hour. The deposited crystal is collected by filtration, washed with ethyl acetate and dried to obtain 0.55 g of N-[5-(2-benzo[b]thiophen-5-ylethoxy)pentyl]-N,N-diethylamine hydrochloride.

mp: 138.5–140° C.

IR(KBr)cm$^{-1}$: 2933, 2594, 2503, 1104.

NMR(DMSO-d$_6$)δ: 1.18(6H, t, J=7 Hz), 1.3–1.6(6H, m), 2.9–3.1(8H, m), 3.40(2H, t, J=7 Hz), 3.63(2H, t, J=7 Hz), 7.25(1H, d, J=8 Hz), 7.39(1H, d, J=5 Hz), 7.72(1H, d, J=5 Hz), 7.72(1H, s), 7.90(1H, d, J=8 Hz), 10.2(1H, brs).

EXAMPLE 85

(1) In 10 mL of methylene chloride is dissolved 1.20 g of 2-(2-benzo[b]thiophen-7-ylethoxy)-acetic acid. The solution is cooled to 5° C., 0.49 mL of oxalyl chloride and 0.1 mL of N,N-dimethylformamide are added thereto, and the resulting mixture is stirred at ambient temperature for 1.5 hours. The mixture is then cooled to 5° C., 2.6 mL of diethylamine is added, and the resulting mixture is stirred at ambient temperature for 2 hours. Water is added to the reaction mixture, pH is adjusted to 1.0 with 2 mol/L hydrochloric acid, and organic layer is separated. The organic layer is washed with saturated aqueous solution of sodium chloride and dried over anhydrous magnesium sulfate, and the solvent is distilled off under reduced pressure. Thus, 1.36 g of 2-(2-benzo[b]thiophen-7-ylethoxy)-N,N-diethylacetamide is obtained as an oily product.

The following compounds are obtained in the same manner as above.

N-Benzyl-2-[2-(6-fluorobenzo[b]thiophen-5-ylethoxy)]-N-methylacetamide

NMR(CDCl$_3$)δ: 2.80(1.5H, s), 2.87(1.5H, s), 3.08(2H, t, J=7 Hz), 3.80(2H, t, J=7 Hz), 4.21(2H, s), 4.40(1H, s), 4.55(1H, s), 7.0–7.8(9H, m).

2-[2-(6-Fluorobenzo[b]thiophen-5-ylethoxy)-N,N-dimethylacetamide 2-(2-Benzo[b]thiophen-4-ylethoxy)-N,N-diethylacetamide NMR(CDCl$_3$)δ: 1.07(6H, t, J=7 Hz), 3.0–3.6(6H, m), 3.85(2H, t, J=7 Hz), 4.13(2H, s), 7.2–7.4(2H, m), 7.46(2H, s), 7.75(1H, dd, J=2, 6 Hz).

2-(2-Benzo[b]thiophen-6-ylethoxy)-N,N-diethylacetamide

NMR(CDCl$_3$)δ: 1.09(6H, t, J=7 Hz), 3.0–3.6(6H, m), 3.81(2H, t, J=7 Hz), 4.13(2H, s), 7.1–7.3(2H, m), 7.38(1H, d, J=5 Hz), 7.73(1H, s), 7.73(1H, d, J=8 Hz).

2-(2-Benzo[b]thiophen-5-ylethoxy)-N-ethyl-N-ethylacetamide

NMR(CDCl$_3$)δ: 1.07(3H, t, J=7 Hz), 2.82(1.5H, s), 2.88(1.5H, s), 3.05(2H, t, J=7 Hz), 3.1–3.6(2H, m), 3.80(2H, t, J=7 Hz), 4.13(2H, s), 7.21(1H, d, J=8 Hz), 7.27(1H, d, J=5 Hz), 7.42(1H, d, J=5 Hz), 7.67(1H, s), 7.79(1H, d, J=8 Hz).

2-(3-Benzo[b]thiophen-5-ylpropoxy)-N,N-diethylacetamide

NMR(CDCl$_3$)δ: 0.9–1.5(6H, m), 1.8–2.2(2H, m), 2.6–3.0(2H, m), 3.1–3.8(2H, m), 3.52(4H, q, J=6 Hz), 4.13(2H, s), 7.18(1H, d, J=8 Hz), 7.27(1H, d, J=5 Hz), 7.42(1H, d, J=5 Hz), 7.63(1H, s), 7.78(1H, d, J=8 Hz).

2-[2-(2,3-Dihydro-1,4-benzodioxin-6-yl)ethoxy]-N,N-diethylacetamide

NMR(CDCl$_3$)δ: 1.13(6H, t, J=7 Hz), 2.83(2H, t, J=7 Hz), 3.1–3.6(4H, m), 3.70(4H, t, J=7 Hz), 4.12(2H, s), 4.23(4H, s), 6.6–6.9(3H, m).

2-[2-(2,3-Dihydro-1H-inden-5-yl)ethoxy]-N,N-diethylacetamide

NMR(CDCl$_3$)δ: 1.12(6H, t, J=7 Hz), 2.04(2H, qn, J=7 Hz), 2.7–3.0(6H, m), 3.1–3.5(4H, m), 3.73(2H, t, J=7 Hz), 4.13(2H, s), 6.96(1H, d, J=8 Hz), 7.09(1H, s), 7.13(1H, d, J=8 Hz).

2-(2-Benzo[b]thiophen-4-ylethoxy)-N,N-dimethylacetamide

NMR(CDCl$_3$)δ: 2.80(3H, s), 2.89(3H, s), 3.29(2H, t, J=7 Hz), 3.85(2H, t, J=7 Hz), 4.13(2H, s), 7.1–7.4(2H, m), 7.46(2H, s), 7.7–7.9(1H, m).

N$^1$-[2-(Dimethylamino)ethyl]-N$^1$-methyl-2-(2-enzo[b]thiophen-5-ylethoxy)-acetamide IR(neat)cm$^{-1}$: 3504, 2940, 2861, 2821, 2770, 1651, 1104, 703.

NMR(CDCl$_3$)δ: 2.17(3H, s), 2.2–2.6(2H, m), 2.23(6H, s), 3.05(2H, t, J=7 Hz), 3.1–3.6(2H, m), 3.80(2H, t, J=7 Hz), 4.14(2H, s), 7.21(1H, dd, J=2, 8 Hz), 7.26(1H, d, J=5 Hz), 7.41(1H, d, J=5 Hz), 7.67(1H, s), 7.78(1H, d, J=8 Hz).

N$^1$-(2-Hydroxyethyl)-N$^1$-methyl-2-[2-(2-methyl-1,3-benzothiazol-5-yl)ethoxy]-acetamide IR(neat)cm$^{-1}$: 3396, 2930, 1638, 1106.

NMR(CDCl$_3$)δ: 1.30(1H, t, J=7 Hz), 2.81(3H, s), 2.95(3H, s), 3.05(2H, t, J=7 Hz), 3.2–4.0(4H, m), 3.80(2H, t, J=7 Hz), 4.0–4.4(2H, m), 7.21(1H, d, J=8 Hz), 7.71(1H, d, J=8 Hz), 7.80(1H, s).

(2) In 14 mL of tetrahydrofuran is dissolved 1.36 g of 2-(2-benzo[b]thiophen-7-ylethoxy)-N,N-diethylacetamide. The solution is cooled to 5° C., and 14 mL of 1 mol/L solution of borane-tetrahydrofuran complex in tetrahydrofuran is dropwise added thereto. The resulting mixture is stirred at ambient temperature overnight, and then 5.00 mL of 6 mol/L hydrochloric acid is dropwise added, and the resulting mixture is heated under reflux for 30 minutes. After cooling, water and ethyl acetate are added to the reaction mixture, pH is adjusted to 9 with 5 mol/L aqueous solution of sodium hydroxide, and the organic layer is separated. The organic layer is washed with saturated aqueous solution of sodium chloride and dried over anhydrous magnesium sulfate, the solvent is distilled off under reduced pressure, and the residue is purified by column chromatography (eluent: chloroform:methanol=10:1) to obtain 1.10 g of N-[2-(2-benzo[b]thiophen-7-ylethoxy)ethyl]-N,N-diethylamine as an oily product.

IR(neat)cm$^{-1}$: 2968, 1458, 1116, 794.

NMR(CDCl$_3$)δ: 1.01(6H, t, J=7 Hz), 2.55(4H, q, J=7 Hz), 2.65(2H, t, J=6 Hz), 3.18(2H, t, J=7 Hz), 3.56(2H, t, J=6 Hz), 3.83(2H, t, J=7 Hz), 7.0–7.6(4H, m), 7.68(1H, dd, J=1, 7 Hz).

EXAMPLES 86–96

Example 85 is repeated to obtain the following compounds.

No.86: N-Benzyl-N-{2-[2-(6-fluorobenzo[b]thiophen-5-yl)ethoxy]ethyl}-N-methylamine IR(neat)cm$^{-1}$: 2929, 1458, 1257, 1116, 747.

NMR(CDCl$_3$)δ: 2.43(3H, s), 2.93(2H, t, J=5 Hz), 3.04 (2H, t, J=7 Hz), 3.76(2H, t, J=7 Hz), 3.82(2H, t, J=5 Hz), 3.87(2H, s), 7.21(2H, d, J=6 Hz), 7.34(5H, s), 7.50(1H, d, J=10 Hz), 7.66(1H, d, J=7 Hz).

No.87: N-{2-[2-(6-Fluorobenzo[b]thiophen-5-yl)-ethoxy]ethyl}-N,N-dimethylamine

IR(neat)cm$^{-1}$: 2942, 2864, 2819, 2771, 1458, 1116.

NMR(CDCl$_3$)δ: 2.25(6H, s), 2.50(2H, t, J=6 Hz), 3.04 (2H, t, J=7 Hz), 3.57(2H, t, J=6 Hz), 3.71(2H, t, J=7 Hz), 7.24(1H, d, J=5 Hz), 7.36(1H, d, J=5 Hz), 7.51(1H, d, J=10 Hz), 7.67(1H, d, J=7 Hz).

No.88: N-[2-(2-Benzo[b]thiophen-4-ylethoxy)ethyl]-N,N-diethylamine

IR(neat)cm$^{-1}$: 2968, 2869, 1114, 759.

NMR(CDCl$_3$)δ: 1.01(6H, t, J=7 Hz), 2.55(4H, q, J=7 Hz), 2.64(2H, t, J=6 Hz), 3.24(2H, t, J=7 Hz), 3.55(2H, t, J=6 Hz), 3.75(2H, t, J=7 Hz), 7.2–7.3(2H, m), 7.45(2H, s), 7.74(1H, dd, J=2, 7 Hz).

No.89: N-[2-(2-Benzo[b]thiophen-6-ylethoxy)ethyl]-N,N-diethylamine

IR(neat)cm$^{-1}$: 2968, 2868, 1113, 818.

NMR(CDCl$_3$)δ: 1.01(6H, t, J=7 Hz), 2.55(4H, q, J=7 Hz), 2.65(2H, t, J=6 Hz), 3.01(2H, t, J=7 Hz), 3.54(2H, t, J=6 Hz), 3.70(2H, t, J=7 Hz), 7.22(1H, dd, J=1, 8 Hz), 7.28(1H, d, J=5 Hz), 7.36(1H, d, J=5 Hz), 7.72(1H, d, J=1Hz), 7.73(1H, d, J=8 Hz).

No.90: N-[2-(2-Benzo[b]thiophen-5-ylethoxy)ethyl]-N-ethyl-N-methylamine

IR(neat)cm$^{-1}$: 2969, 2864, 1115, 1052, 702.

NMR(CDCl$_3$)δ: 1.04(3H, t, J=7 Hz), 2.25(3H, s), 2.45 (2H, q, J=7 Hz), 2.57(2H, t, J=6 Hz), 3.01(2H, t, J=7 Hz), 3.56(2H, t, J=6 Hz), 3.70(2H, t, J=7 Hz), 7.21(1H, d, J=8 Hz), 7.27(1H, d, J=5 Hz), 7.41(1H, d, J=5 Hz), 7.67(1H, s), 7.78(1H, d, J=8 Hz).

No.91: N-[2-(3-Benzo[b]thiophen-5-ylpropyl)ethyl]-N,N-diethylamine

No.92: N-{2-[2-(2,3-Dihydro-1,4-benzodioxin-6-yl)ethoxy]ethyl}-N,N-diethylamine

IR(neat)cm$^{-1}$: 2871, 1509, 1286, 1070.

NMR(CDCl$_3$)δ: 1.02(6H, t, J=7 Hz), 2.56(2H, q, J=7 Hz), 2.64(4H, t, J=7 Hz), 2.73(2H, q, J=7 Hz), 3.52(4H, t, J=7 Hz), 4.23(4H, s), 6.73(3H, s).

No.93: N-{2-[2-(2,3-Dihydro-1H-inden-5-yl)-ethoxy]ethyl}-N,N-diethylamine

IR(neat)cm$^{-1}$: 2966, 1114, 819, 754.

NMR(CDCl$_3$)δ: 1.02(6H, t, J=7 Hz), 2.05(2H, qn, J=7 Hz), 2.57(4H, q, J=7 Hz), 2.65(2H, t, J=6 Hz), 2.88(6H, t, J=7 Hz), 3.55(2H, t, J=6 Hz), 3.64(2H, t, J=7 Hz), 6.98(1H, d, J=8 Hz), 7.10(1H, s), 7.14(1H, d, J=8 Hz).

No.94: N-[2-(2-Benzo[b]thiophen-4-ylethoxy)ethyl]-N,N-dimethylamine

IR(neat)cm$^{-1}$: 2942, 1458, 1116, 760.

NMR(CDCl$_3$)δ: 2.25(6H, s), 2.49(2H, t, J=6 Hz), 3.26 (2H, t, J=7 Hz), 3.56(2H, t, J=6 Hz), 3.76(2H, t, J=7 Hz), 7.0–7.7(4H, m), 7.74(1H, dd, J=2, 6 Hz).

No.95: N$^1$-2-(2-Benzo[b]thiophen-5-ylethoxy)ethyl]-N$^1$,N$^2$,N$^2$-trimethyl-1,2-ethanediamine IR(neat)cm$^{-1}$: 3361, 2941, 2858, 2815, 2758, 1463, 1113, 701.

NMR(CDCl$_3$)δ: 2.22(6H, s), 2.28(3H, s), 2.3–2.7(4H, m), 2.61(2H, t, J=5 Hz), 3.00(2H, t, J=7 Hz), 3.56(2H, t, J=6 Hz), 3.69(2H, t, J=7 Hz), 7.19(1H, d, J=8 Hz), 7.26(1H, d, J=5 Hz), 7.41(1H, d, J=5 Hz), 7.65(1H, s), 7.78(1H, d, J=8 Hz).

No.96: 2-(Methyl{2-[2-(2-methyl-1,3-benzothiazol-5-yl)ethoxy]ethyl}amino)-1-ethanol IR(neat)cm$^{-1}$: 3387, 2942, 2864, 1459, 1114, 1043, 754.

NMR(CDCl$_3$)δ: 2.30(3H, s), 2.57(2H, t, J=6 Hz), 2.64 (2H, t, J=6 Hz), 2.81(3H, s), 3.01(2H, t, J=7 Hz), 3.4–3.6 (4H, m), 3.71(2H, t, J=7 Hz), 7.21(1H, d, J=8 Hz), 7.71(1H, d, J=8 Hz), 7.81(1H, s).

EXAMPLE 97

In 10 mL of ethyl acetate is dissolved 1.10 g of N-[2-(2-benzo[b]thiophen-7-ylethoxy)ethyl]-N,N-diethylamine, to which is added 10 mL of a solution of 0.39 g of oxalic acid in ethyl acetate. The resulting mixture is stirred at ambient temperature for 2 hours. The deposited crystal is collected by filtration, washed with ethyl acetate, and dried to obtain 1.14 g of N-[2-(2-benzo[b]thiophen-7-ylethoxy)ethyl]-N,N-diethylamine oxalate.

mp: 75–76° C.

IR(KBr)cm$^{-1}$: 3422, 2652, 1399, 1114, 798, 720.

NMR(DMSO-d$_6$)δ: 1.08(6H, t, J=7 Hz), 2.99(4H, q, J=7 Hz), 3.0–3.3(4H, m), 3.6–3.8(2H, m), 3.84(2H, t, J=7 Hz), 7.2–7.9(5H, m), 8.2(2H, brs).

EXAMPLES 98–103

Example 97 is repeated to obtain the following compounds.

No.98: N-Benzyl-N-{2-[2-(6-fluorobenzo[b]thiophen-5-yl)ethoxy]ethyl}-N-methylamine oxalate mp: 96–98° C.

IR(KBr)cm$^{-1}$: 3445, 2938, 2636, 1456, 1118.

NMR(DMSO-d$_6$)δ: 2.50(3H, s), 2.8–3.2(4H, m), 3.5–3.9 (4H, m), 4.05(2H, s), 7.36(1H, d, J=5 Hz), 7.38(5H, s), 7.69(1H, d, J=5 Hz), 7.85(1H, d, J=10 Hz), 7.89(1H, d, J=3 Hz), 9.0(2H, brs).

No.99: N-{2-[2-(6-Fluorobenzo[b]thiophen-5-yl)ethoxy]ethyl}-N,N-dimethylamine oxalate mp: 120–126° C.

IR(KBr)cm$^{-1}$: 2956, 2679, 1123, 720.

NMR(DMSO-d$_6$)δ: 2.69(6H, s), 2.98(2H, t, J=7 Hz), 3.18(2H, t, J=5 Hz), 3.71(4H, t, J=7 Hz), 7.40(1H, d, J=5 Hz), 7.71(1H, d, J=5 Hz), 7.87(1H, d, J=11Hz), 7.90(1H, d, J=4 Hz), 9.1(2H, brs).

No.100: N-[2-(2-Benzo[b]thiophen-4-ylethoxy)ethyl]-N,N-diethylamine oxalate
mp: 79–82° C.
IR(KBr)cm$^{-1}$: 3431, 1405, 1112, 720.
NMR(DMSO-d$_6$)δ: 1.09(6H, t, J=7 Hz), 2.99(4H, q, J=7 Hz), 3.19(2H, t, J=7 Hz), 3.7–3.8(6H, m), 4.4(2H, brs), 7.2–7.3(2H, m), 7.5–7.9(3H, m).

No.101: N-[2-(2-Benzo[b]thiophen-6-ylethoxy)ethyl]-N,N-diethylamine oxalate
mp: 53–58° C.
IR(KBr)cm$^{-1}$: 2945, 2655, 1634, 1112, 720.
NMR(DMSO-d$_6$)δ: 1.08(6H, t, J=7 Hz), 2.8–3.3(8H, m), 3.77(4H, brt, J=6 Hz), 6.1(2H, brs), 7.26(1H, d, J=8 Hz), 7.40(1H, d, J=5 Hz), 7.67(1H, d, J=5 Hz), 7.80(1H, d, J=8 Hz), 7.85(1H, s).

No.102: N-[2-(2-Benzo[b]thiophen-5-ylethoxy)ethyl]-N-ethyl-N-methylamine oxalate
mp: 102–104° C.
IR(KBr)cm$^{-1}$: 2944, 2664, 1635, 1404, 1114, 720.
NMR(DMSO-d$_6$)δ: 1.10(3H, t, J=7 Hz), 2.64(3H, s), 2.8–3.3(6H, m), 3.6–3.9(4H, m), 7.28(1H, d, J=8 Hz), 7.39(1H, d, J=5 Hz), 7.73(1H, d, J=5 Hz), 7.76(1H, s), 7.91(1H, d, J=8 Hz), 9.3(2H, brs).

No.103: N-[2-(3-Benzo[b]thiophen-5-ylpropyl)ethyl]-N,N-diethylamine oxalate
mp: 58–60° C.
IR(KBr)cm$^{-1}$: 3446, 2943, 2650, 1114.
NMR(DMSO-d$_6$)δ: 1.19(6H, t, J=7 Hz), 1.6–2.1(2H, m), 2.75(2H, t, J=8 Hz), 3.08(4H, t, J=7 Hz), 3.22(2H, t, J=6 Hz), 3.45(2H, t, J=6 Hz), 3.69(2H, t, J=4 Hz), 7.22(1H, d, J=8 Hz), 7.39(1H, d, J=5 Hz), 7.42(2H, brs), 7.69(1H, s), 7.72(1H, d, J=5 Hz), 7.90(1H, d, J=8 Hz).

EXAMPLE 104

In 1.9 mL of ethyl acetate is dissolved 0.38 g of N-{2-[2-(2,3-dihydro-1,4-benzodioxin-6-yl)ethoxy]ethyl}-N,N-diethylamine, to which is added 0.51 mL of a 3.5 mol/L solution of dry hydrogen chloride in ethyl acetate. The mixture is stirred at ambient temperature for one hour and then at 5° C. for one hour. The deposited crystal is collected by filtration, washed with ethyl acetate, and dried. Thus, 0.29 g of N-{2-[2-(2,3-dihydro-1,4-benzodioxin-6-yl)ethoxy]ethyl}-N,N-diethylamine hydrochloride.
mp: 120–123° C.
IR(KBr)cm$^{-1}$: 3447, 2940, 1508, 1286, 1068.
NMR(DMSO-d$_6$)δ: 1.16(6H, t, J=7 Hz), 2.70(2H, t, J=7 Hz), 3.0–3.2(6H, m), 3.59(2H, t, J=7 Hz), 3.73(2H, t, J=5 Hz), 4.19(4H, s), 6.71(3H, s), 10.2(1H, brs).

EXAMPLES 105–107

Example 103 is repeated to obtain the following compounds.

No.105: N-{2-[2-(2,3-Dihydro-1H-inden-5-yl)ethoxy]ethyl}-N,N-diethylamine hydrochloride
mp: 104–105° C.
IR(KBr)cm$^{-1}$: 2935, 2659, 1111, 1034, 818.
NMR(DMSO-d$_6$)δ: 1.16(6H, t, J=7 Hz), 1.8–2.2(2H, m), 2.7–3, 9(16H, m), 6.97(1H, d, J=8 Hz), 7.10(1H, s), 7.15(1H, d, J=8 Hz), 10.4(1H, brs).

No.106: N-[2-(2-Benzo[b]thiophen-4-ylethoxy)ethyl]-N,N-dimethylamine hydrochloride
mp: 165–167° C.
IR(KBr)cm$^{-1}$: 2628, 1413, 1126, 768.
NMR(DMSO-d$_6$)δ: 2.68(6H, s), 3.0–3.6(4H, m), 3.6–4.0(4H, m), 7.2–7.5(2H, m), 7.61(1H, d, J=6 Hz), 7.77(1H, d, J=6 Hz), 7.87(1H, d, J=6 Hz), 10.5(1H, brs).

No.107: N$^1$-[2-(2-Benzo[b]thiophen-5-ylethoxy)ethyl]-N$^1$,N$^2$,N$^2$-trimethyl-1,2-ethanediamine dihydrochloride
mp: 228–230° C.
IR(KBr)cm$^{-1}$: 3446, 2633, 2468, 1473, 1119, 702.
NMR(DMSO-d$_6$)δ: 2.79(3H, s), 2.8–4.1(12H, m), 3.38 (6H, s), 7.30(1H, dd, J=1, 8 Hz), 7.40(1H, d, J=6 Hz), 7.73(1H, d, J=6 Hz), 7.77(1H, s), 7.91(1H, d, J=8 Hz).

EXAMPLE 108

(1) In 8 mL of methylene chloride is dissolved 0.80 g of 2-[2-(6-methoxybenzo[b]thiophen-5-yl)ethoxy]-acetic acid, to which are added 1.38 mL of triethylamine and 0.22 g of imidazole. The mixture is cooled to 5° C., to which is dropwise added a mixture of 0.24 mL of thionyl chloride and 8 mL of methylene chloride. The resulting mixture is stirred at the same temperature as above for one hour. The reaction mixture is cooled to −60° C., 0.47 mL of triethylamine and 0.31 mL of 2-(methylamino)-ethanol are added thereto, and the resulting mixture is stirred at the same temperature as above for one hour and the at ambient temperature for 1.5 hours. Water is added to the reaction mixture, pH is adjusted to 1.0 with 6 mol/L hydrochloric acid, and the organic layer is separated. The organic layer is washed with saturated aqueous solution of sodium chloride and dried over anhydrous magnesium sulfate, and the solvent is distilled off under reduced pressure. Thus, 0.93 g of N$^1$-(2-hydroxyethyl)-N$^1$-methyl-2-[2-(6-methoxybenzo[b]thiophen-5-yl)ethoxy]-acetamide is obtained as an oily product.
NMR(CDCl$_3$)δ: 2.94(3H, s), 3.04(2H, t, J=7 Hz), 3.4–3.6 (2H, m), 3.77(4H, t, J=7 Hz), 3.88(3H, s), 4.1–4.2(2H, m), 7.21(1H, s), 7.26(1H, s), 7.29(1H, s), 7.60(1H, s).

The following compounds are obtained in the same manner as above.

N$^1$-(2-Hydroxyethyl)-N$^1$-methyl-2-[2-(6-fluorobenzo[b]-thiophen-5-yl)ethoxy]-acetamide
IR(neat)cm$^{-1}$: 1659, 1644, 1456, 1107.
NMR(CDCl$_3$)δ: 2.94(3H, s), 3.07(2H, t, J=7 Hz), 3.3–3.9 (7H, m), 4.1–4.3(2H, m), 7.1–7.8(4H, m).

N$^1$-(2-Hydroxyethyl)-N$^1$-methyl-2-[2-(2-methylbenzo[b]-thiophen-5-yl)ethoxy]-acetamide N$^1$-Ethyl-N$^1$-(2-hydroxyethyl)-2-(2-benzo[b]thiophen-5-ylethoxy)-acetamide
NMR(CDCl$_3$)δ: 1.09(3H, t, J=7 Hz), 3.09(2H, q, J=7 Hz), 3.30(2H, t, J=7 Hz), 3.46(2H, t, J=7 Hz), 3.81(4H, t, J=7 Hz), 4.17(2H, s), 7.21(1H, d, J=8 Hz), 7.28(1H, d, J=5 Hz), 7.42(1H, d, J=5 Hz), 7.68(1H, s), 7.79(1H, d, J=8 Hz).

N$^1$-Benzyl-N$^1$-(2-hydroxyethyl)-2-(2-benzo[b]thiophen-5-ylethoxy)-acetamide
NMR(CDCl$_3$)δ: 2.9–3.1(2H, m), 3.3–3.9(6H, m), 4.1–4.3 (2H, m), 4.4–4.6(2H, m), 7.1–7.3(7H, m), 7.42(1H, d, J=5 Hz), 7.64(1H, s), 7.77(1H, d, J=8 Hz).

N$^1$-(2-Hydroxyethyl)-N$^1$-methyl-2-(3-benzo[b]thiophen-5-ylpropoxy)-acetamide
NMR(CDCl$_3$)δ: 1.99(2H, qn, J=7 Hz), 2.5–3.2(4H, m), 3.06(3H, s), 3.55(2H, t, J=7 Hz), 3.5–3.9(2H, m), 4.0–4.4 (2H, m), 7.17(1H, d, J=8 Hz), 7.27(1H, d, J=5 Hz), 7.42(1H, d, J=5 Hz), 7.63(1H, s), 7.78(1H, d, J=8 Hz).

(2) In 8 mL of tetrahydrofuran is dissolved 0.93 g of N$^1$-(2-hydroxyethyl)-N$^1$-methyl-2-[2-(6-methoxybenzo[b]-thiophen-5-yl)ethoxy]-acetamide. The solution is cooled to 5° C., and 6 mL of 1 mol/L solution of borane-tetrahydrofuran complex in tetrahydrofuran is dropwise added thereto. After stirring the mixture at ambient temperature overnight, 1.5 mL of 6 mol/L hydrochloric acid is dropwise added, and the resulting mixture is heated under reflux for 30 minutes. After cooling, water and ethyl acetate are added to the reaction mixture, pH is adjusted to 9.5 with 5 mol/L aqueous solution of sodium hydroxide, and the organic layer is separated. The organic layer is washed with saturated aqueous solution of sodium chloride and dried over anhydrous magnesium sulfate, the solvent is distilled off under reduced pressure, and the residue is purified by column chromatography (eluent: chloroform:methanol= 10:1 to 5:1). Thus, 0.67 g of 2-[{2-[2-(6-methoxybenzo[b]thiophen-5-yl)ethoxy]-ethyl}(methyl)amino]-1-ethanol is obtained as an oily product.

IR(neat)cm$^{-1}$: 3423, 2940, 2865, 1468, 1045.

NMR(CDCl$_3$)δ: 2.31(3H, s), 2.57(2H, t, J=6 Hz), 2.64 (2H, t, J=6 Hz), 3.00(2H, t, J=7 Hz), 3.56(4H, t, J=5 Hz), 3.67(2H, t, J=7 Hz), 3.88(3H, s), 7.23(2H,

EXAMPLES 109–113

Example 108 is repeated to obtain the following compounds.

No.109: 2-[{2-[2-(6-Fluorobenzo[b]thiophen-5-yl)ethoxy]-ethyl}(methyl)amino]-1-ethanol IR(neat)cm$^{-1}$: 3422, 2868, 1457, 1113.

NMR(CDCl$_3$)δ: 2.29(3H, s), 2.4–2.8(5H, m), 3.02(2H, t, J=7 Hz), 3.4–3.9(6H, m), 7.2–7.8(4H, m).

No.110: 2-(Methyl{2-]2-(2-methylbenzo[b]thiophen-5-yl)ethoxy]ethyl}amino)-1-ethanol IR(neat)cm$^{-1}$: 3398, 2862, 1113, 1040.

NMR(CDCl$_3$)δ: 2.31(3H, s), 2.56(3H, s), 2.57(2H, t, J=6 Hz), 2.70(2H, t, J=6 Hz), 2.96(2H, t, J=7 Hz), 3.54(2H, t, J=6 Hz), 3.56(2H, t, J=6 Hz), 3.68(2H, t, J=7 Hz), 6.91(1H, s), 7.09(1H, d, J=8 Hz), 7.48(1H, s), 7.64(1H, d, J=8 Hz).

No.111: 2-[[2-(2-Benzo[b]thiophen-5-ylethoxy)ethyl]-(ethyl)amino]-1-ethanol

IR(neat)cm$^{-1}$: 3409, 2921, 2864, 1112.

NMR(CDCl$_3$)δ: 1.02(3H, t, J=7 Hz), 2.5–2.8(6H, m), 3.00(2H, t, J=7 Hz), 3.53(4H, t, J=6 Hz), 3.70(2H, t, J=7 Hz), 7.21(1H, d, J=8 Hz), 7.27(1H, d, J=5 Hz), 7.42(1H, d, J=5 Hz), 7.66(1H, s), 7.79(1H, d, J=8 Hz).

No.112: 2-[[2-(2-Benzo[b]thiophen-5-ylethoxy)ethyl]-(benzyl)amino]-1-ethanol

IR(neat)cm$^{-1}$: 3448, 2863, 1111, 1051, 700.

NMR(CDCl$_3$)δ: 2.67(2H, t, J=5 Hz), 2.73(2H, t, J=5 Hz), 2.99(2H, t, J=7 Hz), 3.50(2H, t, J=5 Hz), 3.53(2H, t, J=5H), 3.6–3.7(4H, m), 7.2–7.3(7H, m), 7.42(1H, d, J=5 Hz), 7.66(1H, s), 7.79(1H, d, J=8 Hz).

No.113: 2-[[2-(3-Benzo[b]thiophen-5-ylpropyl)ethyl]-(methyl)amino]-1-ethyanol

IR(neat)cm$^{-1}$: 3422, 2942, 2861, 1115.

NMR(CDCl$_3$)δ: 1.94(2H, qn, J=7 Hz), 2.35(3H, s), 2.60 (2H, t, J=6 Hz), 2.66(2H, t, J=6 Hz), 2.82(2H, t, J=7 Hz), 3.46(2H, t, J=6 Hz), 3.53(2H, t, J=6 Hz), 3.58(2H, t, J=7 Hz), 7.19(1H, d, J=8 Hz), 7.27(1H, d, J=5 Hz), 7.42(1H, d, J=5 Hz), 7.63(1H, s), 7.78(1H, d, J=8 Hz).

EXAMPLE 114

In 1 mL of ethyl acetate is dissolved 0.59 g of 2-[{2-[2-(6-methoxybenzo[b]thiophen-5-yl)ethoxy]-ethyl}-(methyl)amino]-1-ethanol, to which is added 2 mL of a solution of 0.17 g of oxalic acid in ethyl acetate. The mixture is stirred at ambient temperature for 2 hours. The deposited crystal is collected by filtration, washed with ethyl acetate and dried to obtain 0.60 g of 2-[{2-[2-(6-methoxybenzo[b]thiophen-5-yl)ethoxy]ethyl}-(methyl)amino]-1-ethyanol oxalate.

mp: 82.5–85° C.

IR(KBr)cm$^{-1}$: 3366, 1469, 1244, 720.

NMR(DMSO-d$_6$)δ: 2.71(3H, s), 2.91(2H, t, J=7 Hz), 3.07(2H, t, J=6 Hz), 3.23(2H, t, J=6 Hz), 3.65(6H, t, J=7 Hz), 3.86(3H, s), 6.2(2H, brs), 7.29(1H, d, J=5 Hz), 7.51(1H, d, J=5 Hz), 7.56(1H, s), 7.66(1H, s).

EXAMPLES 115–119

Example 114 is repeated to obtain the following compounds.

No.115: 2-[{2-[2-(6-Fluorobenzo[b]thiophen-5-yl)ethoxy]ethyl}(methyl)amino]-1-ethanol oxalate mp: 96–99° C.

IR(KBr)cm$^{-1}$: 3284, 1460, 1404, 1127.

NMR(DMSO-d$_6$)δ: 2.4–3.4(10H, m), 3.6–4.0(6H, m), 5.8(2H, brs), 7.4–8.0(4H, m).

No.116: 2-(Methyl{2-[2-(2-methylbenzo[b]thiophen-5-yl)ethoxy]ethyl}amino)-1-ethanol oxalate mp: 73–75° C.

IR(KBr)cm$^{-1}$: 3274, 2928, 1404, 1115.

NMR(DMSO-d$_6$)δ: 2.55(3H, s), 2.6–3.4(6H, m), 2.70 (3H, s), 3.4–3.9(6H, m), 6.0(2H, brs), 7.06(1H, s), 7.17(1H, d, J=8 Hz), 7.57(1H, s), 7.75(1H, d, J=8 Hz).

No.117: 2-[[2-(2-Benzo[b]thiophen-5-ylethoxy)ethyl]-(ethyl)amino]-1-ethanol oxalate mp: 53–56° C.

IR(KBr)cm$^{-1}$: 3365, 1636, 1120, 720.

NMR(CDCl$_3$)δ: 1.13(3H, t, J=7 Hz), 2.9–3.4(8H, m), 3.70(6H, t, J=7 Hz), 7.16(1H, d, J=8 Hz), 7.25(1H, d, J=5 Hz), 7.42(1H, d, J=5 Hz), 7.62(1H, s), 7.78(1H, d, J=8 Hz), 8.1(2H, brs).

No.118: 2-[[2-(2-Benzo[b]thiophen-5-ylethoxy)ethyl]-(benzyl)amino]-1-ethanol oxalate mp: 104–105.5° C.

IR(KBr)cm$^{-1}$: 3365, 1119, 720, 700.

NMR(CDCl$_3$)δ: 3.00(4H, t, J=6 Hz), 3.3–3.4(2H, m), 3.78(6H, t, J=6 Hz), 4.21(2H, s), 7.1–7.3(7H, m), 7.41(1H, d, J=5 Hz), 7.65(1H, s), 7.77(1H, d, J=8 Hz), 8.6(2H, brs).

No.119: 2-[[2-(3-Benzo[b]thiophen-5-ylpropyl)-ethyl](methyl)amino]-1-ethanol oxalate mp: 67–69° C.

IR(KBr)cm$^{-1}$: 3382, 2945, 2867, 1112.

NMR(DMSO-d$_6$)δ: 1.8–1.9(2H, m), 2.7–2.8(2H, m), 2.79 (3H, s), 3.15(2H, t, J=5 Hz), 3.23(2H, t, J=5 Hz), 3.45(2H, t, J=6 Hz), 3.7–3.8(4H, m), 7.22(1H, d, J=8 Hz), 7.39(1H, d, J=5 Hz), 7.69(1H, s), 7.72(1H, d, J=5 Hz), 7.90(1H, d, J=8 Hz).

EXAMPLE 120

(1) In 8 mL of N,N-dimethylformamide is dissolved 0.76 g of 2-benzo[b]thiophen-6-yl-1-ethanol, to which are added, at an ice-cooled temperature, 1.25 g of potassium tert-butoxide and 2.67 g of N$^1$-methyl-N$^1$-[2-(trityloxy)ethyl]-2-chloroacetamide. The mixture is stirred at the same temperature as above for 30 minutes, and then at ambient temperature for 2 hours. Ethyl acetate and water are added to the reaction mixture, and the organic layer is separated. The solvent is distilled off under reduced pressure, and the residue is purified by column chromatography (eluent: n-hexane:ethyl acetate=5:1 to 3:1). Thus, 2.07 g of N$^1$-methyl-N$^1$-[2-(trityloxy)ethyl]-2-(2-benzo[b]thiophen-6-yethoxy)-acetamide as an oily product.

IR(neat)cm$^{-1}$: 2935, 1659, 759, 707.

NMR(CDCl$_3$)δ: 2.80(3/2H, s), 2.98(3/2H, s), 2.9–3.1(2H, m), 3.2–3.4(2H, m), 3.4–3.6(2H, m), 3.76(2H, t, J=7 Hz), 4.1–4.3(2H, m), 7.1–7.5(18H, m), 7.6–7.8(2H, m).

The following compounds are obtained in the same manner as above.

$N^1$-Methyl-$N^1$-[2-(trityloxy)ethyl]-2-(2-benzo[b]-thiophen-4-ylethoxy)-acetamide IR(neat)cm$^{-1}$: 3006, 1654, 758, 707.

NMR(CDCl$_3$)δ: 2.80(3/2H, s), 2.94(3/2H, s), 3.2–3.3(4H, m), 3.4–3.6(2H, m), 3.7–3.8(2H, m), 4.1–4.3(2H, m), 7.1–7.4(21H, m), 7.6–7.8(2H, m).

$N^1$-Methyl-$N^1$-[2-(trityloxy)ethyl]-2-[2-(5-methoxybenzo-[b]furan-6-yl)ethoxy]-acetamide IR(neat)cm$^{-1}$: 2933, 1650, 1464, 1109.

NMR(CDCl$_3$)δ: 2.8–3.9(8H, m), 3.04(3/2H, s), 3.82(3H, s), 3.84(3/2H, s), 4.1–4.4(2H, m), 6.6–6.8(1H, m), 6.98(1H, s), 7.1–7.7(17H, m).

(2) In 20 mL of tetrahydrofuran is dissolved 2.07 g of $N^1$-methyl-$N^1$-[2-(trityloxy)ethyl]-2-(2-benzo[b]-thiophen-6-ylethoxy)-acetamide. The solution is cooled to 5° C., and 7.5 mL of 1 mol/L solution of borane-tetrahydrofuran complex in tetrahydrofuran is dropwise added thereto. After stirring the mixture at ambient temperature overnight, 1.9 mL of 6 mol/L hydrochloric acid is dropwise added, and the resulting mixture is heated under reflux for one hour. After cooling, water and ethyl acetate are added to the reaction mixture, pH is adjusted to 10 with 5 mol/L aqueous solution of sodium hydroxide, and the organic layer is separated. The organic layer is washed with saturated aqueous solution of sodium chloride and dried over anhydrous magnesium sulfate. The solvent is distilled off under reduced pressure, and the residue is purified by column chromatography (eluent: chloroform:methanol=30:1 to 20:1) to obtain 0.54 g of 2-[[2-(2-benzo[b]thiophen-6-ylethoxy)ethyl](methyl)amino]-1-ethanol as an oily product.

IR(neat)cm$^{-1}$: 3408, 2864, 1113, 1041.

NMR(CDCl$_3$)δ: 2.31(3H, s), 2.56(2H, t, J=5 Hz), 2.64(2H, t, J=6 Hz), 3.01(2H, t, J=7 Hz), 3.55(4H, t, J=6 Hz), 3.70(2H, t, J=7 Hz), 7.2–7.4(3H, m), 7.7–7.8(2H, m).

EXAMPLES 121–122

Example 120(2) is repeated to obtain the following compounds.

No.121: 2-[[2-(2-Benzo[b]thiophen-4-yolethoxy)ethyl]-(methyl)amino]-1-ethanol

IR(neat)cm$^{-1}$: 3408, 2868, 1113, 760.

NMR(CDCl$_3$)δ: 2.30(3H, s), 2.56(2H, t, J=6 Hz), 2.63(2H, t, J=6 Hz), 3.24(2H, t, J=7 Hz), 3.54(2H, t, J=6 Hz), 3.56(2H, t, J=6 Hz), 3.75(2H, t, J=7 Hz), 7.25(2H, dd, J=2, 5 Hz), 7.46(2H, s), 7.76(1H, dd, J=2, 7 Hz).

No.122: 2-[{2-[2-(5-Methoxybenzo[b]furan-6-yl)ethoxy]ethyl}(methyl)amino]-1-ethanol IR(neat)cm$^{-1}$: 2943, 2864, 1464, 1111.

NMR(CDCl$_3$)δ: 2.31(3H, s), 2.58(2H, t, J=6 Hz), 2.65(2H, t, J=5 Hz), 2.99(2H, t, J=7 Hz), 3.4–3.8(6H, m), 3.85(3H, s), 6.6–6.8(1H, m), 6.98(1H, d, J=2 Hz), 7.2–7.4(1H, m), 7.59(1H, dd, J=2, 8 Hz).

EXAMPLE 123

In 4.25 mL of ethyl acetate is dissolved 0.85 g of 2-{[2-(2-benzo[b]thiophen-4-ylethoxy)ethyl]-(methyl)amino}-1-ethanol, to which is added 1.1 mL of 3.6 mol/L solution of dry hydrogen chloride in ethyl acetate. The mixture is stirred at ambient temperature for one hour and then at 5° C. for one hour. The reaction mixture is diluted with 10 mL of diisopropyl ether, and the deposited crystal is collected by filtration, washed with diisopropyl ether and dried. Thus, 0.81 g of 2-[[2-(2-benzo[b]thiophen-4-ylethoxy)ethyl](methyl)-amino)-1-ethanol hydrochloride is obtained.

mp: 84–87° C.

IR(KBr)cm$^{-1}$: 3232, 1116, 760.

NMR(CDCl$_3$)δ: 2.64(3/2H, s), 2.69(3/2H, s), 2.8–3.0(2H, m), 3.22(4H, t, J=6 Hz), 3.7–3.9(6H, m), 7.24(1H, dd, J=2, 7 Hz), 7.29(1H, t, J=7 Hz), 7.45(2H, s), 7.75(1H, dd, J=2, 7 Hz), 11.2(1H, brs).

EXAMPLE 124

In a mixture of 0.21 mL of 6 mol/L hydrochloric acid and 1 mL of water is dissolved 0.37 g of 2-[[2-(2-(5-methoxybenzo[b]furan-6-yl)ethoxy]ethyl}-(methyl)amino]-1-ethanol. The resulting solution is frozen and water is distilled off therefrom under reduced pressure. Thus, 0.40 g of 2-[{2-[2-(5-methoxybenzo[b]furan-6-yl)ethoxy]-ethyl}(methyl)amino]-1-ethanol hydrochloride is obtained as an oily product.

IR(neat)cm$^{-1}$: 3358, 1468, 1428, 1130.

NMR(CDCl$_3$)δ: 2.6–2.9(3H, m), 2.97(2H, t, J=6 Hz), 3.0–3.7(6H, m), 3.71(2H, t, J=6 Hz), 3.8–4.0(3H, m), 3.86(3H, s), 6.6–6.8(1H, m), 7.00(1H, s), 7.28(1H, s), 7.59(1H, dd, J=2, 8 Hz), 11.2(1H, brs).

EXAMPLE 125

(1) In a mixture of 4.8 mL of tert-butanol and 1.2 mL of N,N-dimethylformamide is dissolved 0.60 g of 2-(2-fluorobenzo[b]thiophen-5-yl)-1-ethanol, to which are added, at an ice-cooled temperature, 0.45 g of potassium tert-butoxide and 1.81 g of $N^1$-methyl-$N^1$-[2-(trityloxy)ethyl]-2-chloroacetamide. The resulting mixture is stirred at the same temperature as above for 30 minutes and then at ambient temperature for 2 hours. Ethyl acetate and water are added to the reaction mixture, and the organic layer is separated. The solvent is distilled off under reduced pressure. To the residue are added 6 mL of ethanol, 0.6 mL of water and 0.29 g of p-toluenesulfonic acid monohydrate, and the resulting mixture is stirred at ambient temperature overnight. Ethyl acetate and water are added to the reaction mixture, and the organic layer is separated. The organic layer is washed with water and saturated aqueous solution of sodium chloride successively and dried over anhydrous magnesium sulfate, the solvent is distilled off under reduced pressure, and the residue is purified by column chromatography (eluent: chloroform:methanol=50:1 to 30:1). Thus, 0.74 g of $N^1$-(2-hydroxyethyl)-$N^1$-methyl-2-[2-(2-fluorobenzo[b]-thiophen-5-yl)ethoxy]-acetamide is obtained as an oily product.

IR(neat)cm$^{-1}$: 3405, 2936, 1647, 1106.

NMR(CDCl$_3$)δ: 2.93(3H, s), 3.00(2H, t, J=7 Hz), 3.4–3.6(2H, m), 3.79(4H, t, J=7 Hz), 4.1–4.3(2H, m), 6.65(1H, d, J=3 Hz), 7.1–7.3(1H, m), 7.4–7.8(2H, m).

The following compounds are obtained in the same manner as above.

$N^1$-(2-Hydroxyethyl)-$N^1$-methyl-2-[2-(6-fluorobenzo[b]thiophen-7-yl)ethoxy]-acetamide IR(neat)cm$^{-1}$: 3397, 1646, 1470, 1106.

NMR(CDCl$_3$)δ: 2.88(3H, s), 3.24(2H, t, J=7 Hz), 3.46(2H, t, J=5 Hz), 3.6–3.8(2H, m), 3.87(2H, t, J=7 Hz), 4.1–4.3(2H, m), 7.15(1H, dd, J=9, 19 Hz), 7.29(1H, d, J=5 Hz), 7.39(1H, d, J=5 Hz), 7.64(1H, dd, J=5, 9 Hz).

$N^1$-(2-Hydroxyethyl)-$N^1$-methyl-2-[2-(5,7-difluorobenzo[b]thiophen-6-yl)ethoxy]-acetamide IR(neat)cm$^{-1}$: 3405, 2937, 2878, 1638, 1107.

NMR(CDCl$_3$)δ: 2.96(3H, s), 3.12(2H, t, J=7 Hz), 3.4–3.6(2H, m), 3.78(4H, t, J=7 Hz), 4.1–4.3(2H, m), 7.24(1H, d, J=3 Hz), 7.34(1H, d, J=3 Hz), 7.49(1H, d, J=5 Hz).

$N^1$-(2-Hydroxyethyl)-$N^1$-methyl-2-(2-benzo[b]thiophen-7-ylethoxy)-acetamide

IR(neat)cm$^{-1}$: 3396, 2932, 1654, 1459, 1105, 703.

NMR(CDCl$_3$)δ: 2.86(3H, s), 3.1–4.1(5H, m), 3.22(2H, t, J=7 Hz), 3.92(2H, t, J=7 Hz), 4.20(2H, d, J=6 Hz), 7.1–7.6 (4H, m), 7.70(1H, dd, J=2, 7 Hz).

$N^1$-(2-Hydroxyethyl)-$N^1$-methyl-2-[2-(1-naphthyl)-ethoxy]-acetamide

NMR(CDCl$_3$)δ: 2.85(3H, s), 3.2–3.6(4H, m), 3.6–4.0(2H, m), 3.87(2H, t, J=7 Hz), 4.1–4.4(2H, m), 7.2–7.6(4H, m), 7.6–8.0(2H, m), 8.0–8.2(1H, m).

$N^1$-(2-Hydroxyethyl)-$N^1$-methyl-2-[2-(6-fluoro-7-hydroxybenzo[b]thiophen-5-yl)ethoxy]-acetamide NMR(CDCl$_3$)δ: 2.8–3.2(2H, m), 2.88(3H, s), 3.2–4.0(6H, m), 4.0–4.6(2H, m), 6.9–7.6(3H, m).

$N^1$-(2-Hydroxyethyl)-$N^1$-methyl-2-{2-[6-fluoro-7-(methylthio)-benzo[b]thiophen-5-yl]ethoxy}-acetamide IR(neat)cm$^{-1}$: 3405, 2927, 1643, 1427, 1259, 1107.

NMR(CDCl$_3$)δ: 2.53(3H, s), 2.94(3H, s), 3.08(2H, t, J=7 Hz), 3.2–4.0(4H, m), 3.81(2H, t, J=7 Hz), 4.1–4.3(2H, m), 7.25(1H, dd, J=2, 5 Hz), 7.41(1H, d, J=5 Hz), 7.65(1H, d, J=7 Hz).

$N^1$-(2-Hydroxyethyl)-$N^1$-methyl-2-[2-(6-fluoro-7-methoxybenzo[b]thiophen-5-yl)ethoxy]-acetamide IR(neat)cm$^{-1}$: 3404, 2935, 1654, 1465, 1358, 1108.

NMR(CDCl$_3$)δ: 2.95(3H, s), 3.07(2H, t, J=7 Hz), 3.2–4.1 (4H, m), 3.80(2H, t, J=7 Hz), 4.11(3H, d, J=2 Hz), 4.1–4.4 (2H, m), 7.22(1H, d, J=5 Hz), 7.30(1H, d, J=5 Hz), 7.39(1H, d, J=6 Hz).

$N^1$-(2-Hydroxyethyl)-$N^1$-methyl-2-[2-(6-fluoro-7-methylbenzo[b]thiophen-5-yl)ethoxy]-acetamide IR(neat)cm$^{-1}$: 3399, 2934, 1654, 1458, 1107.

NMR(CDCl$_3$)δ: 2.16(3H, s), 2.45(3H, d, J=2 Hz), 2.8–3.2 (4H, m), 3.4–3.6(2H, m), 3.80(2H, t, J=7 Hz), 4.1–4.3(2H, m), 7.24(1H, d, J=5 Hz), 7.36(1H, d, J=5 Hz), 7.53(1H, d, J=6 Hz).

$N^1$-(2-Hydroxyethyl)-$N^1$-methyl-2-(2-benzo[b]furan-5-ylethoxy)-acetamide

IR(neat)cm$^{-1}$: 3397, 2935, 1648, 1469, 1108, 1030.

NMR(CDCl$_3$)δ: 2.91(3H, s), 2.6–3.2(1H, m), 3.02(2H, t, J=7 Hz), 3.2–3.6(2H, m), 3.70(2H, t, J=7 Hz), 3, 78(2H, t, J=7 Hz), 4.1–4.3(2H, m), 6.71(1H, d, J=2 Hz), 7.13(1H, dd, 2, 8 Hz), 7.32(1H, d, J=8 Hz), 7.45(1H, d, J=2 Hz), 7.59(1H, d, J=2 Hz).

(2) In 7 mL of tetrahydrofuran is dissolved 0.70 g of $N^1$-(2-hydroxyethyl)-$N^1$-methyl-2-[2-(2-fluorobenzo[b] thiophen-5-yl)ethoxy]-acetamide. The solution is cooled to 5° C., to which is dropwise added 6.7 mL of 1 mol/L solution of borane-tetrahydrofuran complex in tetrahydrofuran. The resulting mixture is stirred at ambient temperature overnight, 1.5 mL of 6 mol/L hydrochloric acid is dropwise added, and the resulting mixture is heated under reflux for one hour. After cooling, water and ethyl acetate are added to the reaction mixture, pH is adjusted to 10.5 with 5 mol/L aqueous solution of sodium hydroxide, and the organic layer is separated. The organic layer is washed with saturated aqueous solution of sodium chloride and dried over anhydrous magnesium sulfate, the solvent is distilled off under reduced pressure, and the residue is purified by column chromatography (eluent: chloroform:methanol=10:1 to 5:1) to obtain 0.58 g of 2-[{2-[2-(2-fluorobenzo[b]thiophen-5-yl)ethoxy]ethyl}(methyl)amino]-1-ethanol as an oily product.

IR(neat)cm$^{-1}$: 3422, 2864, 1579, 1451, 1113.

NMR(CDCl$_3$)δ: 2.31(3H, s), 2.57(2H, t, J=6 Hz), 2.64 (2H, t, J=6 Hz), 2.95(2H, t, J=7 Hz), 3.54(2H, t, J=6 Hz), 3.56(2H, t, J=6 Hz)3.68(2H, t, J=7 Hz), 6.65(1H, d, J=2 Hz), 7.1–7.4(1H, m), 7.4–7.9(2H, m).

EXAMPLES 126–134

Example 125(2) is repeated to obtain the following compounds.

No.126: 2-[{2-[2-(6-Fluorobenzo[b]thiophen-7-yl)-ethoxy] ethyl}(methyl)amino]-1-ethanol IR(neat)cm$^{-1}$: 3420, 2868, 1469, 1235.

NMR(CDCl$_3$)δ: 2.27(3H, s), 2.53(2H, t, J=6 Hz), 2.62 (2H, t, J=6 Hz), 3.19(2H, t, J=7 Hz), 3.55(2H, t, J=6 Hz), 3.56(2H, t, J=6 Hz), 3.77(2H, t, J=7 Hz), 7.10(1H, dd, J=9, 10 Hz), 7.29(1H, d, J=5 Hz), 7.39(1H, d, J=5 Hz), 7.63(1H, dd, J=5, 9 Hz).

No.127: 2-[{2-[2-(5,7-Difluorobenzo[b]thiophen-6-yl) ethoxy]ethyl}(methyl)amino]-1-ethanol IR(neat)cm$^{-1}$: 3394, 2868, 1114.

NMR(CDCl$_3$)δ: 2.28(3H, s), 2.54(2H, t, J=5 Hz), 2.63 (2H, t, J=6 Hz), 3.09(2H, t, J=7 Hz), 3.54(2H, t, J=5 Hz), 3.56(2H, t, J=6 Hz), 3.68(2H, t, J=7 Hz), 7.25(1H, d, J=5 Hz), 7.34(1H, d, J=3 Hz), 7.48(1H, d, J=5 Hz).

No.128: 2-{[2-(2-Benzo[b]thiophen-7-ylethoxy)ethyl]-(methyl)amino}-1-ethanol

IR(neat)cm$^{-1}$: 3413, 2865, 1460, 1116, 796, 702.

NMR(CDCl$_3$)δ: 2.28(3H, s), 2.54(2H, t, J=6 Hz), 2.63 (2H, t, J=6 Hz), 2.8(1H, brs), 3.18(2H, t, J=7 Hz), 3.55(4H, t, J=6 Hz), 3.82(2H, t, J=7 Hz), 7.1–7.5(4H, m), 7.69(1H, dd, J=2, 7 Hz).

No.129: 2-(Methyl{2-[2-(1-naphthyl)ethoxy]ethyl}-amino)-1-ethanol

IR(neat)cm$^{-1}$: 3420, 2868, 1113, 778.

NMR(CDCl$_3$)δ: 2.30(3H, s), 2.56(2H, t, J=6 Hz), 2.62 (2H, t, J=6 Hz), 3.4–3.9(8H, m), 7.2–7.9(4H, m), 7.8–8.0 (2H, m), 8.0–8.2(1H, m).

No.130: 6-Fluoro-5-(2-{2-[(2-hydroxyethyl)(methyl)-amino]-ethoxy}ethyl)-benzo[b]thiophen-7-ol NMR(CDCl$_3$)δ: 2.37(3H, s), 2.5–2.9(4H, m), 2.96(2H, t, J=7 Hz), 3.4–3.8(6H, m), 7.11(1H, d, J=6 Hz), 7.16(1H, d, J=5 Hz), 7.32(1H, d, J=5 Hz).

No.131: 2-[(2-{2-[6-Fluoro-7-(methylthio)-benzo[b] thiophen-5-yl]ethoxy}ethyl)(methyl)amino]-1-ethanol IR(neat)cm$^{-1}$: 3422, 2868, 1427, 1114, 1040, 755.

NMR(CDCl$_3$)δ: 2.30(3H, s), 2.54(3H, s), 2.4–2.9(4H, m), 3.04(2H, t, J=7 Hz), 3.4–3.8(2H, m), 3.56(2H, t, J=6 Hz), 3.71(2H, t, J=7 Hz), 7.29(1H, dd, J=2, 6 Hz), 7.41(1H, d, J=6 Hz), 7.63(1H, d, J=6 Hz).

No.132: 2-[{2-[2-(6-Fluoro-7-methoxybenzo[b]thiophen-5-yl)-ethoxy]ethyl}(methyl)amino]-1-ethanol IR(neat)cm$^{-1}$: 3408, 2867, 1464, 1114, 1041.

NMR(CDCl$_3$)δ: 2.30(3H, s), 2.4–2.9(4H, m), 3.03(2H, dt, J=1, 7 Hz), 3.3–3.8(2H, m), 3.56(2H, t, J=6 Hz), 3.71(2H, t, J=7 Hz), 4.11(3H, d, J=2 Hz), 7.22(1H, d, J=5 Hz), 7.35(1H, d, J=5 Hz), 7.36(1H, d, J=7 Hz).

No.133: 2-[{2-[2-(6-Fluoro-7-methylbenzo[b]thiophen-5-yl)-ethoxy]ethyl}(methyl)amino]-1-ethanol IR(neat)cm$^{-1}$: 3397, 2868, 1458, 1115, 1044.

NMR(CDCl$_3$)δ: 2.33(3H, s), 2.47(3H, d, J=2 Hz), 2.5–2.8 (4H, m), 3.01(2H, t, J=7 Hz), 3.56(2H, t, J=5 Hz), 3.67(2H, t, J=5 Hz), 3.70(2H, t, J=7 Hz), 7.25(1H, d, J=5 Hz), 7.36(1H, d, J=5 Hz), 7.51(1H, d, J=7 Hz).

No.134: 2-{[2-(2-Benzo[b]furan-5-ylethoxy)ethyl]-(methyl)amino}-1-ethanol

IR(neat)cm$^{-1}$: 3422, 2865, 1467, 1110, 1031.

NMR(CDCl$_3$)δ: 2.31(3H, s), 2.4–3.2(1H, m), 2.57(2H, t, J=6 Hz), 2.64(2H, t, J=6 Hz), 2.97(2H, t, J=7 Hz), 3.54(2H, t, J=6 Hz), 3.56(2H, t, J=6 Hz), 3.68(2H, t, J=7 Hz), 6.71(1H, d, J=2 Hz), 7.13(1H, dd, J=2, 9 Hz), 7.31(1H, d, J=9 Hz), 7.44(1H, d, J=2 Hz), 7.59(1H, d, J=2 Hz).

EXAMPLE 135

In 1 mL of ethyl acetate is dissolved 0.58 g of 2-[{2-[2-(2-fluorobenzo[b]thiophen-5-yl)ethoxy]-ethyl}-(methyl) amino]-1-ethanol, to which is added 1 mL of a solution of 0.18 g of oxalic acid in ethyl acetate. The mixture is stirred at ambient temperature for 2 hours. The deposited crystal is collected by filtration, washed with ethyl acetate and dried to obtain 0.61 g of 2-[{2-[2-(2-fluorobenzo[b]-thiophen-5-yl)ethoxy]ethyl}(methyl)amino]-1-ethanol oxalate.

mp: 77–80° C.

IR(KBr)cm$^{-1}$: 3393, 1579, 1450, 1113.

NMR(CDCl$_3$)δ: 2.79(3H, s), 2.93(2H, t, J=7 Hz), 3.11 (2H, t, J=5 Hz), 3.31(2H, t, J=5 Hz), 3.6–3.9(6H, m), 6.66(1H, d, J=2 Hz), 6.8(2H, brs), 7.17(1H, d, J=8 Hz), 7.43(1H, s), 7.58(1H, d, J=8 Hz).

EXAMPLE 136

In 2.9 mL of ethyl acetate is dissolved 0.48 g of 2-[{2-[2-(6-fluorobenzo[b]thiophen-7-yl)ethoxy]ethyl}-(methyl) amino]-1-ethanol, to which is added 0.57 mL of 3.6 mol/L solution of dry hydrogen chloride in ethyl acetate. The mixture is stirred at ambient temperature for one hour. The reaction mixture is diluted with 5 mL of diisopropyl ether and stirred at ambient temperature for one hour. The deposited crystal is collected by filtration, washed with ethyl acetate and dried to obtain 0.45 g of 2-[{2-[2-(6-fluorobenzo[b]thiophen-7-yl)ethoxy]ethyl}(methyl)-amino]-1-ethanol hydrochloride.

mp: 69–72° C.

IR(KBr)cm$^{-1}$: 3253, 1469, 1116, 811.

NMR(CDCl$_3$)δ: 2.71(3H, s), 3.1–3.2(2H, m), 3.19(2H, t, J=7 Hz), 3.26(2H, t, J=6 Hz), 3.85(6H, t, J=7 Hz), 4.7(1H, brs), 7.10(1H, dd, J=9, 10 Hz), 7.30(1H, d, J=5 Hz), 7.40 (1H, d, J=5 Hz), 7.65(1H, dd, J=5, 9 Hz).

EXAMPLES 137–138

Example 136 is repeated to obtain the following compounds.

No.137: 2-[{2-[2-(5,7-Difluorobenzo[b]thiophen-6-yl) ethoxy]ethyl}(methyl)amino]-1-ethanol hydrochloride mp: 95.5–97.5° C.

IR(KBr)cm$^1$: 3272, 1405, 1129, 1093.

NMR(CDCl$_3$)δ: 2.81(3H, s), 3.0–3.4(6H, m), 3.75(2H, t, J=6 Hz), 3.8–4.0(4H, m), 4.6(1H, brs), 7.27(1H, d, J=5 Hz), 7.36(1H, d, J=2 Hz), 7.51(1H, d, J=5 Hz).

No.138: 2-{[2-(2-Benzo[b]thiophen-7-yletoxy)ethyl]-(methyl)amino]-1-ethanol hydrochloride mp: 74–76° C.

IR(KBr)cm$^{-1}$: 3383, 1459, 1106, 798, 707.

NMR(CDCl$_3$)δ: 2.67(3H, s), 2.8–3.5(6H, m), 3.5–4.1(6H, m), 4.8(1H, brs), 7.1–7.6(4H, m), 7.71(1H, d, J=7 Hz).

EXAMPLE 139

(1) In 2.4 mL of acetone is suspended 0.38 g of sodium formate, to which is added 0.37 mL of pivaloyl chloride. The mixture is stirred at ambient temperature for 2 hours. Then, at an ice-cooled temperature, 4 mL of a solution of 0.50 g of 2-{[2-(2-benzo[b]thiophen-5-yletoxy)ethyl]-amino}-1-propanol in acetone is added, and the resulting mixture is stirred at ambient temperature for 2 hours. Water and ethyl acetate are added to the reaction mixture, pH is adjusted to 8.5 with 2 mol/L aqueous solution of sodium hydroxide, and the organic layer is separated. The organic layer is washed with saturated aqueous solution of sodium chloride and dried over anhydrous magnesium sulfate, the solvent is distilled off under reduced pressure, and the residue is purified by column chromatography (eluent: chloroform). Thus, 0.46 g of N-[2-(2-benzo[b]thiophen-5-yletoxy) ethyl]-N-(2-hydroxy-1-methylethyl)-formamide (is obtained as an oily product.

IR(neat)cm$^{-1}$: 3423, 2935, 2870, 1655, 1421, 1110, 703.

NMR(CDCl$_3$)δ: 1.05(3H, d, J=6 Hz), 2.97(2H, t, J=7 Hz), 3.1–4.4(10H, m), 7.16(1H, dd, J=2, 8 Hz), 7.26(1H, d, J=5 Hz), 7.41(1H, d, J=5 Hz), 7.62(1H, s), 7.78(1H, d, J=8 Hz), 8.11(1H, s).

The following compounds are obtained in the same manner as above.

N-[2-(2-Benzo[b]thiophen-5-yletoxy)ethyl]-N-(2-hydroxypropyl)-formamide

IR(neat)cm$^{-1}$: 3405, 2867, 1655, 1115.

NMR(CDCl$_3$)δ: 1.0–1.2(3H, m), 3.0–3.1(4H, m), 3.3–3.4 (1H, m), 3.4–3.6(2H, m), 3.6–3.8(5H, m), 7.21(1H, d, J=8 Hz), 7.28(1H, d, J=5 Hz), 7.43(1H, d, J=5 Hz), 7.65(1H, s), 7.80(1H, d, J=8 Hz), 8.04(1/2H, s), 8.12(1/2H, s).

N-[2-(2-Benzo[b]thiophen-5-yletoxy)ethyl]-N-(3-hydroxypropyl)-formamide

IR(neat)cm$^{-1}$: 3421, 2938, 2868, 1652, 1436, 1117, 704.

NMR(CDCl$_3$)δ: 1.5–1.9(2H, m), 2.97(2H, t, J=7 Hz), 3.2–3.9(10H, m), 7.19(1H, d, J=8 Hz), 7.29(1H, d, J=5 Hz), 7.43(1H, d, J=5 Hz), 7.65(1H, s), 7.80(1H, d, J=8 Hz), 8.09(1H, s).

N-[2-(2-Benzo[b]thiophen-5-yletoxy)ethyl]-N-(2-methoxyethyl)-formamide

IR(neat)cm$^{-1}$: 3504, 2931, 2867, 1668, 1436, 1117, 704.

NMR(CDCl$_3$)δ: 2.96(2H, t, J=7 Hz), 3.1–3.8(10H, m), 3.47(3H, s), 7.18(1H, d, J=8 Hz), 7.26(1H, d, J=5 Hz), 7.42(1H, d, J=5 Hz), 7.63(1H, s), 7.78(1H, d, J=8 Hz), 7.99(1/2H, s), 8.07(1/2H, s).

(2) In 4.3 mL of tetrahydrofuran is dissolved 0.43 g of N-[2-(2-benzo[b]thiophen-5-yletoxy)ethyl]-N-(2-hydroxy-1-methylethyl)-formamide. To the solution thus obtained is dropwise added at an ice-cooled temperature 5.60 mL of 1 mol/L solution of borane-tetrahydrofuran complex in tetrahydrofuran. The resulting mixture is stirred at ambient temperature for 1.5 hours. The reaction mixture is acidified with 1.9 mL of 6 mol/L hydrochloric acid and heated under reflux for one hour. After cooling the reaction mixture to ambient temperature, water and ethyl acetate are added, pH is adjusted to 9.5 with 2 mol/L aqueous solution of sodium hydroxide, and the organic layer is separated. The organic layer is washed with saturated aqueous solution of sodium chloride and dried over anhydrous magnesium sulfate, the solvent is distilled off under reduced pressure, and the oily product thus obtained is purified by column chromatography (eluent: chloroform:methanol=30:1) to obtain 0.20 g of 2-[[2-(2-benzo[b]thiophen-5-yletoxy)ethyl](methyl) amino]-1-propanol as a light yellow-colored oily product.

IR(neat)cm$^{-1}$: 3422, 2937, 2862, 1113, 703.

NMR(CDCl$_3$)δ: 0.83(3H, d, J=7 Hz), 2.26(3H, s), 2.3–3.2 (5H, m), 3.2–3.8(6H, m), 7.21(1H, d, J=8 Hz), 7.27(1H, d, J=5 Hz), 7.41(1H, d, J=5 Hz), 7.67(1H, s), 7.79(1H, d, J=8 Hz).

EXAMPLES 140–142

Example 139(2) is repeated to obtain the following compounds.

No.140: 1-[[2-(2-Benzo[b]thiophen-5-ylethoxy)ethyl]-(methyl)amino]-2-propanol

IR(neat)cm$^{-1}$: 3448, 2864, 1114, 1051.

NMR(CDCl$_3$)δ: 1.10(3H, d, J=6 Hz), 2.31(3H, s), 2.60 (2H, t, J=5 Hz), 2.71(2H, d, J=7 Hz), 3.00(2H, t, J=7 Hz), 3.5–3.8(1H, m), 3.53(2H, t, J=5 Hz), 3.70(2H, t, J=7 Hz), .7.21(1H, d, J=8 Hz), 7.28(1H, d, J=5 Hz), 7.42(1H, d, J=5 Hz), 7.67(1H, s), 7.79(1H, d, J=8 Hz).

No.141: 3-[[2-(2-Benzo[b]thiophen-5-ylethoxy)ethyl]-(methyl)amino]-1-propanol

IR(neat)cm$^{-1}$: 3397, 2922, 1115, 1049, 755.

NMR(CDCl$_3$)δ: 1.62(2H, qn, J=6 Hz), 2.25(3H, s), 2.56 (4H, t, J=6 Hz), 2.98(2H, t, J=6 Hz), 3.53(2H, t, J=6 Hz), 3.67(2H, t, J=6 Hz), 3.74(2H, t, J=6 Hz), 4.5(1H, brs), 7.20(1H, d, J=8 Hz), 7.25(1H, d, J=5 Hz), 7.38(1H, d, J=5 Hz), 7.65(1H, s), 7.76(1H, d, J=8 Hz).

No.142: N-[2-(2-Benzo[b]thiophen-5-ylethoxy)ethyl]-N-(2-methoxyethyl)-N-methylamine IR(neat)cm$^{-1}$: 2937, 2868, 1117, 1052, 702.

NMR(CDCl$_3$)δ: 2.31(3H, s), 2.5–2.8(4H, m), 3.00(2H, t, J=7 Hz), 3.32(3H, s), 3.45(2H, t, J=5 Hz), 3.57(2H, t, J=5 Hz), 3.69(2H, t, J=7 Hz), 7.20(1H, dd, J=2, 8 Hz), 7.27(1H, d, J=5 Hz), 7.41(1H, d, J=5 Hz), 7.66(1H, s), 7.78(1H, d, J=8 Hz).

EXAMPLE 143

In 0.9 mL of ethyl acetate is dissolved 0.18 g of 2-{[2-(2-benzo[b]thiophen-5-ylethoxy)ethyl]-(methyl)amino}-1-propanol, to which is added 2 mL of a solution of 0.055 g of oxalic acid in ethyl acetate. Then, 1 ml of acetone is added, and the resulting mixture is stirred at ambient temperature for 3.5 hours. The deposited crystal is collected by filtration, washed with ethyl acetate and dried to obtain 0.23 g of 2-[[2-(2-benzo[b]thiophen-5-ylethoxy)ethyl](methyl)amino]-1-propanol oxalate.

mp: 97–99° C.

IR(KBr)cm$^{-1}$: 3354, 1114, 720.

NMR(DMSO-d$_6$)δ: 1.08(3H, d, J=6 Hz), 2.64(3H, s), 2.95(2H, t, J=7 Hz), 3.1–3.9(9H, m), 7.26(1H, dd, J=1, 8 Hz), 7.39(1H, d, J=5 Hz), 7.72(1H, d, J=5 Hz), 7.76(1H, s), 7.91(1H, d, J=8 Hz).

EXAMPLES 144–145

Example 143 is repeated to obtain the following compounds.

No.144: 1-{[2-(2-Benzo[b]thiophen-5-ylethoxy)ethyl]-(methyl)amino}-2-propanol oxalate mp: 64.5–66° C.

IR(KBr)cm$^{-1}$: 3396, 1112, 720.

NMR(DMSO-d$_6$)δ: 1.01(3H, d, J=6 Hz), 2.69(3H, s), 2.91(2H, d, J=6 Hz), 2.92(2H, t, J=7 Hz), 3.21(2H, t, J=7 Hz), 3.71(4H, t, J=7 Hz), 3.8–4.0(1H, m), 6.8(2H, brs), 7.27(1H, d, J=8 Hz), 7.39(1H, d, J=5 Hz), 7.73(1H, d, J=5 Hz), 7.76(1H, s), 7.91(1H, d, J=8 Hz).

No.145: 3-{[2-(2-Benzo[b]thiophen-5-ylethoxy)ethyl]-(methyl)amino}-1-propanol oxalate mp: 93–95° C.

IR(KBr)cm$^{-1}$: 3410, 2952, 1112, 720.

NMR(DMSO-d$_6$)δ: 1.5–2.0(2H, m), 2.67(3H, s), 2.95 (4H, t, J=7 Hz), 3.19(2H, t, J=5 Hz), 3.43(2H, t, J=6 Hz), 3.6–4.0(4H, m), 7.27(1H, d, J=8 Hz), 7.39(1H, d, J=5 Hz), 7.72(1H, d, J=5 Hz), 7.75(1H, s), 7.90(1H, d, J=8 Hz).

EXAMPLE 146

In 3 ml of N,N-dimethylformamide is dissolved 0.60 g of N-[2-(2-benzo[b]thiophen-5-ylethoxy)ethyl]-N-(2-propynyl)amine, to which are added 0.40 g of benzyl bromide and 0.35 g of potassium carbonate. The mixture is stirred at ambient temperature for one hour. Water and ethyl acetate are added to the reaction mixture, and the organic layer is separated. The organic layer is washed with water and saturated aqueous solution of sodium chloride successively and dried over anhydrous magnesium sulfate, and the solvent is distilled off under reduced pressure. The residue is purified by column chromatography (eluent: chloroform:methanol=10:1 to 7:1) to obtain 0.67 g of N-[2-(2-benzo[b]thiophen-5-ylethoxy)ethyl]-N-benzyl-N-(2-propynyl)amine as an oily product.

IR(neat)cm$^{-1}$: 3292, 2863, 1112, 700.

NMR(CDCl$_3$)δ: 2.22(1H, t, J=2 Hz), 2.77(2H, t, J=6 Hz), 2.99(2H, t, J=7 Hz), 3.36(2H, d, J=2 Hz), 3.59(2H, t, J=6 Hz), 3.67(2H, s), 3.67(2H, t, J=7 Hz), 7.0–7.6(3H, m), 7.29(5H, s), 7.66(1H, s), 7.77(1H, d, J=8 Hz).

EXAMPLES 147–153

Example 146 is repeated to obtain the following compounds.

No.147: N-[2-(2-Benzo[b]thiophen-5-ylethoxy)ethyl]-N-(4-methoxybenzyl)-N-methylamine IR(neat)cm$^{-1}$: 3422, 2938, 2863, 1511, 1246, 1112, 1036, 704.

NMR(CDCl$_3$)δ: 2.23(3H, s), 2.65(2H, t, J=6 Hz), 3.00 (2H, t, J=7 Hz), 3.47(2H, s), 3.58(2H, t, J=6 Hz), 3.69(2H, t, J=7 Hz), 3.79(3H, s), 6.82(2H, d, J=9 Hz), 7.1–7.3(1H, m), 7.20(2H, d, J=9 Hz), 7.25(1H, d, J=5 Hz), 7.41(1H, d, J=5 Hz), 7.65(1H, s), 7.78(1H, d, J=8 Hz).

No.148: N-[2-(2-Benzo[b]thiophen-5-ylethoxy)ethyl]-N-(4-fluorobenzyl)-N-methylamine IR(neat)cm$^{-1}$: 3398, 2940, 2864, 1508, 1221, 1113, 703.

NMR(CDCl$_3$)δ: 2.22(3H, s), 2.59(2H, t, J=6 Hz), 3.00 (2H, t, J=7 Hz), 3.48(2H, s), 3.58(2H, t, J=6 Hz), 3.68(2H, t, J=7 Hz), 6.8–7.3(5H, m), 7.19(1H, d, J=5 Hz), , 7.41(1H, d, J=5 Hz), 7.65(1H, s), 7.77(1H, d, J=8 Hz).

No.149: N-[2-(2-Benzo[b]thiophen-5-ylethoxy)ethyl]-N-methyl-N-(4-nitrobenzyl)amine IR(neat)cm$^{-1}$: 3422, 2942, 2864, 1519, 1345, 1111, 703.

NMR(CDCl$_3$)δ: 2.23(3H, s), 2.63(2H, t, J=6 Hz), 3.00 (2H, t, J=7 Hz), 3.5–3.7(2H, m), 3.58(2H, s), 3.70(2H, t, J=7 Hz), 7.2–7.3(1H, m), 7.20(1H, d, J=8 Hz), 7.40(2H, d, J=9 Hz), 7.41(1H, d, J=6 Hz), 7.65(1H, s), 7.76(1H, d, J=8 Hz), 8.11(2H, d, J=9 Hz).

No.150: N-[2-(2-Benzo[b]thiophen-5-ylethoxy)ethyl]-N-cyclopropyl-N-methylamine

IR(neat)cm$^{-1}$: 2861, 1116, 700.

NMR(CDCl$_3$)δ: 0.3–0.6(4H, m), 1.5–1.9(1H, m), 2.36 (3H, s), 2.75(2H, t, J=6 Hz), 3.00(2H, t, J=7 Hz), 3.60(2H, t, J=6 Hz), 3.70(2H, t, J=7 Hz), 7.21(1H, d, J=8 Hz), 7.28(1H, d, J=5 Hz), 7.42(1H, d, J=5 Hz), 7.67(1H, s), 7.79(2H, d, J=8 Hz).

No.151: N-[2-(2-Benzo[b]thiophen-5-ylethoxy)ethyl]-N-ethyl-N-(2-propynyl)amine

IR(neat)cm$^{-1}$: 3293, 2862, 1112, 701.

NMR(CDCl$_3$)δ: 1.05(3H, t, J=7 Hz), 2.16(1H, t, J=2 Hz), 2.58(2H, q, J=7 Hz), 2.71(2H, t, J=7 Hz), 3.01(2H, t, J=7 Hz), 3.44(2H, d, J=2 Hz), 3.57(2H, t, J=7 Hz), 3.71(2H, t, J=7 Hz), 7.21(1H, d, J=8 Hz), 7.25(1H, d, J=5 Hz), 7.38(1H, d, J=5 Hz), 7.67(1H, s), 7.78(1H, d, J=8 Hz).

No.152: N-[2-(2-Benzo[b]thiophen-5-ylethoxy)ethyl]-N-cyclopropyl-N-ethylamine

IR(neat)cm$^{-1}$: 2861, 1114, 700.

NMR(CDCl$_3$)δ: 0.4–0.5(4H, m), 1.05(3H, t, J=7 Hz), 1.6–1.9(1H, m), 2.70(3H, q, J=7 Hz), 2.81(2H, t, J=6 Hz), 3.00(2H, t, J=7 Hz), 3.61(2H, t, J=6 Hz), 3.70(2H, t, J=7 Hz), 7.21(1H, d, J=8 Hz), 7.28(1H, d, J=5 Hz), 7.42(1H, d, J=5 Hz), 7.67(1H, s), 7.79(2H, d, J=8 Hz).

No.153: N-[2-(2-Benzo[b]thiophen-5-ylethoxy)ethyl]-N-benzyl-N-cyclopropylamine

IR(neat)cm$^{-1}$: 2922, 2861, 1458, 1114, 755, 699.

NMR(CDCl$_3$)δ: 0.4–0.5(4H, m), 1.7–1.9(1H, m), 2.75 (2H, t, J=6 Hz), 2.97(2H, t, J=7 Hz), 3.57(2H, t, J=6 Hz), 3.65(2H, t, J=7 Hz), 3.79(2H, s), 7.1–7.3(7H, m), 7.41(1H, d, J=5 Hz), 7.65(1H, s), 7.77(2H, d, J=8 Hz).

EXAMPLE 154

In 1 mL of ethyl acetate is dissolved 0.67 g of N-[2-(2-benzo[b]thiophen-5-ylethoxy)ethyl]-N-benzyl-N-(2-propynyl)amine, to which is added 2.3 mL of a solution of 0.26 g of oxalic acid in ethyl acetate. The resulting mixture is stirred at ambient temperature for 2 hours. The deposited crystal is collected by filtration, washed with ethyl acetate and dried to obtain 0.63 g of N-[2-(2-benzo[b]thiophen-5-ylethoxy)ethyl]-N-benzyl-N-(2-propynyl)amine oxalate.

mp: 107–108° C.

IR(KBr)cm$^{-1}$: 3134, 1717, 1645, 700.

NMR(DMSO-d$_6$)δ: 2.71(2H, t, J=6 Hz), 2.91(2H, t, J=6 Hz), 3.22(1H, s}, 3.35(2H, s), 3.56(2H, t, J=6 Hz), 3.64(2H, t, J=6 Hz), 3.67(2H, s), 7.0–7.5(2H, m), 7.29(5H, s), 7.70 (1H, d, J=5 Hz), 7.74(1H, s), 7.88(1H, d, J=8 Hz), 9.2(2H, brs).

EXAMPLES 155–157

Example 154 is repeated to obtain the following compounds.

No.155: N-[2-(2-Benzo[b]thiophen-5-ylethoxy)ethyl]-N-(4-methoxybenzyl)-N-methylamine oxalate mp: 78.5–81° C.

IR(KBr)cm$^{-1}$: 3424, 2935, 1114, 720.

NMR(DMSO-d$_6$)δ: 2.51(3H, s), 2.8–3.2(4H, m), 3.6–3.9 (4H, m), 3.75(3H, s), 4.04(2H, s), 6.91(2H, d, J=9 Hz), 7.1–7.5(2H, m), 7.30(1H, d, J=8 Hz), 7.36(1H, d, J=6 Hz), 7.71(1H, d, J=6 Hz), 7.74(1H, s), 7.88(1H, d, J=8 Hz).

No.156: N-[2-(2-Benzo[b]thiophen-5-ylethoxy)ethyl]-N-(4-fluorobenzyl)-N-methylamine oxalate mp: 149–150.5° C.

IR(KBr)cm$^{-1}$: 3427, 2939, 1226, 1118, 720.

NMR(DMSO-d$_6$)δ: 2.49(3H, s), 2.8–3.2(4H, m), 3.6–3.9 (4H, m), 4.02(2H, s), 7.1–7.5(5H, m), 7.31(1H, d, J=6 Hz), 7.71(1H, d, J=6 Hz), 7.75(1H, s), 7.89(1H, d, J=8 Hz).

No.157: N-[2-(2-Benzo[b]thiophen-5-ylethoxy)ethyl]-N-methyl-N-(4-nitrobenzyl)amine oxalate mp: 112–114° C.

IR(KBr)cm$^{-1}$: 3426, 2863, 1522, 1349, 1120, 707.

NMR(DMSO-d$_6$)δ: 2.39(3H, s), 2.9–3.0(4H, m), 3.5–3.8 (4H, m), 3.96(2H, s), 7.27(1H, d, J=8 Hz), 7.35(1H, d, J=6 Hz), 7.59(2H, d, J=9 Hz), 7.70(1H, d, J=6 Hz), 7.74(1H, s), 7.88(1H, d, J=8 Hz), 8.19(2H, d, J=9 Hz).

EXAMPLE 158

In 2.2 mL of ethyl acetate is dissolved 0.44 g of N-[2-(2-benzo[b]thiophen-5-ylethoxy)ethyl]-N-cyclopropyl-N-methylamine, to which is added 0.60 mL of 3.5 mol/L solution of dry hydrogen chloride in ethyl acetate. The resulting mixture is stirred at ambient temperature for one hour. The reaction mixture is diluted with 5 mL of diisopropyl ether and stirred at ambient temperature for one hour. The deposited crystal is collected by filtration, washed with ethyl acetate and dried to obtain 0.31 g of N-[2-(2-benzo[b]thiophen-5-ylethoxy)ethyl]-N-cyclopropyl-N-methylamine hydrochloride.

mp: 67–70° C.

IR(KBr)cm$^{-1}$: 3418, 2628, 1111, 706.

NMR(CDCl$_3$)δ: 0.5–0.9(2H, m), 1.3–1.6(2H, m), 2.0–2.6 (1H, m), 2.70(3H, s), 3.00(2H, t, J=7 Hz), 3.27(2H, brs), 3.6–4.2(2H, m), 3.78(2H, t, J=7 Hz), 7.19(1H, d, J=8 Hz), 7.27(1H, d, J=5 Hz), 7.44(1H, d, J=5 Hz), 7.65(1H, s), 7.80(1H, d, J=8 Hz), 12.0(1H, brs).

EXAMPLE 159

Example 158 is repeated to obtain the following compound.

No.159: N-[2-(2-Benzo[b]thiophen-5-ylethoxy)ethyl]-N-ethyl-N-(2-propynyl)amine hydrochloride mp: 115–123° C.

IR(KBr)cm$^{-1}$: 3174, 2420, 1465, 1118, 709.

NMR(CDCl$_3$)δ: 1.33(3H, t, J=7 Hz), 2.55(1H, t, J=3 Hz), 3.01(2H, t, J=7 Hz), 2.8–3.4(4H, m), 3.78(2H, t, J=7 Hz), 3.7–4.4(4H, m), 7.22(1H, d, J=8 Hz), 7.29(1H, d, J=5 Hz), 7.43(1H, d, J=5 Hz), 7.69(1H, s), 7.80(1H, d, J=8 Hz), 12.8(1H, brs).

EXAMPLE 160

In 3.0 mL of toluene is suspended 0.44 g of sodium hydride (60% mineral oil suspension), to which is dropwise added, at an ice-cooled temperature, a mixture of 0.93 g of 1-(5-{2-[2-(dimethylamino)ethoxy]-ethyl}-2-hydroxyphenyl)-1-ethanone, 6.0 mL of toluene and 9.0 mL of ethyl formate. The resulting mixture is stirred at ambient temperature for one hour. Ice water and ethyl acetate are added to the reaction mixture, pH is adjusted to 11 with anhydrous potassium carbonate, and the organic layer is separated. The aqueous layer is twice extracted with ethyl acetate, and then the aqueous layer is salted out and further extracted once with ethyl acetate and four times with chloroform. The organic layers are collected and dried over anhydrous magnesium sulfate, and the solvent is distilled off under reduced pressure. The residue is dissolved in 13 mL of acetic acid, 6.5 mL of 12 mol/L aqueous hydrochloric acid is added, and the resulting mixture is stirred at 60° C. for 15 minutes. After cooling, chloroform and water are added, pH is adjusted to 7.0 with anhydrous potassium carbonate, and the organic layer is separated. The organic layer is dried over anhydrous magnesium sulfate, the solvent is distilled off under reduced pressure, and the residue is purified by column chromatography (eluent: chloroform:methanol= 50:1 to 5:1) to obtain 6-{2-[2-(dimethylamino)ethoxy]-ethyl}-4H-chromen-4-one as an oily product.

IR(neat)cm$^{-1}$: 1694, 1619, 1483, 1116.

NMR(CDCl$_3$)δ: 2.24(6H, s), 2.48(2H, t, J=6 Hz), 2.99 (2H, t, J=7 Hz), 3.54(2H, t, J=6 Hz), 3.70(2H, t, J=7 Hz), 6.32(1H, d, J=6 Hz), 7.37(1H, d, J=8 Hz), 7.57(1H, dd, J=2, 8 Hz), 7.83(1H, d, J=6 Hz), 8.03(1H, d, J=2 Hz).

EXAMPLE 161

Example 160 is repeated to obtain the following compound.

No.161: 6-{2-[2-(Diethylamino)ethoxy]ethyl}-4H-chromen-4-one

IR(neat)cm$^{-1}$: 3422, 2972, 1655, 1619.

NMR(CDCl$_3$)δ: 1.08(6H, t, J=7 Hz), 2.6–3.1(8H, m), 3.5–4.0(4H, m), 6.33(1H, d, J=6 Hz), 7.31(1H, d, J=7 Hz), 7.58(1H, dd, J=2, 7 Hz), 7.84(1H, d, J=7 Hz), 8.04(1H, d, J=2 Hz).

EXAMPLE 162

In 5 mL of ethyl acetate is dissolved 0.46 g of 6-{2-[2-(dimethylamino)ethoxy]ethyl}-4H-chromen-4-one, to which is added 0.8 mL of 3.6 mol/L solution of dry hydrogen chloride in ethyl acetate. The resulting mixture is stirred at ambient temperature for 12 hours. The deposited crystal is collected by filtration, washed with ethyl acetate, and dried to obtain 0.45 g of 6-{2-[2-(dimethylamino)ethoxy]ethyl}-4H-chromenon-4-one hydrochloride.

mp: 154–156° C.

IR(KBr)cm$^{-1}$: 1653, 1619, 1483, 1324.

NMR(CDCl$_3$)δ: 2.73(3H, s), 2.78(3H, s), 2.99(2H, t, J=6 Hz), 3.1–3.3(2H, m), 3.75(2H, t, J=6 Hz), 3.9–4.1(2H, m), 6.33(1H, d, J=6 Hz), 7.41(1H, d, J=9 Hz), 7.57(1H, dd, J=2, 9 Hz), 7.86(1H, d, J=6 Hz), 8.03(1H, d, J=2 Hz), 12.0(1H, brs).

EXAMPLE 163

Example 162 is repeated to obtain the following compound.

No.163: 6-{2-[2-(Diethylamino)ethoxy]ethyl}-4H-chromen-4-one hydrochloride mp: 173–176° C.

IR(KBr)cm$^{-1}$: 1660, 1619, 1481, 1113.

NMR(CDCl$_3$)δ: 1.32(6H, t, J=7 Hz), 2.8–3.4(8H, m), 3.75(2H, t, J=6 Hz), 3.8–4.1(2H, m), 6.33(1H, d, J=6 Hz), 7.42(1H, d, J=8 Hz), 7.56(1H, dd, J=2, 8 Hz), 7.86(1H, d, J=6 Hz), 8.01(1H, d, J=2 Hz).

EXAMPLE 164

In 10 mL of methylene chloride is dissolved 1.00 g of 2-{[2-(2-benzo[b]thiophen-5-ylethoxy)ethyl]-(methyl)amino}-1-ethanol. The solution thus obtained is cooled to 5° C., to which are added 0.32 mL of pyridine, 0.37 mL of acetic anhydride and 0.04 g of N,N-dimethylaminopyridine. The mixture is stirred at ambient temperature for 30 minutes. Water is added to the mixture, pH is adjusted to 7.5 with saturated aqueous solution of sodium hydrogen carbonate, and the organic layer is separated. The organic layer is washed with saturated aqueous solution of sodium chloride and dried over anhydrous magnesium sulfate, the solvent is distilled off under reduced pressure, and the residue is purified by column chromatography (eluent: chloroform:methanol=100:1 to 50:1) to obtain 1.14 g of 2-{[2-(2-benzo[b]-thiophen-5-ylethoxy)-ethyl](methyl)amino}ethyl acetate as an oily product.

IR(neat)cm$^{-1}$: 2945, 2858, 1738, 1238, 1115.

NMR(CDCl$_3$)δ: 2.05(3H, s), 2.32(3H, s), 2.65(2H, t, J=6 Hz), 2.68(2H, t, J=6 Hz), 3.00(2H, t, J=7 Hz), 3.56(2H, t, J=6 Hz), 3.70(2H, t, J=7 Hz), 4.14(2H, t, J=6 Hz), 7.20(1H, d, J=8 Hz), 7.27(1H, d, J=5 Hz), 7.42(1H, d, J=5 Hz), 7.66(1H, s), 7.79(1H, d, J=8 Hz).

EXAMPLE 165

In 2 ml of ethyl acetate is dissolved 1.14 g of 2-{[2-(2-benzo[b]thiophen-5-ylethoxy)ethyl](methyl)-amino}ethyl acetate, to which is added 3 mL of a solution of 0.32 g of oxalic acid in ethyl acetate. The mixture is stirred at ambient temperature for 2 hours. The deposited crystal is collected by filtration, washed with ethyl acetate and dried to obtain 1.15 g of 2-{[2-(2-benzo[b]thiophenyl-5-ylethoxy)ethyl](methyl)amino}ethyl acetate oxalate.

mp: 98–100.5° C.

IR(KBr)cm$^{-1}$: 3446, 1743, 1229, 1114.

NMR(DMSO-d$_6$)δ: 2.01(3H, s), 2.61(3H, s), 2.95(2H, t, J=7 Hz), 3.0–3.2(4H, m), 3.70(4H, t, J=6 Hz), 4.20(2H, t, J=5 Hz), 6.25(2H, brs), 7.27(1H, d, J=8 Hz), 7.40(1H, d, J=5 Hz), 7.73(1H, d, J=5 Hz), 7.76(1H, s), 7.91(1H, d, J=8 Hz).

EXAMPLE 166

In 5 mL of methylene chloride is dissolved 0.50 g of 2-{[2-(2-benzo[b]thiophen-5-ylethoxy)ethyl]-(methyl)amino}-1-ethanol. The solution thus obtained is cooled to −60° C., to which are added 0.37 mL of triethylamine and 0.31 mL of pivaloyl chloride. The mixture is stirred at the same temperature as above for 30 minutes and then at ambient temperature for one hour. Water is added to the reaction mixture, pH is adjusted to 9.0 with 1 mol/L aqueous solution of sodium hydroxide, and the organic layer is separated. The organic layer is washed with saturated aqueous solution of sodium chloride and dried over anhydrous magnesium sulfate, the solvent is distilled off under reduced pressure, and the residue is purified by column chromatography (eluent: chloroform:methanol=100:1 to 50:1) to obtain 0.54 g of 2-{[2-(2-benzo[b]thiophen-5-ylethoxy)ethyl](methyl)amino}ethyl pivalate as an oily product.

IR(neat)cm$^{-1}$: 2958, 2868, 1726, 1156.

NMR(CDCl$_3$)δ: 1.19(9H, s), 2.33(3H, s), 2.65(2H, t, J=6 Hz), 2.69(2H, t, J=6 Hz), 3.00(2H, t, J=7 Hz), 3.55(2H, t, J=6 Hz), 3.70(2H, t, J=7 Hz), 4.15(2H, t, J=6 Hz), 7.20(1H, d, J=8 Hz), 7.27(1H, d, J=5 Hz), 7.42(1H, d, J=5 Hz), 7.66(1H, s), 7.79(1H, d, J=8 Hz).

EXAMPLES 167–168

Example 166 is repeated to obtain the following compounds.

No.167: 2-{[2-(2-Benzo[b]thiophen-5-ylethoxy)ethyl]-(methyl)amino}ethyl ethyl carbonate IR(neat)cm$^{-1}$: 2943, 2862, 1744, 1260, 1115, 1015, 702.

NMR(CDCl$_3$)δ: 1.29(3H, t, J=7 Hz), 2.33(3H, s), 2.65 (2H, t, J=6 Hz), 2.71(2H, t, J=6 Hz), 3.00(2H, t, J=7 Hz), 3.56(2H, t, J=6 Hz), 3.70(2H, t, J=7 Hz), 4.18(2H, q, J=7 Hz), 4.19(2H, t, J=6 Hz), 7.21(1H, d, J=8 Hz), 7.28(1H, d, J=5 Hz), 7.42(1H, d, J=5 Hz), 7.66(1H, s), 7.79(1H, d, J=8 Hz).

No.168: 2-{[2-(Benzo[b]thiophen-5-ylethoxy)ethyl]-(methyl)amino}ethyl benzoate

IR(neat)cm$^{-1}$: 1718, 1274, 1114, 711.

NMR(CDCl$_3$)δ: 2.39(3H, s), 2.71(2H, t, J=6 Hz), 2.84 (2H, t, J=6 Hz), 2.99(2H, t, J=7 Hz), 3.58(2H, t, J=6 Hz), 3.70(2H, t, J=7 Hz), 4.41(2H, t, J=6 Hz), 7.19(1H, d, J=8 Hz), 7.27(1H, d, J=3 Hz), 7.39(1H, d, J=3 Hz), 7.4–7.6(3H, m), 7.65(1H, s), 7.77(1H, d, J=8 Hz), 8.04(2H, dd, J=2, 8 Hz).

EXAMPLE 169

In 3.2 mL of ethyl acetate is dissolved 0.54 g of 2-{[2-(2-benzo[b]thiophen-5-ylethoxy)ethyl]-(methyl)amino}ethyl pivalate, to which is added 0.53 ml of 3.6 mol/L solution of dry hydrogen chloride in ethyl acetate. The mixture is stirred at ambient temperature for one hour. The reaction mixture is diluted with 5 mL of diisopropyl ether and stirred at ambient temperature for one hour. The deposited crystal is collected by filtration, washed with ethyl acetate and dried to obtain 0.46 g of 2-{[2-(2-benzo[b]thiophen-5-ylethoxy)ethyl](methyl)amino}ethyl pivalate hydrochloride.

mp: 118–119° C.

IR(KBr)cm$^{-1}$: 2970, 1722, 1154, 1108.

NMR(CDCl$_3$)δ: 1.19(9H, s), 2.67(3/2H, s), 2.73(3/2H, s), 2.99(2H, t, J=7 Hz), 3.06(2H, t, J=5 Hz), 3.24(2H, t, J=4 Hz), 3.77(2H, t, J=7 Hz), 3.95(2H, t, J=4 Hz), 4.39(2H, t, J=5 Hz), 7.18(1H, d, J=8 Hz), 7.29(1H, d, J=5 Hz), 7.44(1H, d, J=5 Hz), 7.65(1H, s), 7.80(1H, d, J=8 Hz), 12.9(1H, brs).

EXAMPLES 170–171

Example 169 is repeated to obtain the following compounds.

No.170: 2-{[2-(2-Benzo[b]thiophen-5-ylethoxy)ethyl]-(methyl)amino}ethyl ethyl carbonate hydrochloride mp: 73.5–76° C.

IR(KBr)cm$^{-1}$: 1747, 1253, 1114, 1011, 702.

NMR(CDCl$_3$)δ: 1.31(3H, t, J=7 Hz), 2.71(3/2H, s), 2.76(3/2H, s), 2.99(2H, t, J=6 Hz), 3.2–3.4(4H, m), 3.77(2H, t, J=6 Hz), 3.94(2H, t, J=5 Hz), 4.22(2H, q, J=7 Hz), 4.43(2H, t, J=5 Hz), 7.20(1H, d, J=8 Hz), 7.30(1H, d, J=5 Hz), 7.44(1H, d, J=5 Hz), 7.67(1H, s), 7.81(1H, d, J=8 Hz), 12.9(1H, brs).

No.171: 2-{[2-(2-Benzo[b]thiophen-5-ylethoxy)ethyl]-(methyl)amino}ethyl benzoate hydrochloride mp: 97–98° C.

IR(KBr)cm$^{-1}$: 1719, 1266, 1115, 719.

NMR(CDCl$_3$)δ: 2.75(3H, s), 2.98(2H, t, J=7 Hz), 3.2–3.4 (4H, m), 3.76(2H, t, J=7 Hz), 3.95(2H, t, J=4 Hz), 4.63(2H, t, J=5 Hz), 7.1–7.6(6H, m), 7.64(1H, s), 7.78(1H, d, J=8 Hz), 8.03(2H, d, J=8 Hz), 13.0(1H, brs).

EXAMPLE 172

(1) In 4.80 mL of N,N-dimethylformamide is dissolved 4.80 g of 2-{[2-(2-benzo[b]thiophen-5-ylethoxy)ethyl]-(methyl)amino}-1-ethanol. To the solution are successively added 1.40 g of imidazole and 3.10 g of t-butyldimethylchlorosilane, the mixture thus obtained is stirred at ambient temperature for one hour. Water and ethyl acetate are added to the reaction mixture, pH is adjusted to 10 with saturated aqueous solution of sodium hydrogen carbonate, and the organic layer is separated. The organic layer is washed with water and saturated aqueous solution of sodium chloride and dried over anhydrous magnesium sulfate, the solvent is distilled off under reduced pressure, and the residue is purified by column chromatography (eluent: chloroform:methanol=50:1 to 40:1) to obtain 6.21 g of N-[2-(2-benzo[b]thiophen-5-ylethoxy)ethyl]-N-({[1-(tert-butyl)1,1-dimethylsilyl]-oxy}ethyl)-N-methylamine as an oily product.

IR(neat)cm$^{-1}$: 2952, 2856, 1112, 835.

NMR(CDCl$_3$)δ: 0.05(6H, s), 0.89(9H, s), 2.32(3H, s), 2.58(2H, t, J=7 Hz), 2.65(2H, t, J=6 Hz), 3.01(2H, t, J=7 Hz), 3.56(2H, t, J=6 Hz), 3.71(4H, t, J=7 Hz), 7.21(1H, d, J=8 Hz), 7.28(1H, d, J=5 Hz), 7.42(1H, d, J=5 Hz), 7.66(1H, s), 7.79(1H, d, J=8 Hz).

(2) In 20 mL of tetrahydrofuran is dissolved 2.00 g of N-[2-(2-benzo[b]thiophen-5-ylethoxy)ethyl]-N-({[1-(tert-butyl)-1,1-dimethylsilyl]oxy-ethyl)-N-methylamine. The solution is cooled to −60° C., 4.8 mL of 1.6 mol/L solution of n-butyllithium in hexane is dropwise added thereto, and the resulting mixture is stirred at the same temperature as above for 30 minutes. Then, 7.5 mL of acetone is added, the temperature is elevated to ambient temperature, and the mixture is stirred for 1.5 hours. The reaction mixture is introduced into a mixture of water and ethyl acetate, and the organic layer is separated. The organic layer is washed with saturated aqueous solution of sodium chloride and dried over anhydrous magnesium sulfate, the solvent is distilled off under reduced pressure, and the residue is purified by column chromatography (eluent: chloroform:methanol=100:1 to 20:1) to obtain 1.38 g of 2-[5-(2-{2-[({[1-(tert-butyl)-1,1-dimethylsilyl]oxy}-ethyl)(methyl)amino]ethoxy}-ethyl)benzo[b]thiophen-2-yl]-2-propanol as an oily product.

IR(neat)cm$^{-1}$: 3397, 2929, 2857, 1109.

NMR(CDCl$_3$)δ: 0.05(6H, s), 0.89(9H, s), 1.72(6H, s), 2.32(3H, s), 2.57(2H, t, J=6 Hz), 2.64(2H, t, J=6 Hz), 2.97(2H, t, J=7 Hz), 3.55(2H, t, J=6 Hz), 3.67(2H, t, J=7 Hz), 3.71(2H, t, J=6 Hz), 7.10(1H, s), 7.22(1H, d, J=8 Hz), 7.53(1H, s), 7.70(1H, d, J=8 Hz).

(3) In 14 ml of 90% methanol is dissolved 1.38 g of 2-[5-(2-{2-[({[1-tert-butyl)1,1-dimethylsilyl]-oxy}ethyl (methyl)amino]ethoxy}ethyl)-benzo[b]thiophen-2-yl]-2-propanol, to which is added 0.39 g of potassium fluoride. The mixture is heated under reflux for 3 hours. Water and ethyl acetate is added to the reaction mixture, and the organic layer is separated. The organic layer is washed with saturated aqueous solution of sodium chloride and dried over anhydrous magnesium sulfate, the solvent is distilled off under reduced pressure, and the residue is purified by column chromatography (eluent: chloroform:methanol=50:1 to 10:1) to obtain 0.65 g of 2-[5-(2-{2-[(2-hydroxyethyl)-(methyl)amino]ethoxy}ethyl)benzo[b]thiophene]-2-propanol as an oily product.

IR(neat)cm$^{-1}$: 3386, 2932, 2867, 1112.

NMR(CDCl$_3$)δ: 1.71(6H, s), 2.30(3H, s), 2.55(2H, t, J=5 Hz), 2.63(2H, t, J=6 Hz), 2.97(2H, t, J=7 Hz), 3.53(2H, t, J=6 Hz), 3.55(2H, t, J=5 Hz), 3.68(2H, t, J=7 Hz), 7.12(1H, s), 7.23(1H, d, J=8 Hz), 7.54(1H, s), 7.70(1H, d, J=8 Hz).

EXAMPLE 173

In 1 mL of ethyl acetate is dissolved 0.50 g of 2-[5-(2-{2-[(2-hydroxyethyl)(methyl)amino]-ethoxy}ethyl)-benzo[b]thiophene]-2-propanol, to which is added 2 mL of a solution of 0.13 g of oxalic acid in ethyl acetate. The mixture is stirred at ambient temperature for 1 hour. After stirring the mixture for an additional 2 hours, the deposited crystal is collected by filtration, washed with ethyl acetate and dried to obtain 0.41 g of 2-[5-(2-{2-[(2-hydroxyethyl)-(methyl)amino]ethoxy}ethyl)-benzo[b]thiophene]-2-propanol oxalate.

mp: 62.5–65.5° C.

IR(KBr)cm$^{-1}$: 3374, 2973, 1111.

NMR(DMSO-d$_6$)δ: 1.56(6H, s), 2.70(3H, s), 2.92(2H, t, J=7 Hz), 3.06(2H, t, J=7 Hz), 3.22(2H, t, J=7 Hz), 3.68(6H, t, J=7 Hz), 4.6(2H, brs), 7.14(1H, s), 7.18(1H, d, J=8 Hz), 7.59(1H, s), 7.78(1H, d, J=8 Hz).

EXAMPLE 174

(1) In 30 mL of tetrahydrofuran is dissolved 4.75 g of N-[2-(2-benzo[b]thiophen-5-ylethoxy)ethyl]-N,N-diethylamine. The solution is cooled to −60° C., 16.4 mL of 1.57 mol/L solution of n-butyllithium in hexane is dropwise added thereto, and the resulting mixture is stirred at the same temperature as above for 30 minutes. Then, 4.3 mL of triisopropyl borate is added. The reaction mixture is mixed with water, adjusted to pH 6 with acetic acid, and stirred at ambient temperature. Diethyl ether and 1 mol/L aqueous solution of sodium hydroxide are added to the mixture, and the aqueous layer is separated. The aqueous layer is adjusted to pH 9 with concentrated hydrochloric acid and extracted with methylene chloride. The organic layer is washed with saturated aqueous solution of sodium chloride and dried over anhydrous sodium sulfate and the solvent is distilled off under reduced pressure. Thus, 2.13 g of 5-{2-[2-(diethylamino)-ethoxy]ethyl}benzo[b]thiophene-2-boric acid is obtained.

(2) In a mixture of 8 mL of dimethoxyethane and 8 mL of water is dissolved 1.63 g of 5-{2-[2-(diethylamino)-ethoxy]ethyl}benzo[b]thiophene-2-boric acid, to which are added 0.81 g of sodium carbonate, 9 mg of dichloro bis (triphenylphosphine)palladium(II) and 0.44 mL of 3-bromopyridine. The mixture thus obtained is heated under reflux for 2 hours in an atmosphere of nitrogen. Ethyl acetate and water added to the reaction mixture, and the organic layer is separated. The organic layer is washed with saturated aqueous solution of sodium chloride and dried over anhydrous magnesium sulfate, the solvent is distilled off under reduced pressure, and the residue is purified by column chromatography (eluent: chloroform:methanol=10:1) to obtain 0.41 g of N,N-diethyl-N-(2-{2-[2-(3-pyridyl)benzo[b]thiophen-5yl]ethoxy}ethyl)amine.

IR(neat)cm$^{-1}$: 2968, 2868, 1113, 803, 754.

NMR(CDCl$_3$)δ: 1.02(6H, t, J=7 Hz), 2.57(4H, q, J=7 Hz), 2.67(2H, t, J=6 Hz), 3.01(2H, t, J=7 Hz), 3.57(2H, t, J=6 Hz), 3.72(2H, t, J=7 Hz), 7.22(1H, d, J=8 Hz), 7.35(1H, dd, J=5, 8 Hz), 7.55(1H, s), 7.66(1H, s), 7.76(1H, d, J=8 Hz), 7.96(1H, d, J=8 Hz), 8.57(1H, dd, J=2, 5 Hz), 8.98(1H, d, J=2 Hz).

EXAMPLE 175

In 1 mL of ethyl acetate is dissolved 0.41 g of N,N-diethyl-N-(2-{2-[2-(3-pyridyl)benzo[b]thiophen-5-yl]-ethoxy}ethyl)amine, to which are added 2 mL of a solution of 0.10 g of oxalic acid in ethyl acetate and ethanol, and the mixture thus obtained is stirred at ambient temperature. The deposited crystal is collected by filtration, washed with ethanol and dried to obtain 0.32 g of N,N-diethyl-N-(2-{2-[2-(3-pyridyl)benzo[b]-thiophenyl-5-yl]ethoxy}ethyl)amine oxalate.

mp: 131–133° C.

IR(KBr)cm$^{-1}$: 2949, 1113, 804, 720, 702.

NMR(DMSO-d$_6$)δ: 1.10(6H, t, J=7 Hz), 2.8–3.3(8H, m), 3.6–3.9(4H, m), 5.0(2H, brs), 7.31(1H, d, J=8 Hz), 7.52(1H, dd, J=5, 8 Hz), 7.75(1H, s), 7.94(1H, d, J=8 Hz), 7.95(1H, s), 8.15(1H, d, J=8 Hz), 8.58(1H, dd, J=1, 5 Hz), 9.01(1H, d, J=1Hz).

EXAMPLE 176

In 20 mL of ethanol is dissolved 12.69 g of 2-{[2-(2-benzo[b]thiophen-5-ylethoxy)ethyl](methyl)-amino}-1-ethanol. Then, 5.01 g of fumaric acid is added to the solution and heated. The solvent is distilled off under reduced pressure, 100 mL of acetone and 100 mL of diethyl ether are added to the residue, and the mixture thus obtained is stirred at ambient temperature for 2 hours. After stirring the mixture at 5° C. for an additional one hour, the deposited crystal is collected by filtration, washed with 1:1 mixture of diethyl ether and acetone, and dried to obtain 15.03 g of 2-{[2-(2-benzo[b]thiophen-5-ylethoxy)ethyl](methyl)amino}-1-ethanol fumarate.

mp: 86–88° C.

IR(KBr)cm$^{-1}$: 3400, 1684, 984, 647.

NMR(DMSO-d$_6$)δ: 2.42(3H, s), 2.72(2H, t, J=6 Hz), 2.85(2H, t, J=6 Hz), 2.92(2H, t, J=6 Hz), 3.54(2H, t, J=6 Hz), 3.60(2H, t, J=6 Hz), 3.67(2H, t, J=6 Hz), 6.56(2H, s), 7.0(2H, brs), 7.25(1H, d, J=8 Hz), 7.39(1H, d, J=5 Hz), 7.72(1H, d, J=5 Hz), 7.75(1H, s), 7.89(1H, d, J=8 Hz).

REFERENTIAL EXAMPLE 1

(1) In 28 mL of N,N-dimethylformamide is dissolved 5.60 g of 2-benzo[b]thiophen-5-yl-1-ethanol, to which are added 4.23 g of potassium tert-butoxide and 6.09 g of 1-chloroacetylpiperidine at an ice-cooled temperature. The mixture thus formed is stirred at the same temperature as above for 30 minutes, and then at ambient temperature for 2 hours. The reaction mixture is introduced into a mixture of ethyl acetate and water and adjusted to pH 2.0 with 2 mol/L hydrochloric acid, and then the organic layer is separated. The organic layer is washed with water and saturated aqueous solution of sodium chloride successively and dried over anhydrous magnesium sulfate, the solvent is distilled off under reduced pressure, and the residue is purified by column chromatography (eluent: n-hexane:ethyl acetate=5:1 to 2:1) to obtain 8.50 g of 2-(2-benzo[b]thiophen-5-ylethoxy)-1-piperidino-1-ethanone as an oily product.

IR(KBr)cm$^{-1}$: 2935, 1652, 1444, 1255, 1118.

NMR(CDCl$_3$)δ: 1.2–1.8(6H, m), 3.05(2H, t, J=7 Hz), 3.1–3.8(4H, m), 3.81(2H, t, J=7 Hz), 4.15(2H, s), 7.1–7.6 (3H, m), 7.7–8.0(2H, m).

The following compounds are obtained in the same manner as above.

2-[2-(1,3-Benzodioxol-5-yl)ethoxy]-1-piperidino-1-ethanone

2-[2-(2-Phenylbenzo[b]thiophen-5-yl)ethoxy]-1-piperidino-1-ethanone

2-[2-(6-Fluorobenzo[b]thiophen-5-yl)ethoxy]-1-piperidino-1-ethanone 2-(2-Benzo[b]thiophen-7-ylethoxy)-1-piperidino-1-ethanone (2) In a mixture of 58 mL of ethanol and 6 mL of water is dissolved 6.40 g of 2-(2-benzo[b]thiophen-5-ylethoxy)-1-piperidino-1-ethanone, to which is added 1.27 g of sodium hydroxide. The mixture is heated under reflux for 4 hours. After cooling the mixture, the deposited matter is collected by filtration. The deposited matter is added to a mixture of ethyl acetate and water, pH is adjusted to 1.5 with 2 mol/L hydrochloric acid, and the organic layer is separated. The organic layer is washed with water and saturated aqueous solution of sodium chloride and dried over anhydrous magnesium sulfate, and the solvent is distilled off under reduced pressure to obtain 3.72 g of 2-(2-benzo[b]thiophen-5-ylethoxy)-acetic acid as a colorless crystalline product.

IR(KBr)cm$^{-1}$: 2955, 1763, 1221, 1128.

The following compounds are obtained in the same manner as above.

2-[2-(1,3-Benzodioxol-5-yl)ethoxy]-acetic acid

NMR(CDCl$_3$)δ: 2.86(2H, t, J=7 Hz), 3.74(2H, t, J=7 Hz), 4.12(2H, s), 5.92(2H, s), 6.6–6.8(3H, m).

2-[2-(2-Phenylbenzo[b]thiophen-5-yl)ethoxy]-acetic acid

2-[2-(6-Fluorobenzo[b]thiophen-5-yl)ethoxy]-acetic acid

NMR(CDCl$_3$)δ: 3.09(2H, t, J=7 Hz), 3.85(2H, t, J=7 Hz), 4.14(2H, s), 7.1–7.9(4H, m).

2-(2-Benzo[b]thiophen-7-ylethoxy)-acetic acid

NMR(CDCl$_3$)δ: 3.24(2H, t, J=7 Hz), 3.96(2H, t, J=7 Hz), 4.12(2H, s), 6.9–7.9(6H, m).

REFERENTIAL EXAMPLE 2

(1) In 27 mL of tetrahydrofuran is dissolved 2.70 g of 2-(2-benzo[b]thiophen-5-ylethoxy)-acetic acid. At an ice-cooled temperature, 0.65 g of sodium boron hydride is added to the solution, and stirred at the same temperature as above for 10 minutes. Then, at an ice-cooled temperature, 3.24 g of boron trifluoride diethyl ether complex is added to the reaction mixture over a period of 20 minutes, and the resulting mixture is stirred at the same temperature as above for 30 minutes and then at ambient temperature for 2 hours. The reaction mixture is introduced into a mixture of ethyl acetate and water, pH is adjusted to 1.0 with 2 mol/L hydrochloric acid, and the organic layer is separated. The organic layer is washed with water and saturated aqueous solution of sodium chloride successively and dried over anhydrous magnesium sulfate, the solvent is distilled off under reduced pressure, and the residue is purified by column chromatography (eluent: n-hexane:ethyl acetate=3:1 to 2:1) to obtain 2.34 g of 2-(2-benzo[b]thiophen-5-ylethoxy)-1-ethanol as an oily product.

IR(KBr)cm$^{-1}$: 3422, 2864, 1119, 1051.

NMR(CDCl$_3$)δ: 1.8–2.3(1H, m), 3.02(2H, t, J=7 Hz), 3.4–4.0(6H, m), 7.1–7.6(3H, m), 7.6–8.0(2H, m).

The following compounds are obtained in the same manner as above.

2-[2-(1,3-Benzodioxol-5-yl)ethoxy]-1-ethanol

NMR(CDCl$_3$)δ: 2.82(2H, t, J=7 Hz), 3.4–4.3(7H, m), 5.92(2H, s), 6.7–6.9(3H, m).

2-[2-(2-Phenylbenzo[b]thiophen-5-yl)ethoxy]-1-ethanol

NMR(CDCl$_3$)δ: 1.90(1H, s), 3.01(2H, t, J=7 Hz), 3.5–4.0 (6H, m), 7.1–7.9(9H, m).

(2) In 20 mL of methylene chloride is dissolved 2.10 g of 2-(2-benzo[b]thiophen-5-ylethoxy)-1-ethanol. At an ice-cooled temperature, 1.63 g of methanesulfonyl chloride and 1.47 g of pyridine are added to the solution obtained above, and the mixture thus formed is stirred at the same temperature as above for 30 minutes and then at ambient temperature for 12 hours. Then, methylene chloride and water are added to the reaction mixture, pH is adjusted to 2.0 with 2 mol/L hydrochloric acid, and the organic layer is separated. The organic layer is washed with water and saturated aqueous solution of sodium chloride successively and dried over anhydrous magnesium sulfate, the solvent is distilled off under reduced pressure, and the residue is purified by column chromatography (eluent: n-hexane:ethyl acetate=4:1 to 2:1) to obtain 2.50 g of 2-(2-benzo[b]thiophen-5-ylethoxy)-ethyl methanesulfonate.

IR(KBr)cm$^{-1}$: 1347, 1170, 1127.

NMR(CDCl$_3$)δ: 2.86(3H, s), 3.00(2H, t, J=7 Hz), 3.5–4.0 (4H, m), 4.2–4.5(2H, m), 7.2–7.6(3H, m), 7.6–8.0(2H, m).

The following compounds are obtained in the same manner as above.

2-[2-(1,3-Benzodioxol-5-yl)ethoxy]-ethyl methanesulfonate

NMR(CDCl$_3$)δ: 2.7–3.0(5H, m), 3.6–3.8(4H, m), 4.3–4.4 (2H, m), 5.92(2H, s), 6.6–6.8(3H, m).

2-[2-(2-Phenylbenzo[b]thiophen-5-yl)ethoxy]-ethyl methanesulfonate

REFERENTIAL EXAMPLE 3 (1)

The following compounds are obtained in the same manner as in Referential Example 1 (1).

2-[2-(2,3-Dihydro-1,4-benzodioxin-6-yl)ethoxy]-1-piperazino-1-ethanone

NMR(CDCl$_3$)δ: 1.2–1.9(6H, m), 2.81(2H, t, J=7 Hz), 3.1–3.7(4H, m), 3.68(2H, t, J=7 Hz), 6.6–7.0(3H, m).

2-(2-Benzo[b]thiophen-6-ylethoxy)-1-piperazino-1-ethanone

2-[2-(2,3-Dihydro-1H-5-indenyl)ethoxy]-1-piperazino-1-ethanone

2-[2-(6-Methoxybenzo[b]thiophen-5-yl)ethoxy]-1-piperizino-1-ethanone

2-[2-(2-Methylbenzo[b]thiophen-5-yl)ethoxy]-1-piperizino-1-ethanone 2-(3-Benzo[b]thiophen-5-ylpropoxy)-1-piperizino-1-ethanone 2-[2-(2-Methyl-1,3-benzothiazol-5-yl)ethoxy]-1-piperizino-1-ethanone

REFERENTIAL EXAMPLE 3 (2)

The following compounds are obtained in the same manner as in Referential Example 1 (2).

2-(2-(2,3-Dihydro-1,4-benzodioxin-6-yl)ethoxy)-acetic acid

NMR(CDCl$_3$)δ: 2.83(2H, t, J=7 Hz), 3.74(2H, t, J=7 Hz), 4.12(2H, s), 4.24(4H, s), 6.6–7.2(3H, m).

2-(2-Benzo[b]thiophen-6-ylethoxy)-acetic acid

NMR(CDCl$_3$)δ: 3.05(2H, t, J=7 Hz), 3.84(2H, t, J=7 Hz), 4.12(2H, s), 7.1–7.5(3H, m), 7.6–7.9(2H, m), 9.23(1H, s).

2-[2-(2,3-Dihydro-1H-5-indenyl)ethoxy]-acetic acid

NMR(CDCl$_3$)δ: 1.8–2.3(2H, m), 2.7–3.1(6H, m), 3.78 (2H, t, J=7 Hz), 4.12(2H, s), 6.8–7.8(4H, m).

2-[2-(6-Methoxybenzo[b]thiophen-5-yl)ethoxy]-acetic acid

IR(KBr)cm$^{-1}$: 1732, 1250, 1130, 1042, 752.

NMR(CDCl$_3$)δ: 3.06(2H, t, J=7 Hz), 3.83(2H, t, J=7 Hz), 3.89(3H, s), 4.11(2H, s), 7.19(1H, d, J=5 Hz), 7.26(1H, d, J=5 Hz), 7.32(1H, s), 7.59(1H, s).

2-[2-(2-Methylbenzo[b]thiophen-5-yl)ethoxy]-acetic acid 2-(3-Benzo[b]thiophen-5-ylpropoxy)-acetic acid NMR(CDCl$_3$)δ: 1.8–2.3(2H, m), 2.85(2H, t, J=7 Hz), 3.59(2H, t, J=7 Hz), 4.12(2H, s), 7.17(1H, d, J=8 Hz), 7.27(1H, d, J=5 Hz), 7.42(1H, d, J=5 Hz), 7.63(1H, s), 7.79(1H, d, J=8 Hz).

2-(2-Benzo[b]thiophen-4-ylethoxy)-acetic acid

NMR(CDCl$_3$)δ: 3.30(2H, t, J=7 Hz), 3.87(2H, t, J=7 Hz), 4.12(2H, s), 7.1–8.0(5H, m).

2-[2-(2-Methyl-1,3-benzothiazol-5-yl)ethoxy]-acetic acid

IR(KBr)cm$^{-1}$: 2916, 2867, 1716, 1428, 1220, 1136, 928.

NMR(DMSO-d$_6$)δ: 2.78(3H, s), 2.97(2H, t, J=7 Hz), 3.74(2H, t, J=7 Hz), 4.02(2H, s), 7.29(1H, dd, J=2, 8 Hz), 7.80(1H, d, J=2 Hz), 7.91(1H, d, J=8 Hz), 12.5(1H, brs).

REFERENTIAL EXAMPLE 4

In a mixture of 4 mL of toluene and 8 mL of 50% (W/V) aqueous solution of sodium hydroxide is suspended 2.0 g of 2-benzo[b]thiophen-5-yl-1-ethanol, to which are added 4.4 mL of 1-bromo-3-chloropropane and 0.11 g of tetra-n-butylammonium hydrogen sulfate. The mixture is heated under reflux for 2 hours. The reaction mixture is introduced into a mixture of water and toluene, and the organic layer is separated. The organic layer is washed with water and dried over anhydrous magnesium sulfate, the solvent is distilled off under reduced pressure, and the residue is purified by column chromatography (eluent: n-hexane:ethyl acetate= 10:1 to 5:1) to obtain 1.85 g of 5-[2-(3-chloropropyloxy) ethyl]benzo[b]thiophene as an oily product.

The following compounds are obtained in the same manner as above.

5-{2-[(5-Chloropentyl)oxy]ethyl}benzo[b]thiophene

NMR(CDCl$_3$)δ: 1.2–2.1(6H, m), 2.99(2H, t, J=7 Hz), 3.1–3.8(4H, m), 3.68(2H, t, J=7 Hz), 7.20(1H, d, J=8 Hz), 7.28(1H, d, J=5 Hz), 7.42(1H, d, J=5 Hz), 7.67(1H, s), 7.79(1H, d, J=8 Hz).

REFERENTIAL EXAMPLE 5

(1) In 20 mL of water is dissolved 1.50 g of 2-[(3,4-diaminophenethyl)oxy]-1-ethanol. After adjusting pH of the solution to 6.5 with sodium hydrogen carbonate, 2.22 g of sodium glyoxal bicarbonate is added at 60° C., and the mixture thus formed is stirred at the same temperature as above for 30 minutes. Ethyl acetate is added to the reaction mixture, pH is adjusted to 10 with 2 mol/L aqueous solution of sodium hydroxide, and the organic layer is separated. The organic layer is washed with saturated aqueous solution of sodium chloride and dried over anhydrous magnesium sulfate, and the solvent is distilled off under reduced pressure to obtain 0.73 g of 2-[2-(6-quinoxalinyl)-ethoxy]-1-ethanol as an oily product.

IR(neat)cm$^{-1}$: 3384, 2868, 1119, 1052.

NMR(CDCl$_3$)δ: 2.18(1H, brs), 3.15(2H, t, J=7 Hz), 3.4–4.1(4H, m), 3.85(2H, t, J=7 Hz), 7.68(1H, d, J=9 Hz), 7.94(1H, s), 8.05(1H, d, J=9 Hz), 8.80(2H, s).

(2) In 10 mL of benzene is dissolved 0.73 g of 2-[2-(6-quinoxalinyl)ethoxy]-1-ethanol, to which is added 0.32 mL of thionyl chloride. The mixture is heated under reflux for 30 minutes. The solvent is distilled off and the deposited crystal is collected by filtration to obtain 0.37 g of 6-[2-(2-chloroethoxy)-ethyl]-quinoxaline hydrochloride.

NMR(CDCl$_3$)δ: 3.25(2H, t, J=6 Hz), 3.61(2H, t, J=6 Hz), 3.74(2H, t, J=6 Hz), 3.90(2H, t, J=6 Hz), 8.05(1H, dd, J=2, 8 Hz), 8.45(1H, s), 8.47(1H, d, J=8 Hz), 9.15(2H, dd, J=2, 8 Hz), 11.2(1H, br s).

REFERENTIAL EXAMPLE 6

(1) In 10 mL of ethylene glycol monomethyl ether is dissolved 1.2 g of 2-[(3,4-diaminophenethyl)oxy]-1-ethanol dihydrochloride, to which is added 0.93 g of formamidine acetate. The mixture is heated under reflux for 30 minutes. Then, the solvent is distilled off under reduced pressure, water and methylene chloride are added to the residue, pH is adjusted to 9 with 2 mol/L aqueous solution of sodium hydroxide, and the organic layer is separated. The aqueous layer is salted out and extracted with methylene chloride. The organic layers are collected, washed with saturated aqueous solution of sodium chloride, and dried over anhydrous magnesium sulfate. The solvent is distilled off under reduced pressure, and the residue is purified by column chromatography (eluent: chloroform:methanol=10:1) to obtain 0.52 g of 2-[2-(1H-benzo[d]imidazol-5-yl)ethoxy]-1-ethanol as an oily product.

IR(neat)cm$^{-1}$: 3198, 2866, 1117, 1049.

NMR(CDCl$_3$)δ: 3.02(2H, t, J=7 Hz), 3.4–3.9(6H, m), 7.12(1H, d, J=9 Hz), 7.49(1H, s), 7.57(1H, d, J=9 Hz), 7.98(1H, s).

(2) In a mixture of 10 mL of benzene and 5 mL of chloroform is dissolved 0.52 g of 2-[2-(1H-benzo[b]-imidazol-5-yl)ethoxy]-1-ethanol, to which is added 0.22 ml of thionyl chloride. The mixture thus obtained is heated under reflux for 2 hours. The solvent is distilled off and the deposited crystal is collected by filtration to obtain 0.56 g of 5-[2-(2-chloroethoxy)-ethyl]-1H-benzo[d]imidazole hydrochloride.

IR(KBr)cm$^{-1}$: 3406, 2933, 1448, 1115.

NMR(DMSO-d$_6$)δ: 3.03(2H, t, J=6 Hz), 3.5–3.9(6H, m), 7.48(1H, d, J=8 Hz), 7.74(1H, s), 7.78(1H, d, J=8 Hz), 9.57(1H, s).

REFERENTIAL EXAMPLE 7

In 15 mL of N,N-dimethylformamide is dissolved 3.00 g of 2-(2-benzo[b]thiophen-5-ylethoxy)-ethyl methanesulfonate, to which are added 1.40 mL of propargylamine and 2.76 g of potassium carbonate. The mixture is heated at 80° C. for 3 hours. The reaction mixture is introduced into a mixture of water and ethyl acetate, and the organic layer is separated. The organic layer is washed with water and saturated aqueous solution of sodium chloride successively and dried over anhydrous magnesium sulfate, the solvent is distilled off under reduced pressure, and the residue is purified by column chromatography (eluent: chloroform:methanol=30:1 to 20:1) to obtain 1.63 g of N-[2-(2-benzo[b]thiophen-5-ylethoxy)ethyl]-N-(2-propynyl)amine as an oily product.

IR(neat)cm$^{-1}$: 3292, 2863, 1112, 756, 703.

NMR(CDCl$_3$)δ: 2.20(1H, t, J=2 Hz), 2.85(2H, t, J=5 Hz), 3.00(2H, t, J=7 Hz), 3.40(2H, d, J=2 Hz), 3.59(2H, t, J=5 Hz), 3.72(2H, t, J=7 Hz), 7.20(1H, d, J=9 Hz), 7.29(1H, d, J=5 Hz), 7.42(1H, d, J=5 Hz), 7.67(1H, s), 7.79(1H, d, J=9 Hz).

The following compounds are obtained in the same manner as above.

N-[2-(2-Benzo[b]thiophen-5-ylethoxy)ethyl]-N-cyclopropylamine

IR(neat)cm$^{-1}$: 2938, 2861, 1438, 1115, 755, 701.

NMR(CDCl$_3$)δ: 0.3–0.4(4H, m), 1.9–2.2(1H, m), 2.83 (2H, t, J=5 Hz), 3.00(2H, t, J=7 Hz), 3.56(2H, t, J=5 Hz), 3.71(2H, t, J=7 Hz), 7.21(1H, d, J=8 Hz), 7.28(1H, d, J=5 Hz), 7.42(1H, d, J=5 Hz), 7.67(1H, s), 7.79(1H, d, J=8 Hz).

1-{[2-(2-Benzo[b]thiophen-5-ylethoxy)ethyl]amino}-2-propanol

IR(neat)cm$^{-1}$: 3314, 2864, 1109, 755.

NMR(CDCl$_3$)δ: 1.10(3H, d, J=6 Hz), 2.28(1H, d, J=3 Hz), 2.32(1H, s), 2.43(1H, s), 2.57(1H, d, J=3 Hz), 2.74(2H, t, J=5 Hz), 3.00(2H, t, J=7 Hz), 3.5–3.8(1H, m), 3.55(2H, t, J=5 Hz), 3.72(2H, t, J=7 Hz), 7.21(1H, d, J=8 Hz), 7.28(1H, d, J=5 Hz), 7.42(1H, d, J=5 Hz), 7.66(1H, s), 7.80(1H, d, J=8 Hz).

3-{[2-(2-Benzo[b]thiophen-5-yolethoxy)ethyl]amino}-1-propanol

IR(neat)cm$^{-1}$: 3302, 2932, 2861, 1437, 1099, 703.

NMR(CDCl$_3$)δ: 1.60(2H, qn, J=5 Hz), 2.74(2H, t, J=5 Hz), 2.80(2H, t, J=5 Hz), 2.99(2H, t, J=5 Hz), 3.55(2H, t, J=5 Hz), 3.71(2H, t, J=5 Hz), 3.77(2H, t, J=5 Hz), 7.21(1H, d, J=8 Hz), 7.29(1H, d, J=5 Hz), 7.42(1H, d, J=5 Hz), 7.66(1H, s), 7.80(1H, d, J=8 Hz).

REFERENTIAL EXAMPLE 8

In 10 mL of methylene chloride is dissolved 1.0 g of 2-(2-benzo[b]thiophen-5-ylethoxy)-acetic acid. At an ice-cooled temperature, 0.41 mL of oxalyl chloride and 0.1 mL of N,N-dimethylformamide are added to the solution obtained above, and the mixture is stirred at ambient temperature for 1.5 hours. After cooling the mixture to −50° C., 0.41 mL of DL-alaninol and 1.77 mL of triethylamine are dropwise added, and the mixture thus formed is stirred at ambient temperature for 4 hours. Ice water is added to the reaction mixture, pH is adjusted to 1 with 6 mol/L hydrochloric acid, and the organic layer is separated. The organic layer is washed with saturated aqueous solution of sodium chloride and dried over anhydrous magnesium sulfate, and the solvent is distilled off under reduced pressure. The residue thus obtained is dissolved in 10 mL of tetrahydrofuran and cooled with ice, to which is dropwise added 16.9 mL of 1 mol/L solution of borane-tetrahydrofuran complex in tetrahydrofuran. The mixture thus obtained is stirred at ambient temperature for 13 hours. The reaction mixture is acidified with 5.6 mL of 6 mol/L hydrochloric acid and heated under reflux for one hour. After cooling the reaction mixture, the solvent is distilled off under reduced pressure, water and ethyl acetate are added to the residue, and the aqueous layer is separated. Ethyl acetate is added to the aqueous layer, pH is adjusted to 9.5 with 50% aqueous solution of sodium hydroxide, and the organic layer is separated. The organic layer thus obtained is washed with saturated aqueous solution of sodium chloride and dried over anhydrous magnesium sulfate, the solvent is distilled off under reduced pressure, and an oily residue thus obtained is purified by column chromatography (eluent: chloroform:methanol=40:1 to 30:1) to obtain 0.80 g of 2-{[2-(2-benzo[b]thiophen-5-ylethoxy)ethyl]amino}-1-propanol as a light yellow-colored oily product.

IR(neat)cm$^{-1}$: 3301, 2864, 1438, 1113, 702.

NMR(CDCl$_3$)δ: 0.98(3H, d, J=6 Hz), 2.2(2H, brs), 2.5–3.4(5H, m), 3.50(2H, t, J=5 Hz), 3.59(2H, d, J=5 Hz)3.71(2H, t, J=7 Hz), 7.20(1H, d, J=8 Hz), 7.27(1H, d, J=5 Hz), 7.42(1H, d, J=5 Hz), 7.66(1H, s), 7.79(1H, d, J=8 Hz).

The following compounds are obtained in the same manner as above.

N-[2-(2-Benzo[b]thiophen-5-ylethoxy)ethyl]-N-methylamine

IR(neat)cm$^{-1}$: 3328, 2864, 1438, 1099, 732.

NMR(CDCl$_3$)δ: 2.41(3H, s), 2.74(2H, t, J=5 Hz), 3.01 (2H, t, J=7 Hz), 3.59(2H, t, J=5 Hz), 3.72(2H, t, J=7 Hz), 7.21(1H, d, J=8 Hz), 7.28(1H, d, J=6 Hz), 7.42(1H, d, J=6 Hz), 7.66(1H, s), 7.79(1H, d, J=8 Hz).

N-[2-(2-Benzo[b]thiophen-5-ylethoxy)ethyl]-N-(2-methoxyethyl)amine

IR(neat)cm$^{-1}$: 2924, 2864, 1111, 704.

NMR(CDCl$_3$)δ: 1.9(1H, brs), 2.6–2.9(4H, m), 3.00(2H, t, J=7 Hz), 3.33(3H, s), 3.44(2H, t, J=5 Hz), 3.58(2H, t, J=5 Hz), 3.70(2H, t, J=7 Hz), 7.20(1H, d, J=8 Hz), 7.27(1H, d, J=5 Hz), 7.41(1H, d, J=5 Hz), 7.65(1H, s), 7.78(1H, d, J=8 Hz).

REFERENTIAL EXAMPLE 9

(1) In 50 mL of methylene chloride is dissolved 5.00 g of 2-(2-benzo[b]thiophen-5-ylethoxy)-acetic acid. At an ice-cooled temperature, 2.2 mL of oxalyl chloride and 0.1 mL of N,N-dimethylformamide are added to the solution obtained above, and the mixture thus formed is stirred at ambient temperature for 30 minutes. The solvent is distilled off under reduced pressure, the residue is dissolved in 5 mL of tetrahydrofuran, and the solution thus obtained is dropwise added to a tetrahydrofuran solution of sodium salt of di-tert-butyl malonate, prepared from 1.01 g of sodium hydride and 5.70 mL of di-tert-butyl malonate, at an ice-cooled temperature. The mixture thus obtained was stirred at the same temperature as above for 30 minutes. The reaction mixture is introduced into a mixture of ice water and ethyl acetate, pH is adjusted to 1.0 with 2 mol/L hydrochloric acid, and the organic layer is separated. The organic layer is washed with saturated aqueous solution of sodium chloride and dried over anhydrous magnesium sulfate, and the solvent is distilled off under reduced pressure. The residue is heated under reflux together with 20 mL of methylene chloride and 10 ml of trifluoroacetic acid, the solvent is distilled off under reduced pressure, and the residue is heated to make progress a de-carbonization reaction. Water and ethyl acetate are added to the reaction mixture, and the organic layer is separated. The organic layer is washed with saturated aqueous solution of sodium hydrogen carbonate and saturated aqueous solution of sodium chloride successively and dried over anhydrous magnesium sulfate, the solvent is distilled off under reduced pressure, and the residue is purified by column chromatography (eluent: n-hexane:ethyl acetate=7:1 to 5:1) to obtain 3.67 g of 1-(2-benzo[b]thiophen-5-ylethoxy)-acetone.

NMR(CDCl$_3$)δ: 2.11(3H, s), 3.06(2H, t, J=7 Hz), 3.76 (2H, t, J=7 Hz), 4.03(2H, s), 7.22(1H, d, J=8 Hz), 7.28(1H, d, J=5 Hz), 7.43(1H, d, J=5 Hz), 7.68(1H, s), 7.80(1H, d, J=8 Hz).

(2) In 13 mL of ethanol is dissolved 2.60 g of 1-(2-benzo [b]thiophen-5-ylethoxy)-acetone, to which is added 0.13 g of sodium boron hydride at an ice-cooled temperature. The mixture thus obtained is stirred at ambient temperature for one hour. Then, 1.7 mL of 2 mol/L hydrochloric acid is added at an ice-cooled temperature, the resulting mixture is stirred at ambient temperature for 20 minutes, and then water and ethyl acetate are added to the reaction mixture and the organic layer is separated. The organic layer is washed with saturated aqueous solution of sodium chloride and dried over anhydrous magnesium sulfate, the solvent is distilled off under reduced pressure, and the residue is dissolved in 26 mL of methylene chloride. At an ice-cooled temperature, 1.0 mL of methanesulfonyl chloride and 1.8 mL of triethylamine are added, and the mixture thus obtained is stirred at ambient temperature for 30 minutes. Water is added to the reaction mixture, and the organic layer is separated. The organic layer is washed with water and saturated aqueous solution of sodium chloride and dried over anhydrous magnesium sulfate, the solvent is distilled off under reduced pressure, and the residue is purified by column chromatography (eluent: n-hexane:ethyl acetate= 10:1 to 3:1) to obtain 2.75 g of 2-(2-benzo[b]thiophen-5-ylethoxy)-1-methylethyl methanesulfonate.

IR(KBr)cm$^{-1}$: 1332, 1175, 923, 904.

NMR(CDCl$_3$)δ: 1.36(3H, d, J=7 Hz), 2.80(3H, s), 3.00 (2H, t, J=7 Hz), 3.56(2H, d, J=2 Hz), 3.76(2H, t, J=7 Hz), 4.83(1H, dq, J=2, 7 Hz), 7.20(1H, d, J=8 Hz), 7.28(1H, d, J=5 Hz), 7.43(1H, d, J=5 Hz), 7.65(1H, s), 7.79(1H, d, J=8 Hz).

REFERENTIAL EXAMPLE 10

(1) In 30 mL of methylene chloride is dissolved 5.9 g of 2-(4-methoxyphenyl)-ethyl acetate. At an ice-cooled temperature, 3.8 mL of acetyl chloride and 7.2 g of aluminum chloride are added to the solution obtained above, and the resulting mixture is stirred at the same temperature as above for 3 hours. The reaction mixture is introduced into ice water, and the organic layer is separated. The organic layer is washed with saturated aqueous solution of sodium chloride and dried over anhydrous magnesium sulfate. By distilling off the solvent under reduced pressure, there is obtained 7.1 g of an oily crude product of 2-(3-acetyl-4-methoxyphenyl)-ethyl acetate.

NMR(CDCl$_3$)δ: 2.03(3H, s), 2.61(3H, s), 2.89(2H, t, J=7 Hz), 3.90(3H, s), 4.25(2H, t, J=7 Hz), 6.91(1H, d, J=9 Hz), 7.33(1H, dd, J=2, 9 Hz), 7.60(1H, d, J=2 Hz).

(2) In 2.0 mL of ethanol is dissolved 1.00 g of 2-(3-acetyl-4-methoxyphenyl)-ethyl acetate, to which are successively added 1.0 mL of water and 1.7 mL of 5.0 mol/L aqueous solution of sodium hydroxide. The mixture thus obtained is stirred at ambient temperature for 30 minutes. Water and ethyl acetate are added to the reaction mixture, and the organic layer is separated. The organic layer is washed with saturated aqueous solution of sodium chloride and dried over anhydrous magnesium sulfate, and the solvent is distilled off under reduced pressure. Thus, 0.80 g of 2-(3-acetyol-4-methoxyphenyl)-ethanol is obtained as an oily product.

IR(neat)cm$^{-1}$: 1668, 1496, 1253, 1024.

NMR(CDCl$_3$)δ: 1.5(1H, brs), 2.61(3H, s), 2.83(2H, t, J=7 Hz), 3.79(2H, t, J=7 Hz), 3.90(3H, s), 6.92(1H, d, J=8 Hz), 7.35(1H, dd, J=2, 8 Hz), 7.59(1H, d, J=2 Hz).

(3) In a mixture of 1.0 mL of toluene and 5.0 mL of 50% (w/v) aqueous solution of sodium hydroxide is dissolved 0.80 g of 2-(3-acetyl-4-methoxyphenyl)-ethanol, to which are successively added 0.28 g of tetra-n-butylammonium hydrogen sulfate and 0.90 g of 1-(2-chloroethyl)-diethylamine hydrochloride. The mixture thus obtained is heated under reflux for 20 minutes. The reaction mixture is introduced into a mixture of water and toluene, and the organic layer is separated. The organic layer is washed with saturated aqueous solution of sodium chloride and dried over anhydrous magnesium sulfate, the solvent is distilled off under reduced pressure, and the residue is purified by column chromatography (eluent: chloroform:methanol=50:1 to 10:1) to obtain 1.20 g of 1-[5-{2-(2-(diethylamino)ethoxy]ethyl}-2-methoxyphenyl]-1-ethanone as an oily product.

IR(neat)cm$^{-1}$: 2967, 1676, 1498, 1252, 1114.

NMR(CDCl$_3$)δ: 1.01(6H, t, J=7 Hz), 2.56(4H, q, J=7 Hz), 2.60(3H, s), 2.5–2.8(2H, m), 2.84(2H, t, J=7 Hz), 3.52(2H, t, J=7 Hz), 3.79(2H, t, J=8 Hz), 3.89(3H, s), 6.7–7.0(1H, m), 7.2–7.5(1H, m), 7.57(1H, d, J=2 Hz).

(4) In 5.0 mL of ethyl acetate is dissolved 1.20 g of 1-(5-{2-[2-(diethylamino)ethoxy]ethyl}-2-methoxyphenyl)-1-ethanone, to which is added 1.1 mL of 3.7 mol/L solution of dry hydrogen chloride in ethyl acetate. The solvent is distilled off under reduced pressure. The residue is dissolved in 6.0 mL of methylene chloride, to which are successively added at an ice-cooled temperature 1.60 g of aluminum chloride and 0.70 g of sodium iodide. The mixture thus obtained is stirred at ambient temperature for 2 hours. Ice water and chloroform are added to the reaction mixture, pH is adjusted to 8.0 with 1.0 mol/L aqueous solution of sodium hydroxide, and the organic layer is separated. The organic layer is dried over anhydrous magnesium sulfate and the solvent is distilled off under reduced pressure. Thus, 1.10 g of 1-(5-{2-[2-(diethylamino)ethoxy]ethyl}-2-hydroxyphenyl)-1-ethanone is obtained as an oily product.

NMR(CDCl$_3$)δ: 1.06(3H, t, J=7 Hz), 1.09(3H, t, J=8 Hz), 2.4–3.0(8H, m), 2.63(3H, s), 3.5–3.9(4H, m), 6.7–7.5(2H, m), 7.57(1H, s), 12.15(1H, s).

The following compound is obtained in the same manner as above.

1-(5-{2-[2-(Dimethylaminoethoxy]ethyl}-2-hydroxyphenyl)-1-ethanone

IR(neat)cm$^{-1}$: 1642, 1488, 1297, 1116.

NMR(CDCl$_3$)δ: 2.26(6H, s), 2.50(2H, t, J=6 Hz), 2.62 (3H, s), 2.85(2H, t, J=7 Hz), 3.55(2H, t, J=6 Hz), 3.63(2H, t, J=7 Hz), 6.90(1H, d, J=9 Hz), 7.35(1H, dd, J=2, 9 Hz), 7.59(1H, d, J=2 Hz), 12.11(1H, brs).

REFERENTIAL EXAMPLE 11

(1) In 59 mL of dimethyl sulfoxide is dissolved 11.8 g of methyl 2,4-difluoro-3-methoxybenzoate, to which are added 23.0 g of potassium carbonate and 9.33 g of sodium hydrogen sulfide n-hydrate (purity 70%). The mixture is stirred at 60° C. for 2 hours. Then, 25 mL of bromoacetaldehyde diethyl acetal is added at the same temperature as above, and stirred at that temperature for 3 hours. Water and ethyl acetate are added to the reaction mixture, and the organic layer is separated. The organic layer is washed with saturated aqueous solution of sodium chloride and dried over anhydrous magnesium sulfate, and the solvent is distilled off under reduced pressure. The residue is purified by column chromatography (eluent: hexane-ethyl acetate=5:1) to obtain 19.0 g of methyl 4-[(2,2-diethoxyethyl)sulfanyl]-2-fluoro-3-methoxybenzoate as an oily product.

IR(neat)cm$^{-1}$: 2977, 1729, 1599, 1421, 1303, 1124, 1059, 910.

NMR(CDCl$_3$)δ: 1.21(6H, t, J=7 Hz), 3.16(2H, d, J=6 Hz), 3.3–4.0(4H, m), 3.92(3H, s), 3.96 (3H, d, J=1 Hz), 4.71(1H, t, J=6 Hz), 7.05(1H, dd, J=1, 9 Hz), 7.60(1H, dd, J=7, 9 Hz).

The following compounds are obtained in the same manner as above.

Methyl 4-[(2,2-diethoxyethyl)sulfanyl]-2-fluoro-3-(methylsulfanyl)-benzoate

IR(neat)cm$^{-1}$: 2976, 1719, 1590, 1432, 1391, 1290, 1112, 1058, 905, 774.

NMR(CDCl$_3$)δ: 1.23(6H, t, J=7 Hz), 2.42(3H, s), 3.18 (2H, d, J=5 Hz), 3.4–4.0(4H, m), 3.92(3H, s), 4.74(1H, t, J=5 Hz), 7.07(1H, d, J=9 Hz), 7.82(1H, dd, J=7, 9 Hz).

Methyl 4-[(2,2-diethoxyethyl)sulfanyl]-2-fluoro-3-methylbenzoate

Methyl 2-chloro-4-[(2,2-dimethoxyethyl)sulfanyl)-benzoate

Methyl 4-[(2,2-diethoxyethyl)sulfanyl]-2-fluorobenzoate

Methyl 2-[(2,2-diethoxyethyl)sulfanyl]-4-fluorobenzoate

Methyl 2-[(2,2-diethoxyethyl)sulfanyl]-6-fluorobenzoate

IR(neat)cm$^{-1}$: 1736, 1278, 1108, 1058.

(2) In 190 mL of toluene is dissolved 19.0 g of methyl 4-[(2,2-doetjhoxyethyl)sulfanyl]-2-fluoro-3-methoxybenzoate, to which is added 19 mL of 85% phosphoric acid. The mixture is heated under reflux for 3 hours to achieve an azeotropic dehydration. Water and ethyl acetate are added to the reaction mixture, the insoluble matter is filtered off, and then the organic layer is separated. The organic layer is washed with saturated aqueous solution of sodium chloride and dried over anhydrous magnesium sulfate, the solvent is distilled off under reduced pressure, and the residue is purified by column chromatography (eluent: hexane:ethyl acetate=5:1) to obtain 5.95 g of methyl 6-fluoro-7-methoxybenzo[b]thiophene-5-carboxylate.

NMR(CDCl$_3$)δ: 3.97(3H, s), 4.15 (3H, d, J=2 Hz), 7.33 (1H, d, J=5 Hz), 7.45(1H, d, J=5 Hz), 8.09(1H, d, J=5 Hz).

The following compounds are obtained in the same manner as above.

Methyl 6-fluoro-7-(methylthio)benzo[b]thiophene-5-carboxylate

NMR(CDCl$_3$)δ: 2.56(3H, s), 3.97(3H, s), 7.38(1H, d, J=5 Hz), 7.50(1H, d, J=5 Hz), 8.34(1H, d, J=6 Hz).

Methyl 6-fluoro-7-methylbenzo[b]thiophene-5-carboxylate

Methyl 4-chlorobenzo[b]thiophene-5-carboxylat

Methyl 6-chlorobenzo[b]thiophene-5-carboxylate

Methyl 4-fluorobenzo[b]thiophene-5-carboxylate

IR(KBr)cm$^{-1}$: 1711, 1290, 1199, 1127, 740.

Methyl 6-fluorobenzo[b]thiophene-5-carboxylate

Methyl 4-fluorobenzo[b]thiophene-7-carboxylate

Methyl 6-fluorobenzo[b]thiophene-7-carboxylate

REFERENTIAL EXAMPLE 12

In 35 ml of N,N-dimethylformamide is dissolved 7.00 g of methyl 6-fluorobenzo[b]thiophene-5-carboxylate, to which is added 7.1 mL of a 28% methanol solution of sodium methoxide. The mixture is stirred at 80° C. for 4 hours. Water and ethyl acetate are added to the reaction mixture, and the organic layer is separated. The organic layer is washed with water and saturated aqueous solution of sodium chloride successively and dried over anhydrous magnesium sulfate, the solvent is distilled off under reduced pressure, and the residue is purified by column chromatography (eluent: hexane:ethyl acetate=20:1 to 3:1) to obtain 6.30 g of methyl 6-methoxybenzo[b]thiophene-5-carboxylate as an oily product.

REFERENTIAL EXAMPLE 13

(1) In 30 mL of 90% aqueous solution of methanol is dissolved 5.90 g of methyl 6-fluoro-7-methoxybenzo-[b]thiophene-5-carboxylate, to which is added 1.18 g of sodium hydroxide. The mixture is stirred at ambient temperature for 6 hours. The reaction mixture is concentrated under reduced pressure, the residue is mixed with water and hexane, and the aqueous layer is separated. The aqueous layer is adjusted to pH 1 with 6 mol/L hydrochloric acid, and the deposited crystal is collected by filtration, washed with water and dried. Thus, 5.20 g of 6-fluoro-7-methoxybenzo[b]thiophene-5-carboxylic acid is obtained as a light brown-colored crystalline product.

The following compounds are obtained in the same manner as above.

6-Fluoro-7-(methylthio)benzo[b]thiophene-5-carboxylic acid

6-Fluoro-7-methylbenzo[b]thiophene-5-carboxylic acid

4-Chlorobenzo[b]thiophene-5-carboxylic acid

6-Chlorobenzo[b]thiophene-5-carboxylic acid

4-Fluorobenzo[b]thiophene-5-carboxylic acid

6-Fluorobenzo[b]thiophene-5-carboxylic acid

4-Fluorobenzo[b]thiophene-7-carboxylic acid

6-Fluorobenzo[b]thiophene-7-carboxylic acid

6-Methoxybenzo[b]thiophene-5-carboxylic acid (2) In 40 mL of methylene chloride is suspended 4.00 g of 6-fluoro-7-methoxybenzo[b]thiophene-5-carboxylic acid, to which is added 1.55 mL of thionyl chloride. The mixture is heated under reflux for 2 hours. The reaction mixture is concentrated under reduced pressure, and the residue is dissolved in 40 mL of methylene chloride. At an ice-cooled temperature, 200 mL of 0.5 mol/L solution of diazomethane in diethyl ether is added to the solution obtained above, and the mixture thus formed is stirred at ambient temperature for one hour. Then, 6.1 mL of acetic acid is added to the reaction mixture, and the mixture is stirred at ambient temperature for 10 minutes. Then, water and ethyl acetate are added, and the organic layer is separated. The organic layer is washed with saturated aqueous solution of sodium chloride and dried over anhydrous magnesium sulfate, and the solvent is distilled off under reduced pressure. The residue is suspended in 40 mL of methanol, a mixture of 2.03 g of silver benzoate and 17.3 mL of triethylamine is added at 5° C., and the mixture thus formed is stirred at ambient temperature for one hour. Water and ethyl acetate are added to the reaction mixture, pH is adjusted to 1 with 6 mol/L hydrochloric acid, the insoluble matter is filtered off, and the organic layer is separated. The organic layer is washed with saturated aqueous solution of sodium chloride and dried over anhydrous magnesium sulfate, the solvent is distilled off under reduced pressure, and the residue thus obtained is purified by column chromatography (eluent: hexane:ethyl acetate=5:1) to obtain 3.87 g of methyl 2-(6-fluoro-7-methoxybenzo[b]thiophen-5-yl)-acetate.

IR(neat)cm$^{-1}$: 2952, 1735, 1466, 1073.

NMR(CDCl$_3$)δ: 3.73(3H, s), 3.78(2H, d, J=2 Hz), 4.13 (3H, d, J=2 Hz), 7.26(1H, s), 7.35(1H, s), 7.41(1H, s).

The following compounds are obtained in the same manner as above.

Methyl 2-[6-fluoro-7-(methylthio)benzo[b]thiophen-5-yl]-acetate

IR(neat)cm$^{-1}$: 1740, 1435, 1263, 1202, 1173, 1033, 746, 707.

NMR(CDCl$_3$)δ: 2.54(3H, s), 3.73(3H, s), 3.79(2H, d, J=2 Hz), 7.27(1H, d, J=5 Hz), 7.42(1H, d, J=5 Hz), 7.63(1H, d, J=7 Hz).

Methyl 2-(6-fluoro-7-methylbenzo[b]thiophen-5-yl)-acetate

Methyl 2-(4-chlorobenzo[b]thiophen-5-yl)-acetate

IR(neat)cm$^{-1}$: 1737, 1169, 840, 756.

Methyl 2-(6-chlorobenzo[b]thiophen-5-yl)-acetate

Methyl 2-(4-fluorobenzo[b]thiophen-5-yl)-acetate

Methyl 2-(6-fluorobenzo[b]thiophen-5-yl)-acetate

IR(neat)cm$^{-1}$: 1740, 1465, 1243, 1166.

Methyl 2-(4-fluorobenzo[b]thiophen-7-yl)-acetate

IR(neat)cm$^{-1}$: 1737, 1447, 1215, 1163, 913.

Methyl 2-(6-fluorobenzo[b]thiophen-7-yl)-acetate

IR(neat)cm$^{-1}$: 1744, 1472, 1240, 960, 814.

Methyl 2-(6-methoxybenzo[b]thiophen-5-yl)-acetate

IR (neat) cm$^{-1}$: 1736, 1436, 1046.

(3) In 39 mL of methanol is dissolved 3.87 g of methyl 2-(6-fluoro-7-methoxybenzo[b]thiophen-5-yl)-acetate, to which is added 6.6 mL of 3 mol/L aqueous solution of sodium hydroxide. The mixture is stirred at ambient temperature for 4 hours. The reaction mixture is concentrated under reduced pressure, the residue thus obtained is mixed with water and ethyl acetate, and pH is adjusted to 1 with 6 mol/L hydrochloric acid. The organic layer is separated, washed with saturated aqueous solution of sodium chloride and dried over anhydrous magnesium sulfate, and the solvent is distilled off under reduced pressure. Thus, 2.80 g of 2-(6-fluoro-7-methoxybenzo[b]thiophen-5-yl)-acetic acid is obtained as a brown-colored crystalline product.

NMR(DMSO-d$_6$)δ: 3.75(2H, d, J=2 Hz), 4;05(3H, d, J=2 Hz), 7.41(1H, d, J=5 Hz), 7.54(1H, d, J=5 Hz), 7.72(1H, d, J=5 Hz), 12.5(1H, brs).

The following compounds are obtained in the same manner as above.

2-[6-Fluoro-7-(methylthio)benzo[b]thiophen-5-yl]-acetic acid 2-(6-Fluoro-7-methylbenzo[b]thiophen-5-yl)-acetic acid 2-(4-Chlorobenzo[b]thiophen-5-yl)-acetic acid 2-(6-Chlorobenzo[b]thiophen-5-yl)-acetic acid 2-(4-Fluorobenzo[b]thiophen-5-yl)-acetic acid 2-(6-Fluorobenzo[b]thiophen-5-yl)-acetic acid 2-(4-Fluorobenzo[b]thiophen-7-yl)-acetic acid 2-(6-Fluorobenzo[b]thiophen-7-yl)-acetic acid 2-(6-Methoxybenzo[b]thiophen-5-yl)-acetic acid

REFERENTIAL EXAMPLE 14

In 17.4 mL of methylene chloride is suspended 1.74 g of 2-(6-fluoro-7-methoxybenzo[b]thiophen-5-yl)-acetic acid, to which is added 13.8 mL of 1 mol/L solution of boron trifluoride in methylene chloride. The mixture is stirred at ambient temperature for 3 hours. The reaction mixture is introduced into a mixture of methylene chloride and water and the organic layer is separated. The organic layer is washed with saturated aqueous solution of sodium chloride and dried over anhydrous magnesium sulfate, and the solvent is distilled off under reduced pressure. Thus, 1.42 g of 2-(6-fluoro-7-hydroxybenzo[b]thiophen-5-yl)-acetic acid is obtained as a gray-colored crystalline product.

NMR(DMSO-$d_6$)δ: 3.71(2H, d, J=2 Hz), 7.28(1H, d, J=5 Hz), 7.34(1H, d, J=5 Hz), 7.65(1H, d, J=5 Hz), 10.5(1H, brs).

REFERENTIAL EXAMPLE 15

In 8.1 mL of tetrahydrofuran is dissolved 1.42 g of 2-(6-fluoro-7-methoxybenzo[b]thiophen-5-yl)-acetic acid. At an ice-cooled temperature, 4.8 mL of 1 mol/L solution of borane-tetrahydrofuran complex in tetrahydrofuran is added to the solution obtained above, and the resulting mixture is stirred at ambient temperature for 2 hours. Ethyl acetate and water are added to the reaction mixture, pH is adjusted to 10 with 2 mol/L aqueous solution of sodium hydroxide, and the organic layer is separated. The organic layer is washed with saturated aqueous solution of sodium chloride and dried over anhydrous magnesium sulfate, and the solvent is distilled off under reduced pressure. Thus, 0.72 g of 2-(6-fluoro-7-methoxybenzo[b]thiophen-5-yl)-1-ethanol is obtained as an oily product.

IR(neat)cm$^{-1}$: 3358, 2938, 1460, 1357, 1076.

NMR(CDCl$_3$)δ: 3.01(2H, dt, J=2, 7 Hz), 3.91(2H, t, J=7 Hz), 4.12(3H, d, J=2 Hz), 7.25(1H, s), 7.33(1H, s), 7.39(1H, s).

The following compounds are obtained in the same manner as above.

2-[6-Fluoro-7-(methylthio)benzo[b]thiophen-5-yl]-1-ethanol

IR(neat)cm$^{-1}$: 3363, 2926, 1428, 1257, 1045.

NMR(CDCl$_3$)δ: 2.54(3H, s), 3.02(2H, t, J=6 Hz), 3.92 (2H, t, J=6 Hz), 7.28(1H, d, J=5 Hz), 7.42(1H, d, J=5 Hz), 7.63(1H, d, J=6 Hz).

2-(6-Fluoro-7-methylbenzo[b]thiophen-5-yl)-1-ethanol 2-(4-Chlorobenzo[b]thiophen-5-yl)-1-ethanol IR(neat)cm$^{-1}$: 3322, 1419, 1052, 696.

NMR(CDCl$_3$)δ: 3.16(2H, t, J=7 Hz), 3.94(2H, t, J=7 Hz), 7.26(1H, d, J=8 Hz), 7.50(2H, s), 7.72(1H, d, J=8 Hz).

2-(6-Chlorobenzo[b]thiophen-5-yl)-1-ethanol 2-(4-Fluorobenzo[b]thiophen-5-yl)-1-ethanol IR(neat)cm$^{-1}$: 3362, 1464, 1245, 1043.

NMR(CDCl$_3$)δ: 3.09(2H, t, J=7 Hz), 3.98(2H, t, J=7 Hz), 6.8–7.2(2H, m), 7.40(1H, s), 7.35(1H, s).

2-(6-Fluorobenzo[b]thiophen-5-yl)-1-ethanol 2-(4-Fluorobenzo[b]thiophen-7-yl)-1-ethanol IR(neat)cm$^{-1}$: 3366, 1444, 1043, 911, 702.

NMR(CDCl$_3$)δ: 3.02(2H, t, J=6 Hz), 3.90(2H, t, J=6 Hz), 7.1–7.4(3H, m), 7.63(1H, d, J=8 Hz).

2-(6-Fluorobenzo[b]thiophen-7-yl)-1-ethanol

IR(neat)cm$^{-1}$; 3348, 1469, 1235, 1043, 810.

NMR(CDCl$_3$)δ: 3.19(2H, t, J=6 Hz), 3.98(2H, t, J=6 Hz), 7.12(1H, t, J=9 Hz), 7.29(1H, d, J=5 Hz), 7.39(1H, d, J=5 Hz), 7.65(1H, dd, J=5, 9 Hz).

2-(6-Methoxybenzo[b]thiophen-5-yl)-1-ethanol

IR(neat)cm$^{-1}$: 3368, 1468, 1244, 1045.

NMR(CDCl$_3$)δ: 3.00(2H, t, J=6 Hz), 3.87(2H, t, J=6 Hz), 3.89(3H, s), 7.23(1H, s), 7.32(1H, s), 7.35(1H, s), 7.59(1H, s).

6-Fluoro-5-(2-hydroxyethyl)benzo[b]thiophen-7-ol

IR(neat)cm$^{-1}$: 3463, 1465, 1350, 1213, 1032, 1012, 871, 705.

NMR(DMSO-$d_6$)δ: 2.84(2H, t, J=7 Hz), 3.5–3.8(2H, m), 4.72(1H, t, J=5 Hz), 7.25(1H, d, J=5 Hz), 7.31(1H, d, J=5 Hz), 7.62(1H, d, J=5 Hz), 10.31(1H, brs).

REFERENTIAL EXAMPLE 16

(1) In 90 mL of ethanol is dissolved 25 g of toluenethiol, to which are added 12.42 g of potassium hydroxide and 33.3 mL of bromoacetaldehyde diethyl acetal. The mixture thus obtained is heated under reflux for 2.5 hours. The reaction mixture is introduced into a mixture of ice water and diethyl ether, and the organic layer is separated. The organic layer is washed with saturated aqueous solution of sodium chloride and dried over anhydrous magnesium sulfate, the solvent is distilled off under reduced pressure, and the residue is distilled under reduced pressure (113–125° C./2.5 mm Hg) to obtain 41.5 g of 1-[(2,2-diethoxyethyl)sulfanyl]-3-methylbenzene as an oily product.

(2) Using 1-[(2,2-diethoxyethyl)sulfanyl]-3-methylbenzene, the procedure of Referential Example 11(2) is repeated. Thus, 23.53 g of a mixture of 4-methylbenzo[b]thiophene and 6-methylbenzo[b]thiophene is obtained.

(3) In 350 mL of benzene is dissolved 23.53 g of a mixture of 4-methylbenzo[b]thiophene and 6-methylbenzo[b]thiophene, to which are added 0.77 g of benzoyl peroxide and 39.56 g of N-bromosuccinimide. The mixture thus formed is heated under reflux for 2 hours. After cooling the mixture to 50° C., 70 mL of acetic acid, 70 mL of water and 44.51 g of hexamethylenetetramine are added, and the mixture thus formed is heated under reflux for 2 hours. The solvent is distilled off under reduced pressure, the residue is mixed with water and ethyl acetate, and pH is adjusted to 7.5 with potassium carbonate. The organic layer is separated, washed with water and saturated aqueous solution of sodium chloride successively, and dried over anhydrous magnesium sulfate. The solvent is distilled off under reduced pressure, and the residue is purified by column chromatography (eluent: hexane:ethyl acetate=19:1 to 15:1). Thus, 5.24 g of benzo[b]thiophene-4-carboaldehyde, 5.09 g of benzo[b]thiophene-6-carboaldehyde and 6.71 g of mixture thereof are obtained as oily products.

REFERENTIAL EXAMPLE 17

(1) In an atmosphere of nitrogen, 4.85 g of (methoxymethyl)triphenylphosphonium chloride is suspended in 40 mL of tetrahydrofuran. Then, 1.5 mL of diisopropylamine is added to the suspension, and cooled to −60° C. After dropwise adding thereto 6.6 mL of 1.6 mol/L solution of n-butyllithium in hexane, the mixture thus obtained is stirred for 30 minutes at an ice-cooled temperature. Then, the reaction mixture is cooled to −60° C., a solution of 1.72 g of benzo[b]thiophene-4-carboaldehyde in 15 mL of tetrahydrofuran is dropwise added, and the resulting mixture is allowed to stand overnight at ambient temperature. The reaction mixture is introduced into a mixture of water and ethyl acetate, and the organic layer is separated. The organic layer is washed with saturated aqueous solution of sodium chloride and dried over anhydrous magnesium sulfate, the solvent is distilled off under reduced pressure, the residue is treated with diethyl ether, and the deposited crystal is filtered off. The solvent is distilled off from the filtrate under reduced pressure, and the residue thus obtained is purified by column chromatography (eluent: n-hexane:ethyl acetate=100:1 to 50:1) to obtain 1.04 g of 2-benzo[b]thiophen-4-yl-1-ethenyl methyl ether as an oily product.

(2) In a mixture of 8 mL of dioxane and 2.4 ml of water is dissolved 1.57 g of 2-benzo[b]thiophen-4-yl-1-ethenyl methyl ether, to which is added 0.09 mL of concentrated sulfuric acid. The mixture is heated under reflux for 1.5 hours. Water and ethyl acetate are added to the reaction mixture, and the organic layer is separated. The organic layer is washed with saturated aqueous solution of sodium chloride and dried over anhydrous magnesium sulfate, and the solvent is distilled off under reduced pressure. Thus, 1.45 g of a crude product of 2-benzo[b]thiophen-4-ylaldehyde is obtained.

(3) In 8 mL of 90% methanol is suspended 0.16 g of sodium boron hydride. At an ice-cooled temperature, a solution of 1.45 g of 2-benzo[b]thiophen-4-ylacetaldehyde in 6 mL of methanol is dropwise added to the suspension obtained above, and the resulting mixture is stirred at ambient temperature for 30 minutes. Water and ethyl acetate are added to the reaction mixture, pH is adjusted to 2.0 with 6 mol/L hydrochloric acid, and the organic layer is separated. The organic layer is washed with saturated aqueous solution of sodium chloride and dried over anhydrous magnesium sulfate, and the solvent is distilled off under reduced pressure, and the residue is purified by column chromatography (eluent: toluene:ethyl acetate=50:1 to 2:1) to obtain 0.88 g of 2-benzo[b]-thiophen-4-yl-1-ethanol.

IR(neat)cm$^{-1}$: 3348, 1043, 759.

NMR(CDCl$_3$)δ: 3.22(2H, t, J=6 Hz), 3.96(2H, t, J=6 Hz), 7.21(1H, d, J=7 Hz), 7.31(1H, t, J=7 Hz), 7.46(2H, s), 7.78(1H, d, J=7 Hz).

REFERENTIAL EXAMPLE 18

(1) In 8.4 mL of dimethyl sulfoxide is dissolved 1.67 g of benzo[b]thiophene-6-carboaldehyde, to which are added 2.52 g of trimethylsulfonium iodide and 0.69 g of potassium hydroxide. The mixture is stirred at 50–55° C. for 3 hours. The reaction mixture is introduced into a mixture of water and diethyl ether, and the organic layer is separated. The organic layer is washed with saturated aqueous solution of sodium chloride and dried over anhydrous magnesium sulfate, and the solvent is distilled off under reduced pressure. Thus, 1.80 g of a crude product of 2-benzo[b]thiophen-6-yloxysilane is obtained.

(2) In 20 mL of tetrahydrofuran is suspended 0.16 g of sodium boron hydride, to which is dropwise added 0.85 mL of boron trifluoride diethyl ether complex. The mixture thus formed is stirred at ambient temperature for 10 minutes. At an ice-cooled temperature, a solution of 1.80 g of 2-benzo[b]thiophen-6-yloxysilane in 10 ml of tetrahydrofuran is dropwise added, and the resulting mixture is stirred at ambient temperature for 2 hours. Acetone is added to the reaction mixture and stirred for 30 minutes, and then water and ethyl acetate are added and the organic layer is separated. The organic layer is washed with water and saturated aqueous solution of sodium chloride successively and dried over anhydrous magnesium sulfate, and the solvent is distilled off under reduced pressure. The residue is purified by column chromatography (eluent: hexane:ethyl acetate=10:1 to 5:1). Thus, 0.81 g of 2-benzo[b]thiophen-6-yl-1-ethanol is obtained as an oily product.

IR(neat)cm$^{-1}$: 3352, 2938, 1047, 817.

NMR(CDCl$_3$)δ: 2.98(2H, t, J=6 Hz), 3.91(2H, t, J=6 Hz), 7.2–7.4(3H, m), 7.72(1H, s), 7.76(1H, d, J=8 Hz).

The following compound is obtained in the same manner as above.

2-(2-Methyl-1,3-benzothiazol-5-yl)-ethanol

REFERENTIAL EXAMPLE 19

(1) In 50 mL of dimethyl sulfoxide is dissolved 2,3,4,5-tetrafluorobenzoic acid, to which are added 4.6 mL of bromoethane and 8.19 g of potassium carbonate. The mixture is stirred at 70° C. for 2 hours. Then, 18.52 g of potassium carbonate and 15.02 g of tert-butyl ethyl malonate, and the mixture is stirred at 90° C. for 2 hours. Water and toluene are added to the reaction mixture, pH is adjusted to 4 with 6 mol/L hydrochloric acid, and the organic layer is separated. The organic layer is washed with water, saturated aqueous solution of sodium chloride successively and dried over anhydrous magnesium sulfate, the solvent is distilled off under reduced pressure, and the residue is dissolved in 50 mL of toluene and heated under reflux for 3.5 hours together with 0.2 g of p-toluenesulfonic acid monohydrate. Water and ethyl acetate are added to the reaction mixture, and the organic layer is separated. The organic layer is washed with water, saturated aqueous solution of sodium bicarbonate and saturated aqueous solution of sodium chloride and dried over anhydrous magnesium sulfate. By distilling off the solvent under reduced pressure, there is obtained 15.2 g of ethyl 4-ethoxycarbonyl-2,3,6-trifluorophenylacetate.

(2) In 66 mL of dimethyl sulfoxide is dissolved 15.2 g of ethyl 4-ethoxycarbonyl-2,3,6-trifluorophenylacetate, to which are added 7.84 g of potassium carbonate and 4.54 g of sodium hydrosulfide n-hydrate(purity 70%). The mixture is stirred at 40° C. for 2 hours. The reaction mixture is cooled to 5° C., 8.1 mL of tert-butyl chloroacetate is added, and the mixture thus formed is stirred at the same temperature as above for 20 minutes. Then, 6.36 g of potassium tert-butoxide is added and stirred for one hour. Water and ethyl acetate are added to the reaction mixture, pH is adjusted to 1 with 6 mol/L hydrochloric acid, and the organic layer is separated. The organic layer is washed with water, saturated aqueous solution of sodium bicarbonate and saturated aqueous solution of sodium chloride successively and dried over anhydrous magnesium sulfate, and the solvent is distilled off under reduced pressure. Thus, 19.2 g of tert-butyl 6-(2-ethoxy-2-oxoethyl)-5,7-difluoro-3-oxo-2,3-dihydrobenzo[b]thiophene-2-carboxylate is obtained.

(3) In 60 mL of toluene is dissolved 19.2 g of tert-butyl 6-(2-ethoxy-2-oxoethyl)-5,7-difluoro-3-oxo-2,3- dihydrobenzo[b]thiophene-2-carboxylate, to which is added 0.96 g of p-toluenesulfonic acid monohydrate. The mixture is heated under reflux for 2.5 hours. Water is added to the reaction mixture, and the organic layer is separated. The organic layer is washed with water, saturated aqueous solution of sodium bicarbonate and saturated aqueous solution of sodium chloride and dried over anhydrous magnesium sulfate, and the solvent is distilled off under reduced pressure. The residue thus obtained is dissolved in 100 ml of methanol, 0.97 g of sodium boron hydride is added, and the mixture thus formed is stirred at ambient temperature for 30 minutes. Then, 5.88 g of p-toluenesulfonic acid monohydrate is added and the mixture thus formed is heated under reflux for one hour. The reaction mixture is concentrated under reduced pressure, water and ethyl acetate are added to the residue, and the organic layer is separated. The organic layer is washed with water, saturated aqueous solution of sodium bicarbonate and saturated aqueous solution of sodium chloride successively and dried over anhydrous magnesium sulfate, the solvent is distilled off under reduced pressure, and the residue is purified by column chromatography (eluent: hexane:ethyl acetate=50:1 to 20:1) to obtain 1.98 g of ethyl 2-(5,7-difluorobenzo[b]thiophen-6-yl)acetate as an oily product.

IR(neat)cm$^{-1}$: 1740, 1180, 1049.

NMR(CDCl$_3$)δ: 1.26(3H, t, J=7 Hz), 3.83(2H, s), 4.20 (2H, q, J=7 Hz), 7.2–7.4(2H, m), 7.51(1H, d, J=5 Hz).

(4) Using ethyl 2-(5,7-diflouorobenzo[b]thiophen-6-yl)-acetate, the procedures of Referential Example 13(3) and Referential Example 15 are repeated to obtain the following compounds.

2-(5,7-Difluorobenzo[b]thiophen-6-yl)-1-acetic acid

IR(neat)cm$^{-1}$: 1707, 1406, 1047.

NMR(CDCl$_3$)δ: 3.89(2H, s), 7.2–7.4(2H, m), 7.53(1H, d, J=5 Hz), 8.2(1H, brs).

2-(5,7-Difluoroenzo[b]thiophen-6-yl)-1-ethanol

IR(neat)cm$^{-1}$: 3356, 1404, 1045.

NMR(CDCl$_3$)δ: 3.08(2H, t, J=6 Hz), 3.89(2H, t, J=6 Hz), 7.25(1H, d, J=5 Hz), 7.35(1H, d, J=4 Hz), 7.49(1H, d, J=5 Hz).

REFERENTIAL EXAMPLE 20

Using 2-benzo[b]thiophen-5-yl-acetic acid as a starting material, the procedures of Referential Example 9(1) and Referential Example 17(3) are repeated to obtain the following compounds.

1-Benzo[b]thiophen-5-yl-acetone

IR(KBr)cm$^{-1}$: 1712, 1311, 1159, 708.

NMR(CDCl$_3$)δ: 2.17(3H, s), 3.80(2H, s), 7.17(1H, d, J=8 Hz), 7.29(1H, d, J=5 Hz), 7.45(1H, d, J=5 Hz), 7.65(1H, s), 7.84(1H, d, J=8 Hz).

1-Benzo[b]thiophen-5-yl-2-propanol

IR(neat)cm$^{-1}$: 3386, 2968, 2928, 1051.

NMR(CDCl$_3$)δ: 1.27(3H, d, J=6 Hz), 1.56(1H, s), 2.76 (1H, dd, J=7, 13 Hz), 2.95(1H, dd, J=5, 13 Hz), 3.9–4.2(1H, m), 7.19(1H, d, J=8 Hz), 7.28(1H, d, J=5 Hz), 7.44(1H, d, J=5 Hz), 7.66(1H, s), 7.82(1H, d, J=8 Hz).

PREPARATION EXAMPLE 1

A high-speed agitation type granulator (VG-01; manufactured by Powerex) is charged with 11.5 g of 2-{[2-(2-benzo[b]thiophen-5-ylethoxy)ethyl](methyl)amino}-1-ethanol oxalate (the compound of Example 68), 97 g of partially pregelatinized starch (Starch 1500, product of Japan Karakon), 188.5 g of lactose (Tabletose: Megre) and 3 g of magnesium stearate having passed 32 mesh sieve. The materials are blended together at a blade rotation rate of 600 rpm and a chopper rotation rate of 3,200 rpm for 10 minutes. The blended powdery material is packed into No.1 capsule so that one capsule contained 300 mg of the material. Thus, capsules are obtained.

PREPARATION EXAMPLE 2

A mixture consisting of 23 g of 2-{[2-(benzo[b]-thiophen-5-ylethoxy)ethyl](methyl)amino}-1-ethanol oxalate and 66 g of lactose (Tabletose; Megre) is sieved by means of Powermill (PS-04S; Dulton) equipped with a 16 mesh sieve. To the powder having passed the sieve are added 120 q of lactose, 120 g of crystalline cellulose (Abisel; product of Asahi Kasei) and 67 g of corn starch, the mixture thus obtained is homogenized for 5 minutes. Then, 4 g of magnesium stearate having passed 32 mesh sieve is added to the homogenized powder obtained above, and the mixture thus obtained is homogenized for an additional 5 minutes to obtain a tablet-forming powder. The powder is formed into tablet by means of a rotary tableting machine (HP-18; manufactured by Hata Tekko Co.) quipped with a pestle having a diameter of 7.5 mm, to obtain a 200 mg weight tablet preparation.

PREPARATION EXAMPLE 3

In 10 L of a physiological saline (The Japanese Pharmacopoeia grade) is dissolved 1.15 g of 2-{[2-(2-benzo[b]thiophen-5-ylethoxy)ethyl](methyl)-amino}-1-ethanol oxalate. The solution thus obtained is filtered through a membrane filter of 0.22 μm, and the filtrate is divided into 100 ml portions and poured into sterilized glass bottles. By stopping the bottles with rubber stoppers followed by rolling with aluminum caps, there is obtained an injection.

INDUSTRIAL UTILIZABILITY

The n-alkoxyalkyl-N,N-dialkylamine derivative or a salt thereof according to the present invention exhibits excellent anti-hypoxic activity, nerve-protecting activity and nerve-regeneration promoting activity, and therefore is useful as an agent for use in the treatment of neurodegenerative diseases such as alzheimer's disease, parkinson's disease, amyotrophic lateral sclerosis, huntington's chorea , diabetic neuropathy, drug-induced neuropathy, traumatic neuropathy, etc.

What is claimed is:

1. An N-alkoxyalkyl-N,N-dialkylamine compound represented by the following general formula, or its salt, hydrate or solvate:

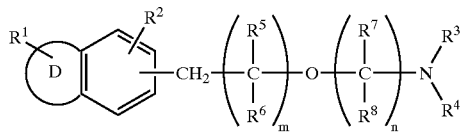

wherein

R$^1$ and R$^2$ are the same or different and represent at least one group selected from the group consisting of a hydrogen atom, a halogen atom, an unsubstituted or substituted alkyl, aryl, aralkyl, alkoxy, aryloxy, alkylthio, arylthio, alkenyl, alkenyloxy, amino, alkylsulfonyl, arylsulfonyl, carbamoyl or heterocyclic group, an unprotected or protected amino, hydroxyl or carboxyl group, a nitro group and an oxo group;

$R^3$ and $R^4$ are the same or different and represent an unsubstituted or substituted alkyl, cycloalkyl or aralkyl group;

each of $mR^5$'s, $mR^6$'s, $nR^7$'s and $nR^8$'s are the same or different and represent a hydrogen atom or an alkyl group;

the ring D represents a 5-membered heterocyclic ring containing sulfur;

m represents an integer of 1–5; and n represents an integer of 1–6.

2. The N-alkoxyalkyl-N,N-dialkylamine compound or its salt, hydrate or solvate of claim 1, wherein ring D is thiophene.

3. The N-alkoxyalkyl-N,N-dialkylamine compound or its salt, hydrate or solvate of claim 1, wherein ring D is thiazole.

4. The N-alkoxyalkyl-N,N-dialkylamine compound or its salt, hydrate or solvate, of claim 1, wherein ring D is isothiazole.

5. The N-alkoxyalkyl-N,N-dialkylamine compound or its salt, hydrate or solvate, according to claim 1, wherein $R^1$ and $R^2$ are the same or different and represent at least one substituent selected from the group consisting of a hydrogen atom, a halogen atom, an unsubstituted or substituted alkyl, aryl, alkoxy, alkylthio, carbamoyl or heterocyclic group, an unprotected or protected hydroxyl or carboxyl group, and an oxo group.

6. The N-alkoxyalkyl-N,N-dialkylamine compound or its salt, hydrate, or solvate, according to claim 1, wherein $R^1$ and $R^2$ are the same or different and represent a hydrogen atom, an unsubstituted alkoxy group, or a substituted alkoxy group.

7. The N-alkoxyalkyl-N,N-dialkylamine compound of claim 1 or its salt, hydrate, or solvate, wherein m is 1, and n is 2.

8. The N-alkoxyalkyl-N,N-dialkylamine compound of claim 1 or its salt, hydrate, or solvate, wherein $R^3$ is methyl or ethyl, and $R^4$ is an unsubstituted alkyl, cycloalkyl or aralkyl group.

9. The N-alkoxyalkyl-N,N-dialkylamine compound of claim 1 or its salt, hydrate, or solvate, wherein $R^3$ is methyl or ethyl, and $R^4$ is a substituted alkyl, cycloalkyl or aralkyl group.

10. An optical isomer, geometrical isomer or tautomer of the compound of claim 1.

11. An acid salt of the compound of claim 1.

12. A base salt of the compound of claim 1.

13. An alkali metal salt of the compound of claim 1.

14. An alkaline earth metal salt of the compound of claim 1.

15. A nitrogen-containing organic base salt of the compound of claim 1.

16. A composition comprising:

the compound of claim 1 or its salt, hydrate or solvate, and a pharmaceutically acceptable additive or excipient.

17. The composition of claim 16 in a form suitable for oral administration.

18. The composition of claim 16 in the form of an aerosol.

19. The composition of claim 16 in an injectable form.

20. The composition of claim 16 in the form of an external preparation, ointment or suppository.

21. A method for treating a neurodegenerative disease associated with amyloid β protein (Aβ)-induced nerve cell death or 4-hydroxy-2-nonenal (HNE)-induced nerve cell death comprising administering to a subject in need thereof an effective amount of the compound of claim 1.

22. A method for inducing nerve regeneration comprising administering to a subject in need thereof an effective amount of the compound of claim 1.

23. A method for reducing hypoxia comprising administering to a subject in need thereof an effective amount of the compound of claim 1.

24. A method of inhibiting the death of nerve cell induced by amyloid β protein (Aβ) or induced by 4-hydroxy-2-nonenal (HNE) comprising administering to a nerve cell an effective amount of the compound of claim 1.

* * * * *